United States Patent
Mulvihill et al.

(10) Patent No.: US 11,079,384 B2
(45) Date of Patent: *Aug. 3, 2021

(54) BIOMARKERS AND METHODS FOR DIAGNOSIS OF EARLY STAGE PANCREATIC DUCTAL ADENOCARCINOMA

(71) Applicant: University of Utah Research Foundation, Salt Lake City, UT (US)

(72) Inventors: Sean J. Mulvihill, Salt Lake City, UT (US); Matthew A. Firpo, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/658,937

(22) Filed: Oct. 21, 2019

(65) Prior Publication Data
US 2020/0088733 A1    Mar. 19, 2020

Related U.S. Application Data

(63) Continuation of application No. 15/308,579, filed as application No. PCT/US2015/029429 on May 6, 2015, now Pat. No. 10,451,628.

(60) Provisional application No. 61/990,029, filed on May 7, 2014.

(51) Int. Cl.
*G01N 33/574* (2006.01)
*C12N 15/113* (2010.01)

(52) U.S. Cl.
CPC . *G01N 33/57438* (2013.01); *G01N 33/57488* (2013.01); *C12N 15/113* (2013.01); *G01N 2800/52* (2013.01); *G01N 2800/56* (2013.01); *G01N 2800/60* (2013.01)

(58) Field of Classification Search
CPC ....... G01N 33/57438; G01N 33/57488; G01N 2800/52; G01N 2800/56; G01N 2800/60
See application file for complete search history.

(56) References Cited

U.S. PATENT DOCUMENTS

| | | | |
|---|---|---|---|
| 2010/0092476 | A1 | 4/2010 | Hanash et al. |
| 2013/0323734 | A1 | 12/2013 | Kidd et al. |

FOREIGN PATENT DOCUMENTS

| | | |
|---|---|---|
| EP | 15789055.9 | 5/2015 |
| WO | WO-2003/093443 A2 | 11/2003 |
| WO | WO-2006/017573 A2 | 2/2006 |
| WO | WO-2013/126539 A1 | 8/2013 |
| WO | PCT/US2015/029429 | 5/2015 |
| WO | WO-2015/171736 A2 | 11/2015 |

OTHER PUBLICATIONS

Rosenberg et al. (Gastroenterology, 2004, 127:1704-1713) (Year: 2004).*

(Continued)

*Primary Examiner* — Jeremy C Flinders
(74) *Attorney, Agent, or Firm* — Ballard Spahr LLP

(57) ABSTRACT

The present invention provides biomarker compositions and methods for the diagnosis and prognosis of PDAC. In a particular embodiment, the invention provides methods and compositions for screening, diagnosis and prognosis of early stage, asymptomatic PDAC.

8 Claims, 14 Drawing Sheets

(56) References Cited

OTHER PUBLICATIONS

Harsha et al. (PLoS Medicine, 2009, 6(4):e1000046) (Year: 2009).*
U.S. Appl. No. 61/990,029, filed May 7, 2014, Sean J. Mulvihill.
U.S. Appl. No. 15/308,579, filed Nov. 6, 2016, Sean J. Mulvihill (University of Utah Research Foundation).
U.S. Appl. No. 10/451,628, filed Oct. 22, 2019, Sean J. Mulvihill (University of Utah Research Foundation).
Aggelis et al., Proteomic identification of differentially expressed plasma membrane proteins in renal cell carcinoma by stable isotope labelling of a von Hippel-Lindau transfectant cell line model. Proteomics. 2009; 9(8): 2118-30.
Dooley et al., Hepatocyte-Specific Smad7 Expression Attenuates TGF-β-Mediated Fibrogenesis and Protects Against Liver Damage. Gastroenterology. 2008; 135(2):642-59 (64 pages).
Hong et al., ALCAM Is Associated With Chemoresistance and Tumor Cell Adhesion in Pancreatic Cancer. J Surg Oncol. 2010; 101:564-9.
Kahlert et al., Increased expression of ALCAM/CD166 in pancreatic cancer is an independent prognostic marker for poor survival and early tumour relapse. Br J Cancer. 2009; 101(3):457-64.
Ni et al., Prognostic Value of CD166 Expression in Cancers of the Digestive System: A Systematic Review and Meta-Analysis. PLoS One. 2013; 8(8):e70958 (8 pages).
Tachezy et al., ALCAM (CD166) Expression and Serum Levels in Pancreatic Cancer. PLoS One. 2012; 7(6):e39018 (8 pages).

International Search Report and written Opinion dated Nov. 4, 2015 by the International Searching Authority for Patent Application No. PCT/US2015/029429, which was filed on May 6, 2015 and published as WO 2015/171736 on Nov. 12, 2015 (Inventor—Mulvihill et al.; Applicant—University of Utah Research Foundation) (10 pages).
International Preliminary Report on Patentability dated Nov. 8, 2016 by the International Searching Authority for Patent Application No. PCT/US2015/029429, which was filed on May 6, 2015 and published as WO 2015/171736 on Nov. 12, 2015 (Inventor—Mulvihill et al.; Applicant—University of Utah Research Foundation) (8 pages).
Partial European Search Report dated Oct. 20, 2017 by the European Patent Office for Application No. 15789055.9, which was filed on May 6, 2015 and published as EP 3140426 on Mar. 15, 2017 (Inventor—Mulvihill et al.; Applicant—University of Utah Research Foundation) (9 pages).
European Search Report dated Jan. 22, 2018 2017 by the European Patent Office for Application No. 15789055.9, which was filed on May 6, 2015 and published as EP 3140426 on Mar. 15, 2017 (Inventor—Mulvihill et al.; Applicant—University of Utah Research Foundation) (14 pages).
Communication Pursuant to Article 94(3) EPC dated Sep. 20, 2018 by the European Patent Office for Application No. 15789055.9, which was filed on May 6, 2015 and published as EP 3140426 on Mar. 15, 2017 (Inventor—Mulvihill et al.; Applicant—University of Utah Research Foundation) (4 pages).

* cited by examiner

| | Healthy Controls (CON) | Chronic Pancreatitis (ChPT) | PDAC Stage I-II | PDAC Stage III-IV |
|---|---|---|---|---|
| Total Cases | 50 | 20 | 30 | 20 |
| Median Age (Range) | 60 (29-83) | 51.5 (21-78) | 67 (48-86) | 64.5 (44-83) |
| Female Cases | 25 | 10 | 15 | 10 |
| Female Median Age (Range) | 61 (58-81) | 51.5 (21-70) | 69 (55-86) | 65.5 (54-83) |
| Male Cases | 25 | 10 | 15 | 10 |
| Male Median Age (Range) | 55 (29-83) | 57 (29-78) | 64 (48-82) | 62.5 (44-71) |

BIOMARKERS AND METHODS FOR DIAGNOSIS OF EARLY STAGE PANCREATIC DUCTAL ADENOCARCINOMA

This application is a continuation of U.S. patent application Ser. No. 15/308,579, now U.S. Pat. No. 10,451,628, filed Nov. 2, 2016, which is a national phase application of International Application No. PCT/US2015/029429, filed May 6, 2015, which claims the benefit of priority of U.S. Provisional Application No. 61/990,029, filed May 7, 2014. The content of these earlier filed applications is hereby incorporated by reference herein in its entirety.

This invention was made with government support under Grant Numbers R03 CA115225, U01 CA151650 and R33 CA155586 awarded by the National Institutes of Health. The government has certain rights in the invention.

The invention relates generally to the field of personalized medicine and, more specifically to compositions and methods for diagnosis of early stage pancreatic ductal adenocarcinoma (PDAC).

BACKGROUND

Pancreatic ductal adenocarcinoma (PDAC) is an aggressive tumor with poor survival rates in part due to the fact that most cases are initially diagnosed too late in the course of the disease for potentially curative resection. With the highest mortality rate of any cancer, PDAC has a 5-year survival rate less than 5%. Despite extensive efforts in recent years, advancement in treatments has been meager. Surgical resection remains the only curative intervention, but only 18% of patients are diagnosed at early stages when surgical resection is an option. The remaining 82% of patients present with advanced disease at diagnosis. For these patients, disease management is limited to palliation. A substantial determinant for the lethality of PDAC is the late presentation due to asymptomatic development and earlier detection would improve outcomes by identifying the disease while still amenable to potentially curative intervention.

Screening programs designed to detect early stage PDAC in asymptomatic populations face considerable challenges, not the least of which is the need for a highly accurate test that would limit false-positive identifications in this relatively rare disease. On the basis of the differential accumulation of mutations in primary and metastatic lesions, a recent study estimated an average of 11.7 years elapsed from tumor initiation to overt cancer development and an average of 6.8 years elapsed between the development of overt cancer and the development of metastatic disease. The finding that pancreatic tumors are present for a significant period of time before clinical manifestation emphasizes the potential for screening and early detection. Unfortunately, even the best currently available blood-based biomarker, CA 19-9, has significant shortcomings, including unacceptably low accuracy, that limit its use to monitoring disease progression. No single biomarker or combinations of a few biomarkers has emerged that markedly improves on CA 19-9 diagnostic accuracy.

There is a great need to to identify biomarkers that can be combined into an accurate and cost-effective biomarker panel that would be an useful screening tool in asymptomatic populations. The present invention addresses this need by providing compositions and methods for the diagnosis of early stage PDAC. Related methods and advantages are provided as well.

SUMMARY

The present invention provides compositions and methods for the diagnosis and prognosis of PDAC. In a particular embodiment, the invention provides methods and compositions for screening, diagnosis and prognosis of early stage, asymptomatic PDAC.

In one aspect, the invention provides a panel of isolated biomarkers comprising N of the biomarkers listed in Tables 1 through 4. In another aspect, the invention provides a panel of isolated biomarkers comprising N of the biomarkers listed in Table 1, 2, 3 or 4. In one aspect, the invention provides a panel of isolated biomarkers comprising N of the biomarkers listed two or more of Tables 1 through 4. In some embodiments, N is a number selected from the group consisting of 2 to 30.

In some embodiments, the biomarker panel comprises at least two of the isolated biomarkers selected from the group consisting of activated leukocyte cell adhesion molecule (ALCAM), angiogenin (ANG), AXL receptor tyrosine kinase (AXL), BCL2-associated athanogene 3 (BAG3), basigin (BSG, EMMPRIN, CD147), cancer antigen 19-9 (CA 19-9), carcinoembryonic antigen-related cell adhesion molecule 1 (biliary glycoprotein) (CEACAM1), collagen, type XVIII, alpha 1 (endostatin) (COL18A1), epithelial cell adhesion molecule (EPCAM), soluble hyaluronic acid (HA), haptoglobin (HP), intercellular adhesion molecule 1 (ICAM1), insulin-like growth factor binding protein 2 (IGFBP2), insulin-like growth factor binding protein 4 (IGFBP4), lipocalin 2 (LCN2, NGAL), leucine-rich alpha-2-glycoprotein 1 (LRG1), matrix metallopeptidase 2 (MMP2, gelatinase A, 72 kDa gelatinase, 72 kDa type IV collagenase), matrix metallopeptidase 7 (MMP7, matrilysin, uterine), matrix metallopeptidase 9 (MMP9, gelatinase B, 92 kDa gelatinase, 92 kDa type IV collagenase), mesothelin (MSLN), DJ-1 protein (PARK7), platelet basic protein (PPBP), proteoglycan 4 (PRG4), SPARC-like 1 (SPARCL1, hevin), secreted phosphoprotein 1 (SPP1, osteopontin, OPN), transforming growth factor, beta-induced, 68 kDa (TGFBI), thrombospondin 1 (THBS1), TIMP metallopeptidase inhibitor 1 (TIMP1), tumor necrosis factor receptor superfamily, member 1A (TNFRSF1A), vascular endothelial growth factor C (VEGFC).

In additional embodiments, the biomarker panel comprises at least two of the isolated biomarkers selected from the group consisting of activated leukocyte cell adhesion molecule (ALCAM), angiogenin (ANG), AXL receptor tyrosine kinase (AXL), alpha-2-glycoprotein 1, zinc-binding (AZGP1), BCL2-associated athanogene 3 (BAG3), basigin (BSG) (EMMPRIN, CD147), cancer antigen 19-9 (CA 19-9), carcinoembryonic antigen-related cell adhesion molecule 5 (CEACAM5) (CEA), carcinoembryonic antigen-related cell adhesion molecule 1 (CEACAM1, biliary glycoprotein), collagen, type XVIII, alpha 1 (endostatin) (COL18A1), epithelial cell adhesion molecule (EPCAM), gelsolin (GSN), soluble hyaluronic acid (HA), haptoglobin (HP), intercellular adhesion molecule 1 (ICAM1), insulin-like growth factor binding protein 2 (IGFBP2), insulin-like growth factor binding protein 4 (IGFBP4), lipocalin 2 (LCN2) (NGAL), LIM and senescent cell antigen-like domains 1 (LIMS1) (PINCH), leucine-rich alpha-2-glycoprotein 1 (LRG1), lactoferrin (LTF), matrix metallopeptidase 11 (MMP11) (stromelysin 3), matrix metallopeptidase 2 (MMP2) (gelatinase A, 72 kDa gelatinase, 72 kDa type IV collagenase), matrix metallopeptidase 7 (MMP7) (matrilysin, uterine), matrix metallopeptidase 9 (MMP9) (gelatinase B, 92 kDa gelatinase, 92 kDa type IV collagenase), mesothelin (MSLN), DJ-1 protein (PARK7), platelet factor 4 (PF4), plectin (PLEC), platelet basic protein (PPBP), proteoglycan 4 (PRG4), serum amyloid A (SAA), SPARC-like 1 (SPARCL1)(hevin) secreted phosphoprotein 1 (SPP1)

(osteopontin, OPN), transforming growth factor, beta-induced, 68 kDa (TGFBI), thrombospondin 1 (THBS1), TIMP metallopeptidase inhibitor 1 (TIMP1), tumor necrosis factor receptor superfamily, member 1A (TNFRSF1A), and vascular endothelial growth factor C (VEGFC).

In some embodiments, the biomarker panel comprises one or more peptides comprising a fragment of a biomarker selected from activated leukocyte cell adhesion molecule (ALCAM), angiogenin (ANG), AXL receptor tyrosine kinase (AXL), BCL2-associated athanogene 3 (BAG3), basigin (BSG, EMMPRIN, CD147), cancer antigen 19-9 (CA 19-9), carcinoembryonic antigen-related cell adhesion molecule 1 (biliary glycoprotein) (CEACAM1), collagen, type XVIII, alpha 1 (endostatin) (COL18A1), epithelial cell adhesion molecule (EPCAM), soluble hyaluronic acid (HA), haptoglobin (HP), intercellular adhesion molecule 1 (ICAM1), insulin-like growth factor binding protein 2 (IGFBP2), insulin-like growth factor binding protein 4 (IGFBP4), lipocalin 2 (LCN2, NGAL), leucine-rich alpha-2-glycoprotein 1 (LRG1), matrix metallopeptidase 2 (MMP2, gelatinase A, 72 kDa gelatinase, 72 kDa type IV collagenase), matrix metallopeptidase 7 (MMP7, matrilysin, uterine), matrix metallopeptidase 9 (MMP9, gelatinase B, 92 kDa gelatinase, 92 kDa type IV collagenase), mesothelin (MSLN), DJ-1 protein (PARK7), platelet basic protein (PPBP), proteoglycan 4 (PRG4), SPARC-like 1 (SPARCL1, hevin), secreted phosphoprotein 1 (SPP1, osteopontin, OPN), transforming growth factor, beta-induced, 68 kDa (TGFBI), thrombospondin 1 (THBS1), TIMP metallopeptidase inhibitor 1 (TIMP1), tumor necrosis factor receptor superfamily, member 1A (TNFRSF1A), vascular endothelial growth factor C (VEGFC).

In additional embodiments, the biomarker panel comprises one or more peptides comprising a fragment of a biomarker selected from activated leukocyte cell adhesion molecule (ALCAM), angiogenin (ANG), AXL receptor tyrosine kinase (AXL), alpha-2-glycoprotein 1, zinc-binding (AZGP1), BCL2-associated athanogene 3 (BAG3), basigin (BSG) (EMMPRIN, CD147), cancer antigen 19-9 (CA 19-9), carcinoembryonic antigen-related cell adhesion molecule 5 (CEACAM5) (CEA), carcinoembryonic antigen-related cell adhesion molecule 1 (CEACAM1, biliary glycoprotein), collagen, type XVIII, alpha 1 (endostatin) (COL18A1), epithelial cell adhesion molecule (EPCAM), gelsolin (GSN), soluble hyaluronic acid (HA), haptoglobin (HP), intercellular adhesion molecule 1 (ICAM1), insulin-like growth factor binding protein 2 (IGFBP2), insulin-like growth factor binding protein 4 (IGFBP4), lipocalin 2 (LCN2) (NGAL), LIM and senescent cell antigen-like domains 1 (LIMS1) (PINCH), leucine-rich alpha-2-glycoprotein 1 (LRG1), lactoferrin (LTF), matrix metallopeptidase 11 (MMP11) (stromelysin 3), matrix metallopeptidase 2 (MMP2) (gelatinase A, 72 kDa gelatinase, 72 kDa type IV collagenase), matrix metallopeptidase 7 (MMP7) (matrilysin, uterine), matrix metallopeptidase 9 (MMP9) (gelatinase B, 92 kDa gelatinase, 92 kDa type IV collagenase), mesothelin (MSLN), DJ-1 protein (PARK7), platelet factor 4 (PF4), plectin (PLEC), platelet basic protein (PPBP), proteoglycan 4 (PRG4), serum amyloid A (SAA), SPARC-like 1 (SPARCL1)(hevin) secreted phosphoprotein 1 (SPP1) (osteopontin, OPN), transforming growth factor, beta-induced, 68 kDa (TGFBI), thrombospondin 1 (THBS1), TIMP metallopeptidase inhibitor 1 (TIMP1), tumor necrosis factor receptor superfamily, member 1A (TNFRSF1A), and vascular endothelial growth factor C (VEGFC).

In some embodiments, the panel of isolated biomarkers comprises at least two of the isolated biomarkers selected from the group consisting of BCL2-associated athanogene 3 (BAG3), cancer antigen 19-9 (CA 19-9), carcinoembryonic antigen-related cell adhesion molecule 1 (CEACAM1), soluble hyaluronic acid (HA), insulin-like growth factor binding protein 2 (IGFBP2), DJ-1 protein (PARK7), and secreted phosphoprotein 1 (SPP1). In further embodiments, the panel of isolated biomarkers can be used in methods to distinguish healthy individuals from early stage PDAC.

In additional embodiments, the panel of isolated biomarkers comprises at least two of the isolated biomarkers selected from the group consisting of BCL2-associated athanogene 3 (BAG3), cancer antigen 19-9 (CA 19-9), carcinoembryonic antigen-related cell adhesion molecule 1 (CEACAM1), epithelial cell adhesion molecule (EPCAM), lipocalin 2 (LCN2), mesothelin (MSLN), DJ-1 protein (PARK7), proteoglycan 4 (PRG4), secreted phosphoprotein 1 (SPP1), and tumor necrosis factor receptor superfamily, member 1A (TNFRSF1A). In further embodiments, the panel of isolated biomarkers can be used in methods to distinguish healthy individuals and individuals afflicted with chronic pancreatitis from early stage PDAC.

In additional embodiments, the panel of isolated biomarkers comprises at least two of the isolated biomarkers selected from the group consisting of activated leukocyte cell adhesion molecule (ALCAM), BCL2-associated athanogene 3 (BAG3), basigin (BSG), soluble hyaluronic acid (HA), DJ-1 protein (PARK7), proteoglycan 4 (PRG4), SPARC-like 1 (SPARCL1)(hevin), and transforming growth factor, beta-induced, 68 kDa (TGFBI). In related embodiments, the panels of isolated biomarkers can further comprise basigin (BSG).

In some embodiments, the panel of isolated biomarkers comprises one or more peptides comprising a fragment of a biomarker selected from BCL2-associated athanogene 3 (BAG3), cancer antigen 19-9 (CA 19-9), carcinoembryonic antigen-related cell adhesion molecule 5 (CEACAM5), soluble hyaluronic acid (HA), insulin-like growth factor binding protein 2 (IGFBP2), DJ-1 protein (PARK7), and secreted phosphoprotein 1 (SPP1). In further embodiments, the panel of isolated biomarkers can be used in methods to distinguish healthy individuals from early stage PDAC.

In additional embodiments, the panel of isolated biomarkers comprises one or more peptides comprising a fragment of a biomarker selected from BCL2-associated athanogene 3 (BAG3), cancer antigen 19-9 (CA 19-9), carcinoembryonic antigen-related cell adhesion molecule 5 (CEACAM5), epithelial cell adhesion molecule (EPCAM), lipocalin 2 (LCN2), mesothelin (MSLN), DJ-1 protein (PARK7), proteoglycan 4 (PRG4), secreted phosphoprotein 1 (SPP1), and tumor necrosis factor receptor superfamily, member 1A (TNFRSF1A). In further embodiments, the panel of isolated biomarkers can be used in methods to distinguish healthy individuals and individuals afflicted with chronic pancreatitis from early stage PDAC.

In additional embodiments, the panel of isolated biomarkers comprises one or more peptides comprising a fragment of a biomarker selected from activated leukocyte cell adhesion molecule (ALCAM), BCL2-associated athanogene 3 (BAG3), basigin (BSG), soluble hyaluronic acid (HA), DJ-1 protein (PARK7), proteoglycan 4 (PRG4), SPARC-like 1 (SPARCL1)(hevin), and transforming growth factor, beta-induced, 68 kDa (TGFBI). In related embodiments, the panels of isolated biomarkers can further comprise basigin (BSG).

In further embodiments, the biomarker panel comprises at least two of the isolated biomarkers selected from the group consisting of of miR-100a, miR-1290, miR-155, miR-18a, miR-196a, miR-21, miR-210, miR-221, miR-24, miR-31, miR-375, and miR-885.

In additional embodiments, the biomarker panel comprises at least two of the isolated biomarkers selected from the group consisting of KRAS, SMAD4, CDKN2A and TP53.

In additional embodiments, the biomarker panel comprises at least two of the isolated biomarkers selected from the group consisting of activated leukocyte cell adhesion molecule (ALCAM), angiogenin (ANG), AXL receptor tyrosine kinase (AXL), alpha-2-glycoprotein 1, zinc-binding (AZGP1), BCL2-associated athanogene 3 (BAG3), basigin (BSG) (EMMPRIN, CD147), cancer antigen 19-9 (CA 19-9), carcinoembryonic antigen-related cell adhesion molecule 5 (CEACAM5) (CEA), carcinoembryonic antigen-related cell adhesion molecule 1 (CEACAM1)(biliary glycoprotein), collagen, type XVIII, alpha 1 (endostatin) (COL18A1), epithelial cell adhesion molecule (EPCAM), gelsolin (GSN), soluble hyaluronic acid (HA), haptoglobin (HP), intercellular adhesion molecule 1 (ICAM1), insulin-like growth factor binding protein 2 (IGFBP2), insulin-like growth factor binding protein 4 (IGFBP4), lipocalin 2 (LCN2) (NGAL), LIM and senescent cell antigen-like domains 1 (LIMS1) (PINCH), leucine-rich alpha-2-glycoprotein 1 (LRG1), lactoferrin (LTF), matrix metallopeptidase 11 (MMP11) (stromelysin 3), matrix metallopeptidase 2 (MMP2) (gelatinase A, 72 kDa gelatinase, 72 kDa type IV collagenase), matrix metallopeptidase 7 (MMP7) (matrilysin, uterine), matrix metallopeptidase 9 (MMP9) (gelatinase B, 92 kDa gelatinase, 92 kDa type IV collagenase), mesothelin (MSLN), DJ-1 protein (PARK7), platelet factor 4 (PF4), plectin (PLEC), platelet basic protein (PPBP), proteoglycan 4 (PRG4), serum amyloid A (SAA), SPARC-like 1 (SPARCL1)(hevin) secreted phosphoprotein 1 (SPP1) (osteopontin, OPN), transforming growth factor, beta-induced, 68 kDa (TGFBI), thrombospondin 1 (THBS1), TIMP metallopeptidase inhibitor 1 (TIMP1), tumor necrosis factor receptor superfamily, member 1A (TNFRSF1A), vascular endothelial growth factor C (VEGFC), miR-100a, miR-1290, miR-155, miR-18a, miR-196a, miR-21, miR-210, miR-221, miR-24, miR-31, miR-375, miR-885, KRAS, SMAD4, CDKN2A and TP53.

In one embodiment, the present disclosure includes methods for determining a probability for early stage pancreatic ductal adenoncarcinoma (PDAC) in an individual, the method comprising detecting a measurable feature of each of N biomarkers selected from the biomarkers listed in Tables 1 through 4 in a biological sample obtained from said individual, and analyzing said measurable feature to determine the probability for early stage PDAC in the individual.

In some embodiments, the methods of the invention can be used to determine the probability for survival of an individual diagnosed with PDAC.

In some embodiments, the methods of the invention can be used to prognose the length of survival of an individual diagnosed with PDAC.

In additional embodiments, the methods of the invention can be used to determine the probability for disease recurrence in an individual diagnosed with PDAC, chronic pancreatitis, early stage PDAC, late stage PDAC, and other periampullary diseases.

In one embodiment, the methods of the invention can be used to determine a probability of a positive response to therapy for pancreatic ductal adenoncarcinoma (PDAC) in an individual.

Other features and advantages of the invention will be apparent from the detailed description, and from the claims.

BRIEF DESCRIPTION OF THE DRAWINGS

FIG. 1A shows the relative distribution of BSG in the different groups. Each data point represents an individual case. Mean plasma levels of BSG were significantly elevated in the PDAC stage I-II group relative to the three other groups (P<0.005, only significant comparisons by ANOVA and Tukey-Kramer tests). FIG. 1B shows subject demographics.

FIG. 2A shows relative growth monitored for a constant number if initially plated RFP-MIA PaCa-2 cells co-cultured with an increasing number of either PCAF2. FIG. 2B shows the effect of co-culture with PCAF2 on RFP-MIA PaCa-2 cell growth monitored while keeping the initial total cell plating density constant. Data represents the combined results of 3-4 independent experiments. For each experiment, 4-6 replicate wells for each condition were performed in parallel. Bracket indicates conditions significantly elevated relative to RFP-MIA PaCa-2 cells alone by ANOVA and Fisher's PLSD post-hoc test (P<0.01).

FIGS. 6A-C represent different assumptions about the individual biomarkers: FIG. 6A indicates panel characteristics assuming all biomarkers in the panel yield 45% sensitivity at the 95% specificity threshold (e.g. TIMP-1), FIG. 6B indicates panel characteristics assuming all biomarkers in the panel yield 32% sensitivity at the 95% specificity threshold (the average of the 9 biomarkers examined), and FIG. 6C indicates panel characteristics assuming all biomarkers in the panel yield 19% sensitivity at the 95% specificity threshold (e.g. haptoglobin). Different assumptions about the mean correlation ratios between individual biomarkers constituting the panels are indicated by the color legend. Numbers above the data points indicate the minimum number of biomarkers in the panels required to be above the 95% specificity threshold in order to make a positive diagnosis of PDAC.

DETAILED DESCRIPTION

Figures 1A, 1B:
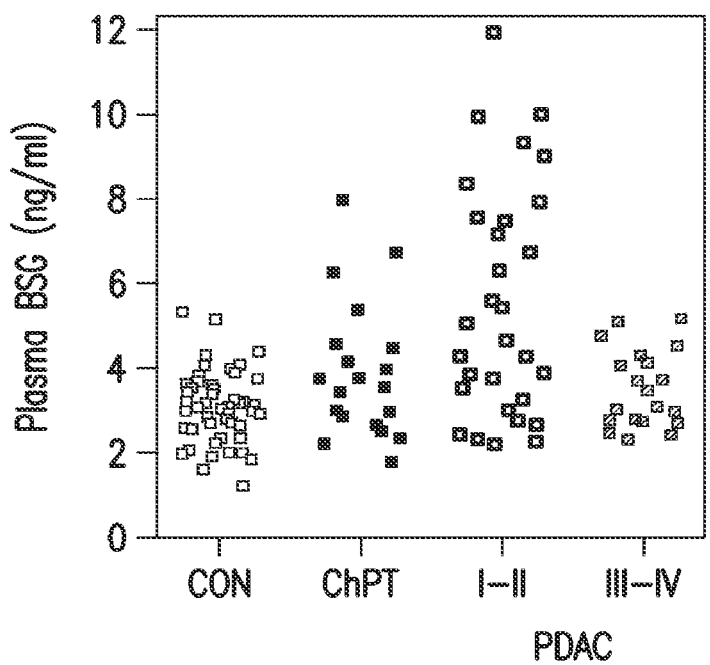
FIGS. 1A-B show the results from plasma BSG determinations by ELISA.

The present disclosure is based, in part, on the discovery that certain protein and/or nucleic acid biomarkers can be combined into panels that are reliable prognostic and diagnostic tools for PDAC. The disclosure provides biomarker panels, methods and kits for determining the probability for PDAC in an individual. One major advantage of the present disclosure is that the combination of biomarkers into a panel confers a high level of specificity and sensitivity on the prognostic and diagnostic methods described herein. The present invention is of particular benefit to asymptomatic populations of individuals with PDAC that would evade detection with traditional screening methods.

The present invention is further based, in part, on the discovery of basigin (BSG) as a biomarker for detection of early stage PDAC that upon being combined with additional biomarkers results in a strong classifier panel with unexpectedly high specificity and sensitivity. In addition, the differential levels of BSG in healthy control, chronic pancreatitis, early stage PDAC and late stage PDAC cases disclosed herein make it a powerful biomarker for related methods and applications.

Basigin (BSG), a cell surface glycoprotein, plays a role in the interaction of carcinoma and mesenchymal cells through the stimulation of extracellular matrix remodeling enzymes. Circulating BSG has also been demonstrated as a diagnostic/prognostic biomarker for numerous cancers. Our preliminary evidence indicates that plasma BSG is significantly elevated in early stage PDAC cases (stage I and II) compared to healthy controls, chronic pancreatitis cases, and late stage PDAC cases (stage III and IV), which had mean levels comparable to healthy control subjects. These results suggest that circulating BSG is an early stage phenomenon during PDAC development and the first early stagespecific biomarker identified for PDAC.

In one embodiment, the present disclosure includes methods for determining a probability for early stage pancreatic ductal adenoncarcinoma (PDAC) in an individual, the method comprising detecting a measurable feature of each of N biomarkers selected from the biomarkers listed in Tables 1 through 4 in a biological sample obtained from said individual, and analyzing said measurable feature to determine the probability for early stage PDAC in the individual.

In another embodiment, the present disclosure includes methods for determining a probability of recurrence of pancreatic ductal adenoncarcinoma (PDAC) in an individual, the method comprising detecting a measurable feature of each of N biomarkers selected from the biomarkers listed in Tables 1 through 4 in a biological sample obtained from said individual, and analyzing said measurable feature to determine the probability of recurrence of PDAC in the individual.

In a further embodiment, the present disclosure includes methods for prognosing length of survival of an individual diagnosed with pancreatic ductal adenoncarcinoma (PDAC), the method comprising detecting a measurable feature of each of N biomarkers selected from the biomarkers listed in Tables 1 through 4 in a biological sample obtained from said individual, and analyzing said measurable feature to prognose length of survival for the individual with PDAC.

In one embodiment, the present disclosure includes a method of determining a probability of a positive response to therapy for pancreatic ductal adenocarcinoma (PDAC) in an individual, the method comprising detecting a measurable feature of each of N biomarkers selected from the biomarkers listed in Tables 1 through 4 in a biological sample obtained from said individual, and analyzing said measurable feature to determine the probability of a positive response to therapy for PDAC in said individual. In related embodiments, the therapy is selected from the group consisting of prophylactic anticoagulants, resection, neoadjuvant chemotherapy and chemoradiation.

In a further embodiment, the present disclosure includes a method of selecting a therapy for pancreatic ductal adenoncarcinoma (PDAC) in an individual, the method comprising detecting a measurable feature of each of N biomarkers selected from the biomarkers listed in Tables 1 through 4 in a biological sample obtained from said individual, and analyzing said measurable feature to determine the probability of a positive response to therapy for PDAC in said individual. In related embodiments, the therapy is selected from the group consisting of prophylactic anticoagulants, resection, neoadjuvant chemotherapy and chemoradiation.

In one embodiment, the present disclosure includes methods for determining a probability for early stage pancreatic ductal adenoncarcinoma (PDAC) in an individual, the method comprising detecting a measurable feature of each of N biomarkers selected from the biomarkers listed in one of Tables 1, 2, 3, or 4 in a biological sample obtained from said individual, and analyzing said measurable feature to determine the probability for early stage PDAC in the individual.

In another embodiment, the present disclosure includes methods for determining a probability of recurrence of pancreatic ductal adenoncarcinoma (PDAC) in an individual, the method comprising detecting a measurable feature of each of N biomarkers selected from the biomarkers listed in one of Tables 1, 2, 3, or 4 in a biological sample obtained from said individual, and analyzing said measurable feature to determine the probability of recurrence of PDAC in the individual.

In a further embodiment, the present disclosure includes methods for prognosing length of survival of an individual diagnosed with pancreatic ductal adenoncarcinoma (PDAC), the method comprising detecting a measurable feature of each of N biomarkers selected from the biomarkers listed in one of Tables 1, 2, 3, or 4 in a biological sample obtained from said individual, and analyzing said measurable feature to prognose length of survival for the individual with PDAC.

In one embodiment, the present disclosure includes a method of determining a probability of a positive response to therapy for pancreatic ductal adenoncarcinoma (PDAC) in an individual, the method comprising detecting a measurable feature of each of N biomarkers selected from the biomarkers listed in one of Tables 1, 2, 3, or 4 in a biological sample obtained from said individual, and analyzing said measurable feature to determine the probability of a positive response to therapy for PDAC in said individual. In related embodiments, the therapy is selected from the group consisting of prophylactic anticoagulants, resection, neoadjuvant chemotherapy and chemoradiation.

In a further embodiment, the present disclosure includes a method of selecting a therapy for pancreatic ductal adenoncarcinoma (PDAC) in an individual, the method comprising detecting a measurable feature of each of N biomarkers selected from the biomarkers listed in one of Tables 1, 2, 3, or 4 in a biological sample obtained from said individual, and analyzing said measurable feature to determine the probability of a positive response to therapy for PDAC in said individual. In related embodiments, the therapy is selected from the group consisting of prophylactic anticoagulants, resection, neoadjuvant chemotherapy and chemoradiation.

In addition to the specific biomarkers identified in this disclosure, for example, by accession number in a public database, sequence, or reference, the invention also contemplates use of biomarker variants that are at least 90% or at least 95% or at least 97% identical to the exemplified sequences and that are now known or later discovered and that have utility for the methods of the invention. These variants may represent polymorphisms, splice variants, mutations, and the like. In this regard, the instant specification discloses multiple art-known proteins in the context of the invention and provides exemplary accession numbers associated with one or more public databases as well as exemplary references to published journal articles relating to these art-known proteins. However, those skilled in the art appreciate that additional accession numbers and journal articles can easily be identified that can provide additional characteristics of the disclosed biomarkers and that the exemplified references are in no way limiting with regard to the disclosed biomarkers. As described herein, various techniques and reagents find use in the methods of the present invention. Suitable samples in the context of the present invention include, for example, blood, plasma, serum, amniotic fluid, vaginal secretions, saliva, and urine. In some embodiments, the biological sample is selected from the group consisting of whole blood, plasma, and serum. In a particular embodiment, the biological sample is serum. As described herein, biomarkers can be detected through a variety of assays and techniques known in the art. As further described herein, such assays include, without limitation, nucleic acid sequencing, polymerase chain reaction (PCR), mass spectrometry (MS)-based assays, antibody-based assays as well as assays that combine aspects of the two.

Protein biomarkers associated with the probability for PDAC in an individual include, but are not limited to, one or more of the isolated biomarkers listed in Tables 1 through 4. In addition to the specific biomarkers, the disclosure further includes biomarker variants that are about 90%, about 95%, or about 97% identical to the exemplified sequences. Variants, as used herein, include polymorphisms, splice variants, mutations, and the like.

Additional markers can be selected from one or more risk indicia, including but not limited to, age, obesity (body mass index), history of smoking/tobacco use, history of chronic pancreatitis, history of diabetes, family history of pancreatic cancer, history of intraductal papillary mucinous neoplasm or pancreatic intraepithelial neoplasia, history of mutations in cyclin-dependent kinase inhibitor 2A (CDKN2A), breast cancer 1, early onset BRCA1), breast cancer 2, early onset (BRCA2), serine/threonine kinase 11 (STK11), mutS homolog 2, colon cancer, nonpolyposis type 1 (*E. coli*) (MSH2), mutL homolog 1, colon cancer, nonpolyposis type 2 (*E. coli*) (MLH1), adenomatous polyposis coli (APC), partner and localizer of BRCA2 (PALB2), protease, serine, 1 (trypsin 1) (PRSS1), serine peptidase inhibitor, Kazal type 1 (SPINK1) genes. Additional risk indicia useful for as markers can be identified using learning algorithms known in the art, such as linear discriminant analysis, support vector machine classification, recursive feature elimination, prediction analysis of microarray, logistic regression, CART, FlexTree, LART, random forest, MART, and/or survival analysis regression, which are known to those of skill in the art and are further described herein.

Provided herein are panels of isolated biomarkers comprising N of the biomarkers selected from the group listed in Tables 1 through 4. In the disclosed panels of biomarkers N can be a number selected from the group consisting of, for example, 2-6, 2-7, 2-8, 2-9, 2-10, 2-11, 2-12, 2 to 24. In the disclosed methods, the number of biomarkers that are detected and whose levels are determined, can be 1, or more than 1, such as 2, 3, 4, 5, 6, 7, 8, 9, 10, 11, 12, 12, 14, 15, 16, 17, 18, 19, 20, 21, 22, 23, 24, 25 or more. In certain embodiments, the number of biomarkers that are detected, and whose levels are determined, can be 1, or more than 1, such as 2, 3, 4, 5, 6, 7, 8, 9, 10, or more. The methods of this disclosure are useful for determining the probability for PDAC in an individual.

While certain of the biomarkers listed in Tables 1 through 4 are useful alone for determining the probability for PDAC in an individual, methods are also described herein for the grouping of multiple subsets of the biomarkers that are each useful as a panel of three or more biomarkers. In some embodiments, the invention provides panels comprising N biomarkers, wherein N is at least three biomarkers. In other embodiments, N is selected to be any number from 3-23 biomarkers.

In yet other embodiments, N is selected to be any number from 2-5, 2-10, 2-15, 2-20, or 2-23. In other embodiments, N is selected to be any number from 3-5, 3-10, 3-15, 3-20, or 3-23. In other embodiments, N is selected to be any number from 4-5, 4-10, 4-15, 4-20, or 4-23. In other embodiments, N is selected to be any number from 5-10, 5-15, 5-20, or 5-23. In other embodiments, N is selected to be any number from 6-10, 6-15, 6-20, or 6-23. In other embodiments, N is selected to be any number from 7-10, 7-15, 7-20, or 7-23. In other embodiments, N is selected to be any number from 8-10, 8-15, 8-20, or 8-23. In other embodiments, N is selected to be any number from 9-10, 9-15, 9-20, or 9-23. In other embodiments, N is selected to be any number from 10-15, 10-20, or 10-23. It will be appreciated that N can be selected to encompass similar, but higher order, ranges.

In some embodiments, the panel of isolated biomarkers comprises one or more, two or more, three or more, four or more, or five isolated biomarkers selected from activated leukocyte cell adhesion molecule (ALCAM), angiogenin (ANG), AXL receptor tyrosine kinase (AXL), BCL2-associated athanogene 3 (BAG3), basigin (BSG, EMMPRIN, CD147), cancer antigen 19-9 (CA 19-9), carcinoembryonic antigen-related cell adhesion molecule 1 (biliary glycoprotein) (CEACAM1), collagen, type XVIII, alpha 1 (endostatin) (COL18A1), epithelial cell adhesion molecule (EPCAM), soluble hyaluronic acid (HA), haptoglobin (HP), intercellular adhesion molecule 1 (ICAM1), insulin-like growth factor binding protein 2 (IGFBP2), insulin-like growth factor binding protein 4 (IGFBP4), lipocalin 2 (LCN2, NGAL), leucine-rich alpha-2-glycoprotein 1 (LRG1), matrix metallopeptidase 2 (MMP2, gelatinase A, 72 kDa gelatinase, 72 kDa type IV collagenase), matrix metallopeptidase 7 (MMP7, matrilysin, uterine), matrix metallopeptidase 9 (MMP9, gelatinase B, 92 kDa gelatinase, 92 kDa type IV collagenase), mesothelin (MSLN), DJ-1 protein (PARK7), platelet basic protein (PPBP), proteoglycan 4 (PRG4), SPARC-like 1 (SPARCL1, hevin), secreted phosphoprotein 1 (SPP1, osteopontin, OPN), transforming growth factor, beta-induced, 68 kDa (TGFBI), thrombospondin 1 (THBS1), TIMP metallopeptidase inhibitor 1 (TIMP1), tumor necrosis factor receptor superfamily, member 1A (TNFRSF1A), vascular endothelial growth factor C (VEGFC).

In certain embodiments, the panel of isolated biomarkers comprises one or more, two or more, three or more, four or more, or five isolated biomarkers selected from activated leukocyte cell adhesion molecule (ALCAM), angiogenin (ANG), AXL receptor tyrosine kinase (AXL), alpha-2-glycoprotein 1, zinc-binding (AZGP1), BCL2-associated athanogene 3 (BAG3), basigin (BSG) (EMMPRIN, CD147), cancer antigen 19-9 (CA 19-9), carcinoembryonic antigen-related cell adhesion molecule 5 (CEACAM5) (CEA), carcinoembryonic antigen-related cell adhesion molecule 1 (CEACAM1) (biliary glycoprotein), collagen, type XVIII, alpha 1 (endostatin) (COL18A1), epithelial cell adhesion molecule (EPCAM), gelsolin (GSN), soluble hyaluronic acid (HA), haptoglobin (HP), intercellular adhesion molecule 1 (ICAM1), insulin-like growth factor binding protein 2 (IGFBP2), insulin-like growth factor binding protein 4 (IGFBP4), lipocalin 2 (LCN2) (NGAL), LIM and senescent cell antigen-like domains 1 (LIMS1) (PINCH), leucine-rich alpha-2-glycoprotein 1 (LRG1), lactoferrin (LTF), matrix metallopeptidase 11 (MMP11) (stromelysin 3), matrix metallopeptidase 2 (MMP2) (gelatinase A, 72 kDa gelatinase, 72 kDa type IV collagenase), matrix metallopeptidase 7 (MMP7) (matrilysin, uterine), matrix metallopeptidase 9 (MMP9) (gelatinase B, 92 kDa gelatinase, 92 kDa type IV collagenase), mesothelin (MSLN), DJ-1 protein (PARK7), platelet factor 4 (PF4), plectin (PLEC), platelet basic protein (PPBP), proteoglycan 4 (PRG4), serum amyloid A (SAA), SPARC-like 1 (SPARCL1)(hevin), secreted phosphoprotein 1 (SPP1) (osteopontin, OPN), transforming growth factor, beta-induced, 68 kDa (TGFBI), thrombospondin 1 (THBS1), TIMP metallopeptidase inhibitor 1 (TIMP1), tumor necrosis factor receptor superfamily, member 1A (TNFRSF1A), and vascular endothelial growth factor C (VEGFC).

In some embodiments, the panel of isolated biomarkers comprises one or more, two or more, three or more, four or more, or five isolated biomarkers selected from miR-100a, miR-1290, miR-155, miR-18a, miR-196a, miR-21, miR-210, miR-221, miR-24, miR-31, miR-375, and miR-885.

In additional embodiments, the biomarker panel comprises one or more, two or more, three or more, four or more, or five isolated biomarkers selected from the group consisting of KRAS, SMAD4, CDKN2A and TP53.

In some embodiments, the panel of isolated biomarkers comprises one or more, two or more, or three of the isolated biomarkers consisting of the biomarkers set forth in Tables 1 through 4.

In some embodiments, the panel of isolated biomarkers comprises one or more peptides comprising a fragment of a biomarker selected from activated leukocyte cell adhesion molecule (ALCAM), angiogenin (ANG), AXL receptor tyrosine kinase (AXL), BCL2-associated athanogene 3 (BAG3), basigin (BSG, EMMPRIN, CD147), cancer antigen 19-9 (CA 19-9), carcinoembryonic antigen-related cell adhesion molecule 1 (biliary glycoprotein) (CEACAM1), collagen, type XVIII, alpha 1 (endostatin) (COL18A1), epithelial cell adhesion molecule (EPCAM), soluble hyaluronic acid (HA), haptoglobin (HP), intercellular adhesion molecule 1 (ICAM1), insulin-like growth factor binding protein 2 (IGFBP2), insulin-like growth factor binding protein 4 (IGFBP4), lipocalin 2 (LCN2, NGAL), leucine-rich alpha-2-glycoprotein 1 (LRG1), matrix metallopeptidase 2 (MMP2, gelatinase A, 72 kDa gelatinase, 72 kDa type IV collagenase), matrix metallopeptidase 7 (MMP7, matrilysin, uterine), matrix metallopeptidase 9 (MMP9, gelatinase B, 92 kDa gelatinase, 92 kDa type IV collagenase), mesothelin (MSLN), DJ-1 protein (PARK7), platelet basic protein (PPBP), proteoglycan 4 (PRG4), SPARC-like 1 (SPARCL1, hevin), secreted phosphoprotein 1 (SPP1, osteopontin, OPN), transforming growth factor, beta-induced, 68 kDa (TGFBI), thrombospondin 1 (THBS1), TIMP metallopeptidase inhibitor 1 (TIMP1), tumor necrosis factor receptor superfamily, member 1A (TNFRSF1A), vascular endothelial growth factor C (VEGFC).

In some embodiments, the panel of isolated biomarkers comprises one or more peptides comprising a fragment of a biomarker selected from activated leukocyte cell adhesion molecule (ALCAM), angiogenin (ANG), AXL receptor tyrosine kinase (AXL), alpha-2-glycoprotein 1, zinc-binding (AZGP1), BCL2-associated athanogene 3 (BAG3), basigin (BSG) (EMMPRIN, CD147), cancer antigen 19-9 (CA 19-9), carcinoembryonic antigen-related cell adhesion molecule 5 (CEACAM5) (CEA), carcinoembryonic antigen-related cell adhesion molecule 1 (CEACAM1) (biliary glycoprotein), collagen, type XVIII, alpha 1 (endostatin) (COL18A1), epithelial cell adhesion molecule (EPCAM), gelsolin (GSN), soluble hyaluronic acid (HA), haptoglobin (HP), intercellular adhesion molecule 1 (ICAM1), insulin-like growth factor binding protein 2 (IGFBP2), insulin-like growth factor binding protein 4 (IGFBP4), lipocalin 2 (LCN2) (NGAL), LIM and senescent cell antigen-like domains 1 (LIMS1) (PINCH), leucine-rich alpha-2-glycoprotein 1 (LRG1), lactoferrin (LTF), matrix metallopeptidase 11 (MMP11) (stromelysin 3), matrix metallopeptidase 2 (MMP2) (gelatinase A, 72 kDa gelatinase, 72 kDa type IV collagenase), matrix metallopeptidase 7 (MMP7) (matrilysin, uterine), matrix metallopeptidase 9 (MMP9) (gelatinase B, 92 kDa gelatinase, 92 kDa type IV collagenase), mesothelin (MSLN), DJ-1 protein (PARK7), platelet factor 4 (PF4), plectin (PLEC), platelet basic protein (PPBP), proteoglycan 4 (PRG4), serum amyloid A (SAA), SPARC-like 1 (SPARCL1)(hevin), secreted phosphoprotein 1 (SPP1) (osteopontin, OPN), transforming growth factor, beta-induced, 68 kDa (TGFBI), thrombospondin 1 (THBS1), TIMP metallopeptidase inhibitor 1 (TIMP1), tumor necrosis factor receptor superfamily, member 1A (TNFRSF1A), and vascular endothelial growth factor C (VEGFC).

The peptides and fragments of the invention can be isolated, synthetic or otherwise markedly different in structure, function, properties or characteristics from their naturally occurring counterparts.

As exemplified herein, accurate diagnostic algorithms can be devised using subsets of the biomarker panels described herein. In some embodiments, the panel of isolated biomarkers comprises one or more peptides comprising a fragment of a biomarker selected from BCL2-associated athanogene 3 (BAG3), cancer antigen 19-9 (CA 19-9), carcinoembryonic antigen-related cell adhesion molecule 1 (CEACAM1), soluble hyaluronic acid (HA), insulin-like growth factor binding protein 2 (IGFBP2), DJ-1 protein (PARK7), and secreted phosphoprotein 1 (SPP1). In further embodiments, the panel of isolated biomarkers can be used in methods to distinguish healthy individuals from early stage PDAC.

In certain embodiments, the panel of isolated biomarkers comprises one or more, two or more, three or more, four or more, or five isolated biomarkers selected from BCL2-associated athanogene 3 (BAG3), cancer antigen 19-9 (CA 19-9), carcinoembryonic antigen-related cell adhesion molecule 1 (CEACAM1), epithelial cell adhesion molecule (EPCAM), lipocalin 2 (LCN2), mesothelin (MSLN), DJ-1 protein (PARK7), proteoglycan 4 (PRG4), secreted phosphoprotein 1 (SPP1), and tumor necrosis factor receptor superfamily, member 1A (TNFRSF1A). In further embodiments, the panel of isolated biomarkers can be used in methods to distinguish healthy individuals and individuals afflicted with chronic pancreatitis from early stage PDAC.

In certain embodiments, the panel of isolated biomarkers comprises one or more, two or more, three or more, four or more, or five isolated biomarkers selected from activated leukocyte cell adhesion molecule (ALCAM), BCL2-associated athanogene 3 (BAG3), basigin (BSG), soluble hyaluronic acid (HA), DJ-1 protein (PARK7), proteoglycan 4 (PRG4), SPARC-like 1 (SPARCL1)(hevin), and transforming growth factor, beta-induced, 68 kDa (TGFBI). In related embodiments, the panels of isolated biomarkers can further comprise basigin (BSG).

In additional embodiments, the panel of isolated biomarkers comprises one or more peptides comprising a fragment of a biomarker selected from BCL2-associated athanogene 3 (BAG3), cancer antigen 19-9 (CA 19-9), carcinoembryonic antigen-related cell adhesion molecule 1 (CEACAM1), epithelial cell adhesion molecule (EPCAM), lipocalin 2 (LCN2), mesothelin (MSLN), DJ-1 protein (PARK7), proteoglycan 4 (PRG4), secreted phosphoprotein 1 (SPP1), and tumor necrosis factor receptor superfamily, member 1A (TNFRSF1A). In further embodiments, the panel of isolated biomarkers can be used in methods to distinguish healthy individuals and individuals afflicted with chronic pancreatitis from early stage PDAC.

In additional embodiments, the panel of isolated biomarkers comprises one or more peptides comprising a fragment of a biomarker selected from activated leukocyte cell adhesion molecule (ALCAM), BCL2-associated athanogene 3 (BAG3), basigin (BSG), soluble hyaluronic acid (HA), DJ-1 protein (PARK7), proteoglycan 4 (PRG4), SPARC-like 1 (SPARCL1)(hevin), and transforming growth factor, beta-induced, 68 kDa (TGFBI). In related embodiments, the panels of isolated biomarkers can further comprise basigin (BSG).

In some embodiments, the panel of isolated biomarkers comprises one or more nucleic acids comprising a fragment of a biomarker selected from miR-100a, miR-1290, miR-155, miR-18a, miR-196a, miR-21, miR-210, miR-221, miR-24, miR-31, miR-375, and miR-885.

In additional embodiments, the biomarker panel comprises one or more nucleic acids comprising a fragment of a biomarker selected from KRAS, SMAD4, CDKN2A and TP53.

It must be noted that, as used in this specification and the appended claims, the singular forms "a", "an" and "the" include plural referents unless the content clearly dictates otherwise. Thus, for example, reference to "a biomarker" includes a mixture of two or more biomarkers, and the like.

The term "about," particularly in reference to a given quantity, is meant to encompass deviations of plus or minus five percent.

As used in this application, including the appended claims, the singular forms "a," "an," and "the" include plural references, unless the content clearly dictates otherwise, and are used interchangeably with "at least one" and "one or more."

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but can include other elements not expressly listed or inherent to such process, method, product-by-process, or composition of matter.

As used herein, the term "panel" refers to a composition, such as an array or a collection, comprising one or more biomarkers. The term can also refer to a profile or index of expression patterns of one or more biomarkers described herein. The number of biomarkers useful for a biomarker panel is based on the sensitivity and specificity value for the particular combination of biomarker values. In one embodiment, the number of biomarkers useful for a biomarker subset or panel is based on the sensitivity and specificity value for the particular combination of biomarker values.

The terms "sensitivity" and "specificity" are used herein with respect to the ability to correctly classify an individual, based on one or more biomarker values detected in their biological sample, as having versus not having one or more of PDAC, chronic pancreatitis, early stage PDAC, late stage PDAC, and other pancreatic and periampullary diseases. Sensitivity indicates the performance of the biomarker(s) with respect to correctly classifying individuals that have pancreatic disease, while specificity indicates the performance of the biomarker(s) with respect to correctly classifying individuals who do not have pancreatic disease. For example, 85% specificity and 90% sensitivity for a panel of markers used to test a set of control samples and pancreatic cancer samples indicates that 85% of the control samples were correctly classified as control samples by the panel, and 90% of the pancreatic cancer samples were correctly classified as pancreatic cancer samples by the panel. The biomarkers identified herein represent a relatively large number of choices for subsets or panels of biomarkers that can be used to effectively detect or diagnose early stage PDAC. Selection of the desired number of such biomarkers depends on the specific combination of biomarkers chosen.

As used herein, and unless otherwise specified, the terms "isolated" and "purified" generally describes a composition of matter that has been removed from its native environment (e.g., the natural environment if it is naturally occurring), and thus is altered by the hand of man from its natural state. An isolated protein or nucleic acid is distinct from the way it exists in nature.

The term "biomarker" refers to a biological molecule, or a fragment of a biological molecule, the change and/or the detection of which can be correlated with a particular physical condition or state. A change in a biomarker that can be correlated with a particular physical condition or state, for example, pancreatic cancer or pancreatic disease can be quantitative, ie. a change in the level that is detected, or qualitative, i.e. a mutation that is detected. The terms "marker," "analyte," and "biomarker" are used interchangeably throughout the disclosure. For example, the biomarkers of the present invention are correlated with an increased likelihood of one or more of PDAC, chronic pancreatitis, early stage PDAC, late stage PDAC, and other pancreatic and periampullary diseases. Such biomarkers include, but are not limited to, biological molecules comprising nucleotides, nucleic acids, nucleosides, amino acids, sugars, fatty acids, steroids, metabolites, peptides, polypeptides, proteins, carbohydrates, lipids, hormones, antibodies, regions of interest that serve as surrogates for biological macromolecules and combinations thereof (e.g., glycoproteins, ribonucleoproteins, lipoproteins). The term encompasses portions or fragments of a biological molecule, for example, a peptide fragment of a protein or polypeptide that comprises at least 5 consecutive amino acid residues, at least 6 consecutive amino acid residues, at least 7 consecutive amino acid residues, at least 8 consecutive amino acid residues, at least 9 consecutive amino acid residues, at least 10 consecutive amino acid residues, at least 11 consecutive amino acid residues, at least 12 consecutive amino acid residues, at least 13 consecutive amino acid residues, at least 14 consecutive amino acid residues, at least 15 consecutive amino acid residues, at least 5 consecutive amino acid residues, at least 16 consecutive amino acid residues, at least 17 consecutive amino acid residues, at least 18 consecutive amino acid residues, at least 19 consecutive amino acid residues, at least 20 consecutive amino acid residues, at least 21 consecutive amino acid residues, at least 22 consecutive amino acid residues, at least 23 consecutive amino acid residues, at least 24 consecutive amino acid residues, at least 25 consecutive amino acid residues, or more consecutive amino acid residues. Similarly, the term also encompasses portions or fragments of a nucleic acid molecule, for example, fragments of a gene.

As used herein, "polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can be single chains or associated chains. Also included within the definition are preproteins and intact mature proteins; peptides or polypeptides derived from a mature protein; fragments of a protein; splice variants; recombinant forms of a protein; protein variants with amino acid modifications, deletions, or substitutions; digests; and post-translational modifications, such as glycosylation, acetylation, phosphorylation, and the like. The peptides and fragments of the invention can be isolated, synthetic or otherwise markedly different in structure, function, properties or characteristics from their naturally occurring counterparts.

In some embodiments described herein, one or more biomarkers belongs to a class of small RNAs referred to as microRNAs (miRNAs). First described in *Caenorhabditis elegans* in 1993, 1 miRNAs were subsequently found to be conserved in various plant and animal species in 2000 and soon emerged as potentially useful diagnostic and prognostic markers in cancer. Unlike mRNA, miRNAs are only 19-25 nucleotides in size and do not encode amino-acid sequences. In contrast to the vast diversity of mRNA transcripts, the number of miRNA species is much smaller, with 851 human miRNAs reported to date (December 2007, miRBase, Sanger Institute). Despite this limited complexity, miRNAs have been shown to be of profound biological importance, negatively regulating gene expression at the post-transcriptional level. It is estimated based on sequence complementality that each miRNA can potentially bind to hundreds of different mRNA species. Such binding, which occurs mostly at the 3'-untranslated regions of mRNA transcripts but may also occur at the 5'-untranslated or the coding region, could lead to decreased protein expression of the target gene, either by follicular adenomacilitating degradation of the target mRNA or by suppression of the translational machinery. Through these negative regulatory mechanisms, miRNA have been shown to affect various biological processes in both normal and diseased states, including tumorigenesis in human.

The invention also provides a method of determining probability for early stage PDAC in an individual, the method comprising detecting a measurable feature of each of N biomarkers selected from the biomarkers listed in Tables 1 through 4 in a biological sample obtained from the individual, and analyzing the measurable feature to determine the probability for early stage PDAC in the individual. As disclosed herein, a measurable feature comprises fragments or derivatives of each of said N biomarkers selected from the biomarkers listed in Tables 1 through 4. In some embodiments of the disclosed methods detecting a measurable feature comprises quantifying an amount of each of N biomarkers selected from the biomarkers listed in Tables 1 through 4, combinations or portions and/or derivatives thereof in a biological sample obtained from the individual.

Although described and exemplified with reference to methods of determining probability for early stage PDAC in an individual, the present disclosure is similarly applicable to methods of determining probability for PDAC, chronic pancreatitis, late stage PDAC, and other periampullary diseases. It will be apparent to one skilled in the art that each of the aforementioned methods has specific and substantial utilities and benefits with regard to these related conditions.

In some embodiments, the method of determining probability for early stage PDAC in an individual and related methods disclosed herein comprise detecting a measurable feature of each of N biomarkers, wherein N is selected from the group consisting of 2 to 30. In further embodiments, the disclosed methods of determining probability for early stage PDAC in an individual and related methods disclosed herein comprise detecting a measurable feature of each of at least two isolated biomarkers selected from the group consisting of the biomarkers set forth in Tables 1 through 4. In further embodiments, the disclosed methods of determining probability for early stage PDAC in an individual and related methods disclosed herein comprise detecting a measurable feature of each of at least two isolated biomarkers selected from the group consisting of the biomarkers set forth in Table 1. In additional embodiments, the disclosed methods of determining probability for early stage PDAC in an individual and related methods disclosed herein comprise detecting a measurable feature of each of at least two isolated biomarkers selected from the group consisting of the biomarkers selected from the group consisting of the biomarkers set forth in Table 2. In further embodiments, the disclosed methods of determining probability for early stage PDAC in an individual and related methods disclosed herein comprise detecting a measurable feature of each of at least two isolated biomarkers selected from the group consisting of the biomarkers set forth in Table 3.

As used herein, "individual" refers to a test subject or patient. The individual can be a mammal or a non-mammal. In various embodiments, the individual is a mammal. A mammalian individual can be a human or non-human. In various embodiments, the individual is a human. A healthy or normal individual is an individual in which the disease or condition of interest (including, for example, pancreatic diseases, pancreatic-associated diseases, or other pancreatic conditions) is not detectable by conventional diagnostic methods.

As used herein, "diagnose", "diagnosing", "diagnosis", and variations thereof refer to the detection, determination, or recognition of a health status or condition of an individual on the basis of one or more signs, symptoms, data, or other information pertaining to that individual. The health status of an individual can be diagnosed as healthy/normal (i.e., a diagnosis of the absence of a disease or condition) or diagnosed as ill/abnormal (i.e., a diagnosis of the presence, or an assessment of the characteristics, of a disease or condition). The terms "diagnose", "diagnosing", "diagnosis", etc., encompass, with respect to a particular disease or condition, the initial detection of the disease; the characterization or classification of the disease; the detection of the progression, remission, or recurrence of the disease; and the detection of disease response after the administration of a treatment or therapy to the individual. The diagnosis of pancreatic cancer includes distinguishing individuals who have cancer from individuals who do not.

As used herein, "prognose", "prognosing", "prognosis", and variations thereof refer to the prediction of a future course of a disease or condition in an individual who has the disease or condition (e.g., predicting patient survival), and such terms encompass the evaluation of disease response after the administration of a treatment or therapy to the individual.

In additional embodiments, the methods of determining probability for early stage PDAC in an individual further encompass detecting a measurable feature for one or more risk indicia associated with PDAC including, for example, age, obesity (body mass index), history of smoking/tobacco use, history of chronic pancreatitis, history of diabetes, family history of pancreatic cancer, history of intraductal papillary mucinous neoplasm or pancreatic intraepithelial neoplasia, history of mutations in cyclin-dependent kinase inhibitor 2A (CDKN2A), breast cancer 1, early onset BRCA1), breast cancer 2, early onset (BRCA2), serine/threonine kinase 11 (STK11), mutS homolog 2, colon cancer, nonpolyposis type 1 (*E. coli*) (MSH2), mutL homolog 1, colon cancer, nonpolyposis type 2 (*E. coli*) (MLH1), adenomatous polyposis coli (APC), partner and localizer of BRCA2 (PALB2), protease, serine, 1 (trypsin 1) (PRSS1), serine peptidase inhibitor, Kazal type 1 (SPINK1) genes. In additional embodiments the risk indicia include, but are not limited to, age, sex, race, diet, history of previous pancreatic cancer, presence of hereditary pancreatic cancer syndrome (e.g., BRCA2 mutation, familial atypical multiple mole melanoma, Peutz-Jeghers Syndrome, hereditary pancreatitis), genetic (e.g., familial pancreatic cancer) considerations, and environmental exposure. In some embodiments, the individuals at risk for pancreatic cancer include, e.g., those having at least 2 first-degree relatives who have experienced pancreatic cancer without accumulation of other cancers or familial diseases, and those whose risk is determined by analysis of genetic or biochemical markers (e.g., BRCA2, p16, STK11/LKB1, or PRSS1 gene). A "measurable feature" is any property, characteristic or aspect that can be determined and correlated with the probability for early stage PDAC in an individual. For a biomarker, such a measurable feature can include, for example, the presence, absence, or concentration of the biomarker, or a fragment thereof, in the biological sample, an altered structure, such as, for example, the presence or amount of a post-translational modification, such as oxidation at one or more positions on the amino acid sequence of the biomarker or, for example, the presence of an altered conformation in comparison to the conformation of the biomarker in normal control subjects, and/or the presence, amount, or altered structure of the biomarker as a part of a profile of more than one biomarker. In addition to biomarkers, measurable features can further include risk indicia including, for example, age, sex, race, diet, history of previous pancreatic cancer, presence of hereditary pancreatic cancer syndrome (e.g., BRCA2 mutation, familial atypical multiple mole melanoma, Peutz-Jeghers Syndrome, hereditary pancreatitis), genetic (e.g., familial pancreatic cancer) considerations, and environmental exposure.

In some embodiments of the disclosed methods of determining probability for early stage PDAC in an individual is calculated based on the quantified amount of each of N biomarkers selected from the biomarkers listed in Tables 1 through 4. In some embodiments, the disclosed methods for determining the probability of early stage PDAC encompass detecting and/or quantifying one or more biomarkers using mass spectrometry, a capture agent or a combination thereof.

In some embodiments, the disclosed methods of determining probability for early stage PDAC in an individual encompass an initial step of providing a biomarker panel comprising N of the biomarkers listed in Tables 1 through 4. In additional embodiments, the disclosed methods of determining probability for early stage PDAC in an individual encompass an initial step of providing a biological sample from the individual.

In some embodiments, the disclosed methods of determining probability for PDAC in an individual encompass communicating the probability to a health care provider. As stated above, although described and exemplified with reference to determining probability for early stage PDAC in an individual, all embodiments described throughout this disclosure are similarly applicable to the methods of predicting early stage PDAC in an individual. It will be apparent to one skilled in the art that each of the aforementioned methods have specific and substantial utilities and benefits with regard to these related conditions.

In additional embodiments, the communication informs a subsequent treatment decision for the individual. In some embodiments, the method of determining probability for early stage PDAC in an individual encompasses the additional feature of expressing the probability as a risk score.

As used herein, the term "risk score" refers to a score that can be assigned based on comparing the amount of one or more biomarkers in a biological sample obtained from a individual to a standard or reference score that represents an average amount of the one or more biomarkers calculated from biological samples obtained from a random pool of individuals. A standard or reference score can be predetermined and built into a predictor model such that the comparison is indirect rather than actually performed every time the probability is determined for an individual. A risk score can be a standard (e.g., a number) or a threshold (e.g., a line on a graph). The value of the risk score correlates to the deviation, upwards or downwards, from the average amount of the one or more biomarkers calculated from biological samples obtained from a random pool of healthy individuals. In certain embodiments, if a risk score is greater than a standard or reference risk score, the individual can have an increased likelihood of early stage PDAC. In some embodiments, the magnitude of an individual's risk score, or the amount by which it exceeds a reference risk score, can be indicative of or correlated to that individual's level of risk.

In the context of the present invention, the term "biological sample," encompasses any sample that is taken from an individual and contains one or more of the biomarkers listed in Tables 1 through 4. Suitable samples in the context of the present invention include, for example, blood, plasma, serum, saliva, and urine. In some embodiments, the biological sample is selected from the group consisting of whole blood, plasma, and serum. In a particular embodiment, the biological sample is serum. As will be appreciated by those skilled in the art, a biological sample can include any fraction or component of blood, without limitation, T cells, monocytes, neutrophils, erythrocytes, platelets, circulating tumor cells, cell free DNA (cfDNA) and microvesicles such as exosomes and exosome-like vesicles Pancreatic cancer is a malignant neoplasm of the pancreas. About 95% of exocrine pancreatic cancers are pancreatic ductal adenocarcinomas (PDACs), also referred to as pancreatic adenocarcinomas (PAC). The remaining 5% include adenosquamous carcinomas, signet ring cell carcinomas, hepatoid carcinomas, colloid carcinomas, undifferentiated carcinomas, and undifferentiated carcinomas with osteoclast-like giant cells. Exocrine pancreatic tumors are far more common than pancreatic endocrine tumors, which make up about 1% of total cases.

In some embodiments, the pancreatic cancer is exocrine pancreatic cancer or endocrine pancreatic cancer. The exocrine pancreatic cancer includes, but is not limited to, adenocarcinomas, acinar cell carcinomas, adenosquamous carcinomas, colloid carcinomas, undifferentiated carcinomas with osteoclast-like giant cells, hepatoid carcinomas, intraductal papillary-mucinous neoplasms, mucinous cystic neoplasms, pancreatoblastomas, serous cystadenomas, signet ring cell carcinomas, solid and pseuodpapillary tumors, pancreatic ductal carcinomas, and undifferentiated carcinomas. In some embodiments, the exocrine pancreatic cancer is pancreatic ductal carcinoma.

The endocrine pancreatic cancer includes, but is not limited to, insulinomas and glucagonomas.

In some embodiments, the pancreatic cancer is early stage pancreatic cancer, non-metastatic pancreatic cancer, primary pancreatic cancer, advanced pancreatic cancer, locally advanced pancreatic cancer, metastatic pancreatic cancer, unresectable pancreatic cancer, pancreatic cancer in remission, or recurrent pancreatic cancer. In some embodiments, the pancreatic cancer is locally advanced pancreatic cancer, unresectable pancreatic cancer, or metastatic pancreatic ductal carcinoma. In some embodiments, the pancreatic cancer is resectable (i.e., tumors that are confined to a portion of the pancreas or has spread just beyond it that allows for complete surgical removal), or locally advanced (unresectable) (i.e., the localized tumors may be unresectable because of local vessel impingement or invasion by tumor). In some embodiments, the pancreatic cancer is, according to American Joint Committee on Cancer (AJCC) tumor-node-metastasis (TNM) classifications, a stage 0 tumor (the tumor is confined to the top layers of pancreatic duct cells and has not invaded deeper tissues, and it has not spread outside of the pancreas (e.g., pancreatic carcinoma in situ or pancreatic intraepithelial neoplasia III), a stage IA tumor (the tumor is confined to the pancreas and is less than 2 cm in size, and it has not spread to nearby lymph nodes or distinct sites), a stage D3 tumor (the tumor is confined to the pancreas and is larger than 2 cm in size, and it has not spread to nearby lymph nodes or distant sites), a stage IIA tumor (the tumor is growing outside the pancreas but not into large blood vessels, and it has not spread to nearby lymph nodes or distant sites), stage IIB (the tumor is either confined to the pancreas or growing outside the pancreas but not into nearby large blood vessels or major nerves, and it has spread to nearby lymph nodes but not distant sites), stage III (the tumor is growing outside the pancreas into nearby large blood vessels or major nerves, and it may or may not have spread to nearby lymph nodes. It has not spread to distant sites) or stage IV tumor (the cancer has spread to distant sites).

Traditional intervention options that can be considered based on the performance of the methods disclosed herein include, for example, alone or in combination, prophylactic anticoagulants, resection with curative intent, neoadjuvant chemotherapy or chemoradiation therapy, palliative resection or biliary decompression, palliative chemotherapy, or palliative chemoradiation therapy.

Surveillance options that can be considered in combination with the performance of the methods disclosed herein include, for example, alone or in combination, endoscopic ultrasound, endoscopic ultrasound-directed biopsy, endoscopic retrograde cholangiopancreatography, endoscopic retrograde cholangiopancreatography-directed ductal brushings or biopsy, imaging by MRI or CT.

The term "amount" or "level" as used herein refers to a quantity of a biomarker that is detectable or measurable in a biological sample and/or control. The quantity of a biomarker can be, for example, a quantity of polypeptide, the quantity of nucleic acid, or the quantity of a fragment or surrogate. The term can alternatively include combinations thereof. The term "amount" or "level" of a biomarker is a measurable feature of that biomarker.

In some embodiments, calculating the probability for early stage PDAC in an individual is based on the quantified amount of each of N biomarkers selected from the biomarkers listed in Tables 1 through 4. Any existing, available or conventional separation, detection and quantification methods can be used herein to measure the presence or absence (e.g., readout being present vs. absent; or detectable amount vs. undetectable amount) and/or quantity (e.g., readout being an absolute or relative quantity, such as, for example, absolute or relative concentration) of biomarkers, including nucleic acids, peptides, polypeptides, proteins and/or fragments thereof and optionally of the one or more other biomarkers or fragments thereof in samples. In some embodiments, detection and/or quantification of one or more biomarkers comprises an assay that utilizes a capture agent. In further embodiments, the capture agent is an antibody, antibody fragment, nucleic acid-based protein binding reagent, small molecule or variant thereof. In additional embodiments, the assay is an immunoassay such as enzyme immunoassay (EIA), enzyme-linked immunosorbent assay (ELISA), and radioimmunoassay (RIA). In some embodiments, detection and/or quantification of one or more biomarkers further comprises mass spectrometry (MS). In yet further embodiments, the mass spectrometry is co-immunoprecipitation-mass spectrometry (co-IP MS), where coimmunoprecipitation, a technique suitable for the isolation of whole protein complexes is followed by mass spectrometric analysis.

Generally, any mass spectrometric (MS) technique that can provide precise information on the mass of peptides, and preferably also on fragmentation and/or (partial) amino acid sequence of selected peptides (e.g., in tandem mass spectrometry, MS/MS; or in post source decay, TOF MS), can be used in the methods disclosed herein. Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000; Biemann 1990. Methods Enzymol 193: 455-79; or Methods in Enzymology, vol. 402: "Biological Mass Spectrometry", by Burlingame, ed., Academic Press 2005) and can be used in practicing the methods disclosed herein. Accordingly, in some embodiments, the disclosed methods comprise performing quantitative MS to measure one or more biomarkers. Such quantitiative methods can be performed in an automated (Villanueva, et al., Nature Protocols (2006) 1(2):880-891) or semi-automated format. In particular embodiments, MS can be operably linked to a liquid chromatography device (LC-MS/MS or LC-MS) or gas chromatography device (GC-MS or GC-MS/MS). Other methods useful in this context include isotope-coded affinity tag (ICAT), tandem mass tags (TMT), or stable isotope labeling by amino acids in cell culture (SILAC), followed by chromatography and MS/MS.

As used herein, the terms "multiple reaction monitoring (MRM)" or "selected reaction monitoring (SRM)" refer to an MS-based quantification method that is particularly useful for quantifying analytes that are in low abundance. In an SRM experiment, a predefined precursor ion and one or more of its fragments are selected by the two mass filters of a triple quadrupole instrument and monitored over time for precise quantification. Multiple SRM precursor and fragment ion pairs can be measured within the same experiment on the chromatographic time scale by rapidly toggling between the different precursor/fragment pairs to perform an MRM experiment. A series of transitions (precursor/fragment ion pairs) in combination with the retention time of the targeted analyte (e.g., peptide or small molecule such as chemical entity, steroid, hormone) can constitute a definitive assay. A large number of analytes can be quantified during a single LC-MS experiment. The term "scheduled," or "dynamic" in reference to MRM or SRM, refers to a variation of the assay wherein the transitions for a particular analyte are only acquired in a time window around the expected retention time, significantly increasing the number of analytes that can be detected and quantified in a single LC-MS experiment and contributing to the selectivity of the test, as retention time is a property dependent on the physical nature of the analyte. A single analyte can also be monitored with more than one transition. Finally, included in the assay can be standards that correspond to the analytes of interest (e.g., same amino acid sequence), but differ by the inclusion of stable isotopes. Stable isotopic standards (SIS) can be incorporated into the assay at precise levels and used to quantify the corresponding unknown analyte. An additional level of specificity is contributed by the co-elution of the unknown analyte and its corresponding SIS and properties of their transitions (e.g., the similarity in the ratio of the level of two transitions of the unknown and the ratio of the two transitions of its corresponding SIS).

Mass spectrometry assays, instruments and systems suitable for biomarker peptide analysis can include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)$_n$ (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)$_n$; ion mobility spectrometry (IMS); inductively coupled plasma mass spectrometry (ICP-MS) atmospheric pressure photoionization mass spectrometry (APPI-MS); APPI-MS/MS; and APPI-(MS). Peptide ion fragmentation in tandem MS (MS/MS) arrangements can be achieved using manners established in the art, such as, e.g., collision induced dissociation (CID). As described herein, detection and quantification of biomarkers by mass spectrometry can involve multiple reaction monitoring (MRM), such as described among others by Kuhn et al. *Proteomics* 4: 1175-86 (2004). Scheduled multiple-reaction-monitoring (Scheduled MRM) mode acquisition during LC-MS/MS analysis enhances the sensitivity and accuracy of peptide quantitation. Anderson and Hunter, *Molecular and Cellular Proteomics* 5(4):573 (2006). As described herein, mass spectrometry-based assays can be advantageously combined with upstream peptide or protein separation or fractionation methods, such as for example with the chromatographic, immunoprecipitation, and other methods described herein below. As further described herein, shotgun quantitative proteomics can be combined with SRM/MRM-based assays for high-throughput identification and verification of prognostic biomarkers of early stage PDAC.

A person skilled in the art will appreciate that a number of methods can be used to determine the amount of a biomarker, including mass spectrometry approaches, such as MS/MS, LC-MS/MS, multiple reaction monitoring (MRM) or SRM and product-ion monitoring (PIM) and also including antibody based methods such as immunoassays such as Western blots, enzyme-linked immunosorbant assay (ELISA), immunopercipitation, immunohistochemistry, immunofluorescence, radioimmunoassay, dot blotting, and FACS. Accordingly, in some embodiments, determining the level of the at least one biomarker comprises using an immunoassay and/or mass spectrometric methods. In additional embodiments, the mass spectrometric methods are selected from MS, MS/MS, LC-MS/MS, SRM, PIM, and other such methods that are known in the art. In other embodiments, LC-MS/MS further comprises 1D LC-MS/MS, 2D LC-MS/MS or 3D LC-MS/MS. Immunoassay techniques and protocols are generally known to those skilled in the art (Price and Newman, *Principles and Practice of Immunoassay,* 2nd Edition, Grove's Dictionaries, 1997; and Gosling, *Immunoassays: A Practical Approach,* Oxford University Press, 2000.) A variety of immunoassay techniques, including competitive and non-competitive immunoassays, can be used (Self et al., *Curr. Opin. Biotechnol.,* 7:60-65 (1996).

In further embodiments, the immunoassay is selected from Western blot, ELISA, immunoprecipitation, immunohistochemistry, immunofluorescence, radioimmunoassay (RIA), dot blotting, and FACS. In certain embodiments, the immunoassay is an ELISA. In yet a further embodiment, the ELISA is direct ELISA (enzyme-linked immunosorbent assay), indirect ELISA, sandwich ELISA, competitive ELISA, multiplex ELISA, ELISPOT technologies, and other similar techniques known in the art. Principles of these immunoassay methods are known in the art, for example John R. Crowther, *The ELISA Guidebook,* 1st ed., Humana Press 2000, ISBN 0896037282. Typically ELISAs are performed with antibodies but they can be performed with any capture agents that bind specifically to one or more biomarkers of the invention and that can be detected. Multiplex ELISA allows simultaneous detection of two or more analytes within a single compartment (e.g., microplate well) usually at a plurality of array addresses (Nielsen and Geierstanger 2004. *J Immunol Methods* 290: 107-20 (2004) and Ling et al. 2007. *Expert Rev Mol Diagn* 7: 87-98 (2007)).

In some embodiments, Radioimmunoassay (RIA) can be used to detect one or more biomarkers in the methods of the invention. RIA is a competition-based assay that is well known in the art and involves mixing known quantities of radioactavely-labelled (e.g., $^{125}$I or $^{131}$I-labelled) target analyte with antibody specific for the analyte, then adding non-labelled analyte from a sample and measuring the amount of labelled analyte that is displaced (see, e.g., *An Introduction to Radioimmunoassay and Related Techniques,* by Chard T, ed., Elsevier Science 1995, ISBN 0444821198 for guidance).

A detectable label can be used in the assays described herein for direct or indirect detection of the biomarkers in the methods of the invention. A wide variety of detectable labels can be used, with the choice of label depending on the sensitivity required, ease of conjugation with the antibody, stability requirements, and available instrumentation and disposal provisions. Those skilled in the art are familiar with selection of a suitable detectable label based on the assay detection of the biomarkers in the methods of the invention. Suitable detectable labels include, but are not limited to, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), enzymes (e.g., luciferase, horseradish peroxidase, alkaline phosphatase, etc.), nanoparticles, biotin, digoxigenin, metals, and the like.

For mass-sectrometry based analysis, differential tagging with isotopic reagents, e.g., isotope-coded affinity tags (ICAT) or the more recent variation that uses isobaric tagging reagents, iTRAQ (Applied Biosystems, Foster City, Calif.), or tandem mass tags, TMT, (Thermo Scientific, Rockford, Ill.), followed by multidimensional liquid chromatography (LC) and tandem mass spectrometry (MS/MS) analysis can provide a further methodology in practicing the methods of the invention.

A chemiluminescence assay using a chemiluminescent antibody can be used for sensitive, non-radioactive detection of protein levels. An antibody labeled with fluorochrome also can be suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), beta-galactosidase, urease, and the like. Detection systems using suitable substrates for horseradish-peroxidase, alkaline phosphatase, beta-galactosidase are well known in the art.

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, assays used to practice the invention can be automated or performed robotically, and the signal from multiple samples can be detected simultaneously.

As described above, chromatography can also be used in practicing the methods of the invention. Chromatography encompasses methods for separating chemical substances and generally involves a process in which a mixture of analytes is carried by a moving stream of liquid or gas ("mobile phase") and separated into components as a result of differential distribution of the analytes as they flow around or over a stationary liquid or solid phase ("stationary phase"), between the mobile phase and said stationary phase. The stationary phase can be usually a finely divided solid, a sheet of filter material, or a thin film of a liquid on the surface of a solid, or the like. Chromatography is well understood by those skilled in the art as a technique applicable for the separation of chemical compounds of biological origin, such as, e.g., amino acids, proteins, fragments of proteins or peptides, etc.

Chromatography can be columnar (i.e., wherein the stationary phase is deposited or packed in a column), preferably liquid chromatography, and yet more preferably high-performance liquid chromatography (HPLC), or ultra high performance/pressure liquid chromatography (UHPLC). Particulars of chromatography are well known in the art (Bidlingmeyer, Practical HPLC Methodology and Applications, John Wiley & Sons Inc., 1993). Exemplary types of chromatography include, without limitation, high-performance liquid chromatography (HPLC), UHPLC, normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immuno-affinity, immobilised metal affinity chromatography, and the like. Chromatography, including single-, two- or more-dimensional chromatography, can be used as a peptide fractionation method in conjunction with a further peptide analysis method, such as for example, with a downstream mass spectrometry analysis as described elsewhere in this specification.

In the context of the invention, the term "capture agent" refers to a compound that can specifically bind to a target, in particular a biomarker. The term includes antibodies, antibody fragments, nucleic acid-based protein binding reagents (e.g. aptamers, Slow Off-rate Modified Aptamers (SOMAmer™)), protein-capture agents, natural ligands (i.e. a hormone for its receptor or vice versa), small molecules or variants thereof.

Capture agents can be configured to specifically bind to a target, in particular a biomarker. Capture agents can include but are not limited to organic molecules, such as polypeptides, polynucleotides and other non polymeric molecules that are identifiable to a skilled person. In the embodiments disclosed herein, capture agents include any agent that can be used to detect, purify, isolate, or enrich a target, in particular a biomarker. Any art-known affinity capture technologies can be used to selectively isolate and enrich/concentrate biomarkers that are components of complex mixtures of biological media for use in the disclosed methods.

Antibody capture agents that specifically bind to a biomarker can be prepared using any suitable methods known in the art. See, e.g., Coligan, *Current Protocols in Immunology* (1991); Harlow & Lane, *Antibodies: A Laboratory Manual* (1988); Goding, *Monoclonal Antibodies: Principles and Practice* (2d ed. 1986). Antibody capture agents can be any immunoglobulin or derivative thereof, whether natural or wholly or partially synthetically produced. All derivatives thereof which maintain specific binding ability are also included in the term. Antibody capture agents have a binding domain that is homologous or largely homologous to an immunoglobulin binding domain and can be derived from natural sources, or partly or wholly synthetically produced. Antibody capture agents can be monoclonal or polyclonal antibodies. In some embodiments, an antibody is a single chain antibody. Those of ordinary skill in the art will appreciate that antibodies can be provided in any of a variety of forms including, for example, humanized, partially humanized, chimeric, chimeric humanized, etc. Antibody capture agents can be antibody fragments including, but not limited to, Fab, Fab', F(ab')2, scFv, Fv, dsFv diabody, and Fd fragments. An antibody capture agent can be produced by any means. For example, an antibody capture agent can be enzymatically or chemically produced by fragmentation of an intact antibody and/or it can be recombinantly produced from a gene encoding the partial antibody sequence. An antibody capture agent can comprise a single chain antibody fragment. Alternatively or additionally, antibody capture agent can comprise multiple chains which are linked together, for example, by disulfide linkages; and, any functional fragments obtained from such molecules, wherein such fragments retain specific-binding properties of the parent antibody molecule. Because of their smaller size as functional components of the whole molecule, antibody fragments can offer advantages over intact antibodies for use in certain immunochemical techniques and experimental applications.

Suitable capture agents useful for practicing the invention also include aptamers. Aptamers are oligonucleotide sequences that can bind to their targets specifically via unique three dimensional (3-D) structures. An aptamer can include any suitable number of nucleotides and different aptamers can have either the same or different numbers of nucleotides. Aptamers can be DNA or RNA or chemically modified nucleic acids and can be single stranded, double stranded, or contain double stranded regions, and can include higher ordered structures. An aptamer can also be a photoaptamer, where a photoreactive or chemically reactive functional group is included in the aptamer to allow it to be covalently linked to its corresponding target. Use of an aptamer capture agent can include the use of two or more aptamers that specifically bind the same biomarker. An aptamer can include a tag. An aptamer can be identified using any known method, including the SELEX (systematic evolution of ligands by exponential enrichment), process. Once identified, an aptamer can be prepared or synthesized in accordance with any known method, including chemical synthetic methods and enzymatic synthetic methods and used in a variety of applications for biomarker detection. Liu et al., *Curr Med Chem.* 18(27):4117-25 (2011). Capture agents useful in practicing the methods of the invention also include SOMAmers (Slow Off-Rate Modified Aptamers) known in the art to have improved off-rate characteristics. Brody et al., *J Mol Biol.* 422(5):595-606 (2012). SOMAmers can be generated using using any known method, including the SELEX method.

It is understood by those skilled in the art that biomarkers can be modified prior to analysis to improve their resolution or to determine their identity. For example, the biomarkers can be subject to proteolytic digestion before analysis. Any protease can be used. Proteases, such as trypsin, that are likely to cleave the biomarkers into a discrete number of fragments are particularly useful. The fragments that result from digestion function as a fingerprint for the biomarkers, thereby enabling their detection indirectly. This is particularly useful where there are biomarkers with similar molecular masses that might be confused for the biomarker in question. Also, proteolytic fragmentation is useful for high molecular weight biomarkers because smaller biomarkers are more easily resolved by mass spectrometry. In another example, biomarkers can be modified to improve detection resolution. For instance, neuraminidase can be used to remove terminal sialic acid residues from glycoproteins to improve binding to an anionic adsorbent and to improve detection resolution. In another example, the biomarkers can be modified by the attachment of a tag of particular molecular weight that specifically binds to molecular biomarkers, further distinguishing them. Optionally, after detecting such modified biomarkers, the identity of the biomarkers can be further determined by matching the physical and chemical characteristics of the modified biomarkers in a protein database (e.g., SwissProt).

It is further appreciated in the art that biomarkers in a sample can be captured on a substrate for detection. Traditional substrates include antibody-coated 96-well plates or nitrocellulose membranes that are subsequently probed for the presence of the proteins. Alternatively, protein-binding molecules attached to microspheres, microparticles, microbeads, beads, or other particles can be used for capture and detection of biomarkers. The protein-binding molecules can be antibodies, peptides, peptoids, aptamers, small molecule ligands or other protein-binding capture agents attached to the surface of particles. Each protein-binding molecule can include unique detectable label that is coded such that it can be distinguished from other detectable labels attached to other protein-binding molecules to allow detection of biomarkers in multiplex assays. Examples include, but are not limited to, color-coded microspheres with known fluorescent light intensities (see e.g., microspheres with xMAP technology produced by Luminex (Austin, Tex.); microspheres containing quantum dot nanocrystals, for example, having different ratios and combinations of quantum dot colors (e.g., Qdot nanocrystals produced by Life Technologies (Carlsbad, Calif.); glass coated metal nanoparticles (see e.g., SERS nanotags produced by Nanoplex Technologies, Inc. (Mountain View, Calif.); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), glass microparticles with digital holographic code images (see e.g., CyVera microbeads produced by Illumina (San Diego, Calif.); chemiluminescent dyes, combinations of dye compounds; and beads of detectably different sizes.

In another aspect, biochips can be used for capture and detection of the biomarkers of the invention. Many protein biochips are known in the art. These include, for example, protein biochips produced by Packard BioScience Company (Meriden Conn.), Zyomyx (Hayward, Calif.) and Phylos (Lexington, Mass.). In general, protein biochips comprise a substrate having a surface. A capture reagent or adsorbent is attached to the surface of the substrate. Frequently, the surface comprises a plurality of addressable locations, each of which location has the capture agent bound there. The capture agent can be a biological molecule, such as a polypeptide or a nucleic acid, which captures other biomarkers in a specific manner. Alternatively, the capture agent can be a chromatographic material, such as an anion exchange material or a hydrophilic material. Examples of protein biochips are well known in the art.

Measuring mRNA in a biological sample can be used as a surrogate for detection of the level of the corresponding protein biomarker in a biological sample. Thus, any of the biomarkers or biomarker panels described herein can also be detected by detecting the appropriate RNA. Levels of mRNA can be measured by reverse transcription quantitative polymerase chain reaction (RT-PCR followed with qPCR). RT-PCR is used to create a cDNA from the mRNA. The cDNA can be used in a qPCR assay to produce fluorescence as the DNA amplification process progresses. By comparison to a standard curve, qPCR can produce an absolute measurement such as number of copies of mRNA per cell. Northern blots, microarrays, Invader assays, and RT-PCR combined with capillary electrophoresis have all been used to measure expression levels of mRNA in a sample. See *Gene Expression Profiling: Methods and Protocols*, Richard A. Shimkets, editor, Humana Press, 2004.

As described herein, in some embodiments the biomarkers of the invention encompass one or more RNAs. The RNA isolated from the sample may be total RNA, mRNA, microRNA, tRNA, rRNA or any type of RNA. In particular embodiments, the biomarkers of the invention encompass one or more miRNAs selected from the group consisting of miR-100a, miR-1290, miR-155, miR-18a, miR-196a, miR-21, miR-210, miR-221, miR-24, miR-31, miR-375, and miR-885.

Conventional methods and reagents for isolating RNA from a sample comprise High Pure miRNA Isolation Kit (Roche), Trizol (Invitrogen), Guanidinium thiocyanate-phenol-chloroform extraction, PureLinkTM miRNA isolation kit (Invitrogen), PureLink Micro-to-Midi Total RNA Purification System (invitrogen), RNeasy kit (Qiagen), miRNeasy kit (Qiagen), Oligotex kit (Qiagen), phenol extraction, phenol-chloroform extraction, TCA/acetone precipitation, ethanol precipitation, Column purification, Silica gel membrane purification, PureYieldTM RNA Midiprep (Promega), PolyATtract System 1000 (Promega), Maxwell™ 16 System (Promega), SV Total RNA Isolation (Promega), geneMAG-RNA/DNA kit (Chemicell), TRI Reagent™ (Ambion), RNAqueous Kit (Ambion), ToTALLY RNA™ Kit (Ambion), Poly(A)Purist™ Kit (Ambion) and any other methods, commercially available or not, known to the skilled person. If the sample is a FFPE, the tissue sections are initially deparaffinised, such as in xylene and ethanol.

The RNA may be further amplified, cleaned-up, concentrated, DNase treated, quantified or otherwise analysed or examined such as by agarose gel electrophoresis, absorbance spectrometry or Bioanalyser analysis (Agilent) or subjected to any other post-extraction method known to the skilled person.

Methods for extracting and analysing an RNA sample are disclosed in Molecular Cloning, A Laboratory Manual (Sambrook and Russell (ed.), $3^{rd}$ edition (2001), Cold Spring Harbor Laboratory Press, Cold Spring Harbor, N.Y., USA.

The isolated RNA may be analysed by quantitative ("real-time") PCR (QPCR). In one embodiment, the expression level of one or more miRNAs is determined by the quantitative polymerase chain reaction (QPCR) technique. Real-time polymerase chain reaction, also called quantitative polymerase chain reaction (Q-PCR/qPCR/RT-QPCR) or kinetic polymerase chain reaction, is a technique based on the polymerase chain reaction, which is used to amplify and simultaneously quantify a targeted DNA molecule. It enables both detection and quantification (as absolute number of copies or relative amount when normalized to DNA input or additional normalizing genes) of a specific sequence in a DNA sample.

The procedure follows the general principle of polymerase chain reaction; its key feature is that the amplified DNA is quantified as it accumulates in the reaction in real time after each amplification cycle. Two common methods of quantification are the use of fluorescent dyes that intercalate with double-stranded DNA, and modified DNA oligonucleotide probes that fluoresce when hybridized with a complementary DNA. Frequently, real-time polymerase chain reaction is combined with reverse transcription polymerase chain reaction to quantify low abundance messenger RNA (mRNA), or miRNA, enabling a researcher to quantify relative gene expression at a particular time, or in a particular cell or tissue type.

In a real time PCR assay a positive reaction is detected by accumulation of a fluorescent signal. The Ct (cycle threshold) is defined as the number of cycles required for the fluorescent signal to cross the threshold (i.e. exceeds background level). Ct levels are inversely proportional to the amount of target nucleic acid in the sample (i.e. the lower the Ct level the greater the amount of target nucleic acid in the sample). Most real time assays undergo 40 cycles of amplification. The QPCR may be performed using chemicals and/or machines from a commercially available platform.

The QPCR may be performed using QPCR machines from any commercially available platform; such as Prism, geneAmp or StepOne Real Time PCR systems (Applied Biosystems), LightCycler (Roche), RapidCycler (Idaho Technology), MasterCycler (Eppendorf), iCycler iQ system, Chromo 4 system, CFX, MiniOpticon and Opticon systems (Bio-Rad), SmartCycler system (Cepheid), RotorGene system (Corbett Lifescience), MX3000 and MX3005 systems (Stratagene), DNA Engine Opticon system (Qiagen), Quantica qPCR systems (Techne), InSyte and Syncrom cycler system (BioGene), DT-322 (DNA Technology), Exicycler Notebook Thermal cycler, TL998 System (lanlong), Line-Gene-K systems (Bioer Technology), or any other commercially available platform.

The QPCR may be performed using chemicals from any commercially available platform, such as NCode EXPRESS qPCR or EXPRESS qPCR (Invitrogen), Taqman or SYBR green qPCR systems (Applied Biosystems), Real-Time PCR reagents (Eurogentec), iTaq mix (Bio-Rad), qPCR mixes and kits (Biosense), and any other chemicals, commercially available or not, known to the skilled person. The QPCR reagents and detection system may be probe-based, or may be based on chelating a fluorescent chemical into double-stranded oligonucleotides. The QPCR reaction may be performed in a tube; such as a single tube, a tube strip or a plate, or it may be performed in a microfluidic card in which the relevant probes and/or primers are already integrated.

A Microfluidic card allows high throughput, parallel analysis of mRNA or miRNA expression patterns, and allows for a quick and cost-effective investigation of biological pathways. The microfluidic card may be a piece of plastic that is riddled with micro channels and chambers filled with the appropriate probes. A sample in fluid form is injected into one end of the card, and capillary action causes the fluid sample to be distributed into the microchannels. The microfluidic card is then placed in an appropriate device for processing the card and reading the signal.

Any commercially available (predesigned or custom-made) microfluidic card, for example, TaqMan™ Array Human MicroRNA A+B Cards V2.0 (Applied Biosystems) can be used. Said microfluidic card may comprise a number of probes and/or primers for analysing the expression of a number of miRNAs, such as between 1-10 miRNAs, for example 10-20 miRNA, such as between 20-30 miRNAs, for example 30-40 miRNA, such as between 40-50 miRNAs, for example 50-100 miRNA, such as between 100-200 miRNAs, for example 200-300 miRNA, such as between 300-400 miRNAs, for example 400-500 miRNA, such as between 500-1000 miRNAs.

The isolated RNA may be analysed by microarray analysis. In one embodiment, the expression level of one or more miRNAs is determined by the microarray technique. A microarray is a multiplex technology that consists of an arrayed series of thousands of microscopic spots of DNA oligonucleotides or antisense miRNA probes, called features, each containing picomoles of a specific oligonucleotide sequence. This can be a short section of a gene or other DNA or RNA element that are used as probes to hybridize a DNA or RNA sample (called target) under high-stringency conditions. Probe-target hybridization is usually detected and quantified by fluorescence-based detection of fluorophore-labeled targets to determine relative abundance of nucleic acid sequences in the target. In standard microarrays, the probes are attached to a solid surface by a covalent bond to a chemical matrix (via epoxy-silane, amino-silane, lysine, polyacrylamide or others). The solid surface can be glass or a silicon chip, in which case they are commonly known as gene chip. DNA arrays are so named because they either measure DNA or use DNA as part of its detection system. The DNA probe may however be a modified DNA structure such as LNA (locked nucleic acid).

In some embodiments, the microarray analysis is used to detect microRNA, known as microRNA or miRNA expression profiling. The microarray for detection of microRNA may be a microarray platform, wherein the probes of the microarray may be comprised of antisense miRNAs or DNA oligonucleotides. In the first case, the target is a labelled sense miRNA sequence, and in the latter case the miRNA has been reverse transcribed into cDNA and labelled. The microarray for detection of microRNA may be a commercially available array platform, such as NCode™ miRNA Microarray Expression Profiling (Invitrogen), miRCURY LNA™ microRNA Arrays (Exiqon), microRNA Array (Agilent), µParaflo™Microfluidic Biochip Technology (LC Sciences), MicroRNA Profiling Panels (Illumina), Geniom™ Biochips (Febit Inc.), microRNA Array (Oxford Gene Technology), Custom AdmiRNA™ profiling service (Applied Biological Materials Inc.), microRNA Array (Dharmacon-Thermo Scientific), LDA TaqMan analyses (Applied Biosystems), Taqman microRNA Array (Applied Biosystems) or any other commercially available array. Microarray analysis may comprise all or a subset of the steps of RNA isolation, RNA amplification, reverse transcription, target labelling, hybridisation onto a microarray chip, image analysis and normalisation, and subsequent data analysis; each of these steps may be performed according to a manufacturers protocol.

It follows, that any of the methods as disclosed herein above e.g. for determining the prognosis of an individual with pancreatic cancer may further comprise one or more of the steps of: i) isolating miRNA from a sample, ii) determining an expression profile of said miRNA in said sample, wherein the miRNA molecules comprise the nucleic acids listed in Table 2, thereby determining the prognosis of pancreatic cancer in said individual. The expression profile can be generated using any method known in the art, including, without limitation, oligonucleotide microarrays, microRNA (miRNA) arrays, and high-throughput sequencing and high throughput quantitative polymerase chain reaction (qPCR).

One skilled in the art will appreciate that isolated RNA may be analyzed by any method known in the art including, for example, northern blotting or nuclease protection assay. Northern blotting combines denaturing agarose gel or polyacrylamide gel electrophoresis for size separation of RNA with methods to transfer the size-separated RNA to a filter membrane for probe hybridization. The hybridization probe may be made from DNA or RNA. Nuclease protection assay is a technique used to identify individual RNA molecules in a heterogeneous RNA sample extracted from cells. The technique can identify one or more RNA molecules of known sequence even at low total concentration. The extracted RNA is first mixed with antisense RNA or DNA probes that are complementary to the sequence or sequences of interest and the complementary strands are hybridized to form double-stranded RNA (or a DNA-RNA hybrid). The mixture is then exposed to ribonucleases that specifically cleave only single-stranded RNA but have no activity against double-stranded RNA. When the reaction runs to completion, susceptible RNA regions are degraded to very short oligomers or to individual nucleotides; the surviving RNA fragments are those that were complementary to the added antisense strand and thus contained the sequence of interest.

Some embodiments disclosed herein relate to diagnostic and prognostic methods of determining the probability for PDAC, chronic pancreatitis, early stage PDAC, late stage PDAC, and other periampullary diseases. The detection of the level of expression of one or more biomarkers and/or the determination of a ratio of biomarkers can be used to determine the probability for each of PDAC, chronic pancreatitis, early stage PDAC, late stage PDAC, and other periampullary diseases. Such detection methods can be used, for example, for early diagnosis of the condition, to determine whether a subject is predisposed to PDAC, chronic pancreatitis, early stage PDAC, late stage PDAC, and other periampullary diseases, to monitor the progress of PDAC, chronic pancreatitis, early stage PDAC, late stage PDAC, and other periampullary diseases or the progress of treatment protocols, to assess the severity of PDAC, chronic pancreatitis, early stage PDAC, late stage PDAC, and other periampullary diseases, to forecast the outcome of PDAC, chronic pancreatitis, early stage PDAC, late stage PDAC, and other periampullary diseases and/or prospects of recovery, or to aid in the determination of a suitable treatment for PDAC, chronic pancreatitis, early stage PDAC, late stage PDAC, and other periampullary diseases. In some embodiments, the methods disclosed herein can be performed to determine the probability of a response to a particular treatment in an individual. In other embodiments, the methods disclosed herein can be performed to determine the probability that an individual develops venous thromboembolism. Such suitable treatments include, for example, resection, chemotherapy, and chemoradiation therapy.

In some embodiments disclosed herein, the methods of the invention can be used to determine the probability for survival of an individual diagnosed with of PDAC, chronic pancreatitis, early stage PDAC, late stage PDAC, and other periampullary diseases.

In some embodiments disclosed herein, the methods of the invention can be used to determine the probability for disease recurrence in an individual diagnosed with of PDAC, chronic pancreatitis, early stage PDAC, late stage PDAC, and other periampullary diseases.

The quantitation of biomarkers in a biological sample can be determined, without limitation, by the methods described above as well as any other method known in the art. The quantitative data thus obtained is then subjected to an analytic classification process. In such a process, the raw data is manipulated according to an algorithm, where the algorithm has been pre-defined by a training set of data, for example as described in the examples provided herein. An algorithm can utilize the training set of data provided herein, or can utilize the guidelines provided herein to generate an algorithm with a different set of data.

In some embodiments, analyzing a measurable feature to determine the probability of PDAC, chronic pancreatitis, early stage PDAC, late stage PDAC, and other periampullary diseases encompasses the use of a predictive model. In further embodiments, analyzing a measurable feature to determine the probability for PDAC, chronic pancreatitis, early stage PDAC, late stage PDAC, and other periampullary diseases encompasses comparing said measurable feature with a reference feature. As those skilled in the art can appreciate, such comparison can be a direct comparison to the reference feature or an indirect comparison where the reference feature has been incorporated into the predictive model. In further embodiments, analyzing a measurable feature to determine the probability PDAC, chronic pancreatitis, early stage PDAC, late stage PDAC, and other periampullary diseases encompasses one or more of a linear discriminant analysis model, a support vector machine classification algorithm, a recursive feature elimination model, a prediction analysis of microarray model, a logistic regression model, a CART algorithm, a flex tree algorithm, a LART algorithm, a random forest algorithm, a MART algorithm, a machine learning algorithm, a penalized regression method, or a combination thereof. In particular embodiments, the analysis comprises logistic regression.

An analytic classification process can use any one of a variety of statistical analytic methods to manipulate the quantitative data and provide for classification of the sample. Examples of useful methods include linear discriminant analysis, recursive feature elimination, a prediction analysis of microarray, a logistic regression, a CART algorithm, a FlexTree algorithm, a LART algorithm, a random forest algorithm, a MART algorithm, machine learning algorithms; etc.

Classification can be made according to predictive modeling methods that set a threshold for determining the probability that a sample belongs to a given class. The probability preferably is at least 50%, or at least 60%, or at least 70%, or at least 80% or higher. Classifications also can be made by determining whether a comparison between an obtained dataset and a reference dataset yields a statistically significant difference. If so, then the sample from which the dataset was obtained is classified as not belonging to the reference dataset class. Conversely, if such a comparison is not statistically significantly different from the reference dataset, then the sample from which the dataset was obtained is classified as belonging to the reference dataset class.

The predictive ability of a model can be evaluated according to its ability to provide a quality metric, e.g. AUROC (area under the ROC curve) or accuracy, of a particular value, or range of values. Area under the curve measures are useful for comparing the accuracy of a classifier across the complete data range. Classifiers with a greater AUC have a greater capacity to classify unknowns correctly between two groups of interest. In some embodiments, a desired quality threshold is a predictive model that will classify a sample with an accuracy of at least about 0.5, at least about 0.55, at least about 0.6, at least about 0.7, at least about 0.75, at least about 0.8, at least about 0.85, at least about 0.9, at least about 0.95, or higher. As an alternative measure, a desired quality threshold can refer to a predictive model that will classify a sample with an AUC of at least about 0.7, at least about 0.75, at least about 0.8, at least about 0.85, at least about 0.9, or higher.

As is known in the art, the relative sensitivity and specificity of a predictive model can be adjusted to favor either the selectivity metric or the sensitivity metric, where the two metrics have an inverse relationship. The limits in a model as described above can be adjusted to provide a selected sensitivity or specificity level, depending on the particular requirements of the test being performed. One or both of sensitivity and specificity can be at least about 0.7, at least about 0.75, at least about 0.8, at least about 0.85, at least about 0.9, or higher.

The raw data can be initially analyzed by measuring the values for each biomarker, usually in triplicate or in multiple triplicates. The data can be manipulated, for example, raw data can be transformed using standard curves, and the average of triplicate measurements used to calculate the average and standard deviation for each patient. These values can be transformed before being used in the models, e.g. log-transformed, Box-Cox transformed (Box and Cox, *Royal Stat. Soc.*, Series B, 26:211-246(1964). The data are then input into a predictive model, which will classify the sample according to the state. The resulting information can be communicated to a patient or health care provider.

To generate a predictive model for PDAC, chronic pancreatitis, early stage PDAC, late stage PDAC, and other periampullary diseases, a robust data set, comprising known control samples and samples corresponding to the classification of interest is used in a training set. A sample size can be selected using generally accepted criteria. As discussed above, different statistical methods can be used to obtain a highly accurate predictive model.

In one embodiment, hierarchical clustering is performed in the derivation of a predictive model, where the Pearson correlation is employed as the clustering metric. One approach is to consider a early stage PDAC dataset as a "learning sample" in a problem of "supervised learning." CART is a standard in applications to medicine (Singer, *Recursive Partitioning in the Health Sciences*, Springer (1999)) and can be modified by transforming any qualitative features to quantitative features; sorting them by attained significance levels, evaluated by sample reuse methods for Hotelling's $T^2$ statistic; and suitable application of the lasso method. Problems in prediction are turned into problems in regression without losing sight of prediction, indeed by making suitable use of the Gini criterion for classification in evaluating the quality of regressions.

This approach led to what is termed FlexTree (Huang, *Proc. Nat. Acad. Sci. U.S.A* 101:10529-10534(2004)). Flex-Tree performs very well in simulations and when applied to multiple forms of data and is useful for practicing the claimed methods. Software automating FlexTree has been developed. Alternatively, LARTree or LART can be used (Turnbull (2005) *Classification Trees with Subset Analysis Selection by the Lasso*, Stanford University). The name reflects binary trees, as in CART and FlexTree; the lasso, as has been noted; and the implementation of the lasso through what is termed LARS by Efron et al. (2004) *Annals of Statistics* 32:407-451 (2004). See, also, Huang et al., *Proc. Natl. Acad. Sci. USA.* 101(29):10529-34 (2004). Other methods of analysis that can be used include logic regression. One method of logic regression Ruczinski, *Journal of Computational and Graphical Statistics* 12:475-512 (2003). Logic regression resembles CART in that its classifier can be displayed as a binary tree. It is different in that each node has Boolean statements about features that are more general than the simple "and" statements produced by CART.

Another approach is that of nearest shrunken centroids (Tibshirani, *Proc. Natl. Acad. Sci. U.S.A* 99:6567-72(2002)). The technology is k-means-like, but has the advantage that by shrinking cluster centers, one automatically selects features, as is the case in the lasso, to focus attention on small numbers of those that are informative. The approach is available as PAM software and is widely used. Two further sets of algorithms that can be used are random forests (Breiman, *Machine Learning* 45:5-32 (2001)) and MART (Hastie, *The Elements of Statistical Learning*, Springer (2001)). These two methods are known in the art as "committee methods," that involve predictors that "vote" on outcome.

To provide significance ordering, the false discovery rate (FDR) can be determined. First, a set of null distributions of dissimilarity values is generated. In one embodiment, the values of observed profiles are permuted to create a sequence of distributions of correlation coefficients obtained out of chance, thereby creating an appropriate set of null distributions of correlation coefficients (Tusher et al., *Proc. Natl. Acad. Sci. U.S.A* 98, 5116-21 (2001)). The set of null distribution is obtained by: permuting the values of each profile for all available profiles; calculating the pair-wise correlation coefficients for all profile; calculating the probability density function of the correlation coefficients for this permutation; and repeating the procedure for N times, where N is a large number, usually 300. Using the N distributions, one calculates an appropriate measure (mean, median, etc.) of the count of correlation coefficient values that their values exceed the value (of similarity) that is obtained from the distribution of experimentally observed similarity values at given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value can be applied to the correlations between experimental profiles. Using the aforementioned distribution, a level of confidence is chosen for significance. This is used to determine the lowest value of the correlation coefficient that exceeds the result that would have obtained by chance. Using this method, one obtains thresholds for positive correlation, negative correlation or both. Using this threshold(s), the user can filter the observed values of the pair wise correlation coefficients and eliminate those that do not exceed the threshold(s). Furthermore, an estimate of the false positive rate can be obtained for a given threshold. For each of the individual "random correlation" distributions, one can find how many observations fall outside the threshold range. This procedure provides a sequence of counts. The mean and the standard deviation of the sequence provide the average number of potential false positives and its standard deviation.

In addition the Cox models can be used, especially since reductions of numbers of covariates to manageable size with the lasso will significantly simplify the analysis, allowing the possibility of a nonparametric or semi-parametric approach to prediction of time to early stage PDAC. These statistical tools are known in the art and applicable to all manner of proteomic data. A set of biomarker, clinical and genetic data that can be easily determined, and that is highly informative regarding the probability for early stage PDAC in an individual is provided.

Accordingly, one skilled in the art understands that the probability for PDAC, chronic pancreatitis, early stage PDAC, late stage PDAC, and other periampullary diseases according to the invention can be determined using either a quantitative or a categorical variable. For example, in practicing the methods of the invention the measurable feature of each of N biomarkers can be subjected to categorical data analysis to determine the probability for PDAC, chronic pancreatitis, early stage PDAC, late stage PDAC, and other periampullary diseases as a binary categorical outcome. Alternatively, the methods of the invention may analyze the measurable feature of each of N biomarkers by initially calculating quantitative variables, in particular, predicted onset of PDAC, chronic pancreatitis, early stage PDAC, late stage PDAC, and other periampullary diseases. The predicted onset of PDAC, chronic pancreatitis, early stage PDAC, late stage PDAC, or other periampullary diseases can subsequently be used as a basis to predict risk of PDAC, chronic pancreatitis, early stage PDAC, late stage PDAC, or other periampullary diseases, respectively. By initially using a quantitative variable and subsequently converting the quantitative variable into a categorical variable the methods of the invention take into account the continuum of measurements detected for the measurable features.

In the development of a predictive model, it can be desirable to select a subset of markers, i.e. at least 3, at least 4, at least 5, at least 6, up to the complete set of markers. Usually a subset of markers will be chosen that provides for the needs of the quantitative sample analysis, e.g. availability of reagents, convenience of quantitation, etc., while maintaining a highly accurate predictive model. The selection of a number of informative markers for building classification models requires the definition of a performance metric and a user-defined threshold for producing a model with useful predictive ability based on this metric. For example, the performance metric can be the AUC, the sensitivity and/or specificity of the prediction as well as the overall accuracy of the prediction model.

As will be understood by those skilled in the art, an analytic classification process can use any one of a variety of statistical analytic methods to manipulate the quantitative data and provide for classification of the sample. Examples of useful methods include, without limitation, linear discriminant analysis, recursive feature elimination, a prediction analysis of microarray, a logistic regression, a CART algorithm, a FlexTree algorithm, a LART algorithm, a random forest algorithm, a MART algorithm, and machine learning algorithms.

The selection of a subset of markers can be for a forward selection or a backward selection of a marker subset. The number of markers can be selected that will optimize the performance of a model without the use of all the markers. One way to define the optimum number of terms is to choose the number of terms that produce a model with desired predictive ability (e.g. an AUC>0.75, or equivalent measures of sensitivity/specificity) that lies no more than one standard error from the maximum value obtained for this metric using any combination and number of terms used for the given algorithm. As exemplified herein, mathematical modeling of existing serum biomarker data, by allowing for diverse responses between cases, allows for a biomarker panel to be devised that has greater than 99% accuracy for diagnosis of a low prevalence cancer, pancreatic ductal adenocarcinoma. The results described in Example 5 provide a framework for identifying useful biomarker characteristics and minimizing biomarker correlation.

In yet another aspect, the invention provides kits for determining probability of PDAC, chronic pancreatitis, early stage PDAC, late stage PDAC, or other periampullary diseases, wherein the kits can be used to detect N of the isolated biomarkers listed in Tables 1 through 4. For example, the kits can be used to detect one or more, two or more, or three of the isolated biomarkers selected from the group consisting of the biomarkers set forth in Tables 1 through 4. For example, the kits can be used to detect one or more, two or more, or three of the isolated biomarkers selected from the group consisting of the biomarkers set forth in Tables 1 through 4.

In another aspect, the kits can be used to detect one or more, two or more, three or more, four or more, five or more, six or more, seven or more, or eight of the isolated biomarkers selected from the group consisting of the biomarkers set forth in Tables 1 through 4.

In another aspect, the kits can be used to detect one or more, two or more, three or more, four or more, five or more, six or more, seven or more, or eight of the isolated biomarkers selected from the group consisting of the biomarkers set forth in Tables 1 through 4.

The kit can include one or more agents for detection of biomarkers, a container for holding a biological sample isolated from an individual; and printed instructions for reacting agents with the biological sample or a portion of the biological sample to detect the presence or amount of the isolated biomarkers in the biological sample. The agents can be packaged in separate containers. The kit can further comprise one or more control reference samples and reagents for performing an immunoassay.

In one embodiment, the kit comprises agents for measuring the levels of at least N of the isolated biomarkers listed in Tables 1 through 4. The kit can include antibodies that specifically bind to these biomarkers, for example, the kit can contain at least one of an antibody that specifically binds to a biomarker selected from the group listed in Table 1.

In one embodiment, the kit comprises agents for measuring the levels of at least N of the isolated biomarkers listed in Tables 1 through 4. The kit can include antibodies that specifically bind to these biomarkers, for example, the kit can contain at least one of an antibody that specifically binds to a biomarker selected from the group listed in Table 1.

The kit can comprise one or more containers for compositions contained in the kit. Compositions can be in liquid form or can be lyophilized. Suitable containers for the compositions include, for example, bottles, vials, syringes, and test tubes. Containers can be formed from a variety of materials, including glass or plastic. The kit can also comprise a package insert containing written instructions for methods of determining probability of PDAC, chronic pancreatitis, early stage PDAC, late stage PDAC, and other periampullary diseases.

From the foregoing description, it will be apparent that variations and modifications can be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof

TABLE 1

Protein Analytes

| Analyte | Name |
| --- | --- |
| ALCAM | activated leukocyte cell adhesion molecule |
| ANG | angiogenin |
| AXL | AXL receptor tyrosine kinase |
| AZGP1 | alpha-2-glycoprotein 1, zinc-binding |
| BAG3 | BCL2-associated athanogene 3 |
| BSG | basigin (EMMPRIN, CD147) |
| CA 19-9 | cancer antigen 19-9 |
| CEACAM5 | carcinoembryonic antigen-related cell adhesion molecule 5 (CEA) |
| CEACAM1 | carcinoembryonic antigen-related cell adhesion molecule 1 (biliary glycoprotein) |
| COL18A1 | collagen, type XVIII, alpha 1 (endostatin) |
| EPCAM | epithelial cell adhesion molecule |
| GSN | gelsolin |
| HA | soluble hyaluronic acid |
| HP | haptoglobin |
| ICAM1 | intercellular adhesion molecule 1 |
| IGFBP2 | insulin-like growth factor binding protein 2 |
| IGFBP4 | insulin-like growth factor binding protein 4 |
| LCN2 | lipocalin 2 (NGAL) |
| LIMS1 | LIM and senescent cell antigen-like domains 1 (PINCH) |
| LRG1 | leucine-rich alpha-2-glycoprotein 1 |
| LTF | lactoferrin |
| MMP11 | matrix metallopeptidase 11 (stromelysin 3) |
| MMP2 | matrix metallopeptidase 2 (gelatinase A, 72 kDa gelatinase, 72 kDa type IV collagenase) |
| MMP7 | matrix metallopeptidase 7 (matrilysin, uterine) |
| MMP9 | matrix metallopeptidase 9 (gelatinase B, 92 kDa gelatinase, 92 kDa type IV collagenase) |
| MSLN | mesothelin |
| PARK7 | DJ-1 protein |

TABLE 1-continued

Protein Analytes

| Analyte | Name |
|---|---|
| PF4 | platelet factor 4 |
| PLEC | plectin |
| PPBP | platelet basic protein |
| PRG4 | proteoglycan 4 |
| SAA | serum amyloid A |
| SPARCL1 | SPARC-like 1 (hevin) |
| SPP1 | secreted phosphoprotein 1 (osteopontin, OPN) |
| TGFBI | transforming growth factor, beta-induced, 68 kDa |
| THBS1 | thrombospondin 1 |
| TIMP1 | TIMP metallopeptidase inhibitor 1 |
| TNFRSF1A | tumor necrosis factor receptor superfamily, member 1A |
| VEGFC | vascular endothelial growth factor C |

TABLE 2 microRNA Analytes
Analyte miR-100a
miR-1290
miR-155
miR-18a
miR-196a
miR-21
miR-210
miR-221
miR-24
miR-31
miR-375
miR-885

TABLE 3

Genetic Lesion Analytes
Gene

KRAS (Gene ID: 3845)
SMAD4 (Gene ID: 4089)
CDKN2A (Gene ID: 1029)
TP53 (Gene ID: 7157)

TABLE 4

Analytes Tested by ELISA

| Analyte Identifier | Analyte Name |
|---|---|
| ALCAM | activated leukocyte cell adhesion molecule |
| ANG | angiogenin |
| AXL | AXL receptor tyrosine kinase |
| BAG3 | BCL2-associated athanogene 3 |
| BSG | basigin (EMMPRIN, CD147) |
| CA 19-9 | cancer antigen 19-9 |
| CEACAM1 | carcinoembryonic antigen-related cell adhesion molecule 1 (biliary glycoprotein) |
| COL18A1 | collagen, type XVIII, alpha 1 (endostatin) |
| EPCAM | epithelial cell adhesion molecule |
| HA | soluble hyaluronic acid |
| HP | haptoglobin |
| ICAM1 | intercellular adhesion molecule 1 |
| IGFBP2 | insulin-like growth factor binding protein 2 |
| IGFBP4 | insulin-like growth factor binding protein 4 |
| LCN2 | lipocalin 2 (NGAL) |
| LRG1 | leucine-rich alpha-2-glycoprotein 1 |
| MMP2 | matrix metallopeptidase 2 (gelatinase A, 72 kDa gelatinase, 72 kDa type IV collagenase) |
| MMP7 | matrix metallopeptidase 7 (matrilysin, uterine) |
| MMP9 | matrix metallopeptidase 9 (gelatinase B, 92 kDa gelatinase, 92 kDa type IV collagenase) |
| MSLN | mesothelin |
| PARK7 | DJ-1 protein |
| PPBP | platelet basic protein |
| PRG4 | proteoglycan 4 |
| SPARCL1 | SPARC-like 1 (hevin) |
| SPP1 | secreted phosphoprotein 1 (osteopontin, OPN) |
| TGFBI | transforming growth factor, beta-induced, 68 kDa |
| THBS1 | thrombospondin 1 |
| TIMP1 | TIMP metallopeptidase inhibitor 1 |
| TNFRSF1A | tumor necrosis factor receptor superfamily, member 1A |
| VEGFC | vascular endothelial growth factor C |

TABLE 5

Individual Analyte Performance for Comparison of Healthy Controls (CON), Chronic Pancreatitis Cases (ChPT), and Early-stage Pancreatic Ductal Adenocarcinoma Cases (PDAC)

| | Area Under Receiver Operating Characteristic Curve (95% Confidence Interval) | | | |
|---|---|---|---|---|
| | CON vs. PDAC | ChPT vs. PDAC | CON vs. ChPT | CON + ChPT vs. PDAC |
| ALCAM | 0.775 (0.687-0.858) | 0.693 (0.591-0.793) | 0.617 (0.516-0.723) | 0.734 (0.649-0.816) |
| ANG | 0.536 (0.433-0.636) | 0.566 (0.467-0.669) | 0.543 (0.436-0.649) | 0.551 (0.459-0.640) |
| AXL | 0.747 (0.657-0.833) | 0.648 (0.551-0.745) | 0.599 (0.491-0.700) | 0.697 (0.610-0.776) |
| BAG3 | 0.538 (0.436-0.646) | 0.578 (0.475-0.678) | 0.607 (0.505-0.706) | 0.520 (0.431-0.609) |
| BSG | 0.553 (0.444-0.661) | 0.623 (0.516-0.719) | 0.576 (0.476-0.680) | 0.588 (0.495-0.679) |
| CA 19-9 | 0.858 (0.781-0.926) | 0.785 (0.698-0.867) | 0.641 (0.532-0.736) | 0.821 (0.737-0.896) |
| CEACAM1 | 0.888 (0.826-0.943) | 0.775 (0.692-0.858) | 0.668 (0.572-0.763) | 0.831 (0.758-0.894) |
| COL18A1 | 0.695 (0.595-0.786) | 0.549 (0.449-0.656) | 0.623 (0.523-0.716) | 0.622 (0.536-0.707) |
| EPCAM | 0.508 (0.396-0.609) | 0.672 (0.569-0.764) | 0.704 (0.608-0.799) | 0.582 (0.491-0.672) |
| HA | 0.776 (0.688-0.854) | 0.622 (0.518-0.719) | 0.683 (0.589-0.774) | 0.699 (0.610-0.779) |
| HP | 0.614 (0.512-0.713) | 0.581 (0.479-0.689) | 0.694 (0.600-0.785) | 0.517 (0.431-0.603) |
| ICAM1 | 0.806 (0.716-0.882) | 0.635 (0.530-0.735) | 0.768 (0.674-0.846) | 0.721 (0.626-0.810) |
| IGFBP2 | 0.733 (0.640-0.821) | 0.495 (0.394-0.602) | 0.712 (0.619-0.798) | 0.614 (0.534-0.696) |
| IGFBP4 | 0.597 (0.493-0.699) | 0.556 (0.445-0.654) | 0.648 (0.541-0.746) | 0.521 (0.426-0.607) |
| LCN2 | 0.497 (0.391-0.599) | 0.585 (0.483-0.686) | 0.612 (0.512-0.713) | 0.541 (0.452-0.635) |
| LRG1 | 0.469 (0.366-0.578) | 0.501 (0.400-0.603) | 0.532 (0.424-0.630) | 0.485 (0.397-0.571) |
| MMP2 | 0.605 (0.499-0.711) | 0.552 (0.447-0.652) | 0.664 (0.560-0.762) | 0.526 (0.433-0.614) |

TABLE 5-continued

Individual Analyte Performance for Comparison of Healthy Controls (CON), Chronic Pancreatitis Cases (ChPT), and Early-stage Pancreatic Ductal Adenocarcinoma Cases (PDAC)

Area Under Receiver Operating Characteristic Curve (95% Confidence Interval)

|  | CON vs. PDAC | ChPT vs. PDAC | CON vs. ChPT | CON + ChPT vs. PDAC |
|---|---|---|---|---|
| MMP7 | 0.570 (0.469-0.675) | 0.544 (0.443-0.652) | 0.536 (0.429-0.640) | 0.557 (0.463-0.651) |
| MMP9 | 0.524 (0.420-0.628) | 0.545 (0.441-0.654) | 0.593 (0.486-0.692) | 0.510 (0.420-0.601) |
| MSLN | 0.527 (0.422-0.631) | 0.464 (0.356-0.579) | 0.488 (0.383-0.595) | 0.532 (0.444-0.619) |
| PARK7 | 0.588 (0.484-0.691) | 0.695 (0.595-0.783) | 0.618 (0.512-0.713) | 0.642 (0.556-0.727) |
| PPBP | 0.550 (0.445-0.656) | 0.549 (0.443-0.655) | 0.482 (0.383-0.588) | 0.549 (0.457-0.643) |
| PRG4 | 0.629 (0.529-0.728) | 0.524 (0.422-0.628) | 0.610 (0.514-0.707) | 0.577 (0.491-0.664) |
| SPARCL1 | 0.473 (0.366-0.578) | 0.509 (0.406-0.616) | 0.548 (0.441-0.652) | 0.491 (0.400-0.584) |
| SPP1 | 0.792 (0.708-0.867) | 0.589 (0.481-0.693) | 0.721 (0.624-0.809) | 0.690 (0.609-0.769) |
| TGFBI | 0.694 (0.591-0.786) | 0.667 (0.570-0.766) | 0.480 (0.377-0.581) | 0.681 (0.585-0.770) |
| THBS1 | 0.571 (0.468-0.673) | 0.590 (0.488-0.689) | 0.662 (0.564-0.755) | 0.509 (0.417-0.603) |
| TIMP1 | 0.686 (0.588-0.781) | 0.532 (0.428-0.638) | 0.657 (0.558-0.749) | 0.609 (0.516-0.699) |
| TNFRSF1A | 0.634 (0.529-0.735) | 0.523 (0.426-0.628) | 0.659 (0.562-0.751) | 0.555 (0.462-0.651) |
| VEGFC | 0.519 (0.413-0.618) | 0.491 (0.389-0.596) | 0.516 (0.410-0.620) | 0.505 (0.411-0.593) |

TABLE 6

Subject Characteristics

| Subject Class | Subject Group | No. cases | Median Age (Range), Years |
|---|---|---|---|
| Pancreatic Ductal Adenocarcinoma | Total | 60 | 68.5 (49-92) |
|  | Female | 26 | 71.5 (49-91) |
|  | Male | 34 | 66 (49-92) |
|  | Stage IA | 4 | 74.5 (50-78) |
|  | Stage IB | 12 | 64.5 (50-92) |
|  | Stage IIA | 44 | 68.5 (49-91) |
| Healthy Control | Total | 60 | 63 (45-81) |
|  | Female | 26 | 64.5 (62-79) |
|  | Male | 34 | 59 (45-81) |
| Chronic Pancreatitis | Total | 60 | 60.5 (47-86) |
|  | Female | 26 | 58 (47-86) |
|  | Male | 34 | 62.5 (53-83) |

All patents and publications mentioned in this specification are herein incorporated by reference to the same extent as if each independent patent and publication was specifically and individually indicated to be incorporated by reference.

The following examples are provided by way of illustration, not limitation.

EXAMPLES

Example 1. Basigin is a Biomarker for Early Stage PDAC

BSG levels were measured by ELISA in plasma from 50 healthy control subjects (mean=3.06 ng/ml, 95% CI=2.6-3.5), 20 patients with chronic pancreatitis (3.92 ng/ml, 3.18-4.65 CI), and 50 pre-treatment samples from patients with PDAC (4.74 ng/ml, 4.24-5.23 CI). Nonparametric analysis revealed a significant difference for the model (P=0.0006, Kruskal-Wallis rank sums). By ANOVA and Tukey-Kramer post-hoc tests, the distributions of BSG levels in PDAC and healthy control subjects were significantly different (P<0.0001), but the comparison of PDAC to chronic pancreatitis cases was not significant (P=0.195). However, a striking difference was noted after separating the PDAC cases into early stage (I-II) and late stage (III-IV) groups (FIG. 1). ANOVA indicated that early stage disease (N=30, 5.56 ng/ml, 4.96-6.16 CI) had significantly elevated BSG levels compared to healthy controls (P<0.0001), chronic pancreatitis cases (P=0.005), and late stage PDAC cases (P=0.0002, n=20, 3.51 ng/ml, 2.77-4.25 CI). These data confirm the presence of detectable BSG in our plasma samples and suggest that circulating BSG is an early stage phenomenon during PDAC development.

Figure 2A:
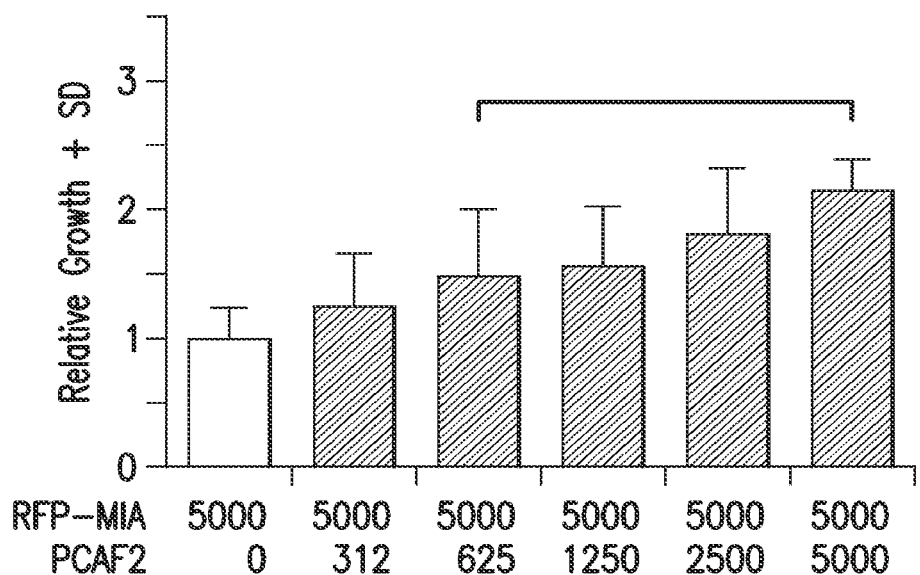
FIGS. 2A-B show dose-dependent enhancement of PDAC cell proliferation in direct co-culture with fibroblasts. The effect of co-culture with pancreas cancer-associated fibroblasts (PCAF2) on RFP-MIA PaCa-2 growth was monitored by RFP fluorescence. Numbers below the data bars represent initial plating densities for each cell type. RFP fluorescence intensity was measured 3 hours after initial plating to allow for adherence (Day 0) and then daily for three days. Relative growth is presented as the Day 3/Day 0 RFP fluorescence ratio relative to the Day 3/Day 0 RFP fluorescence ratio of RFP-MIA PaCa-2 cells alone (open bar).
Figure 2B:
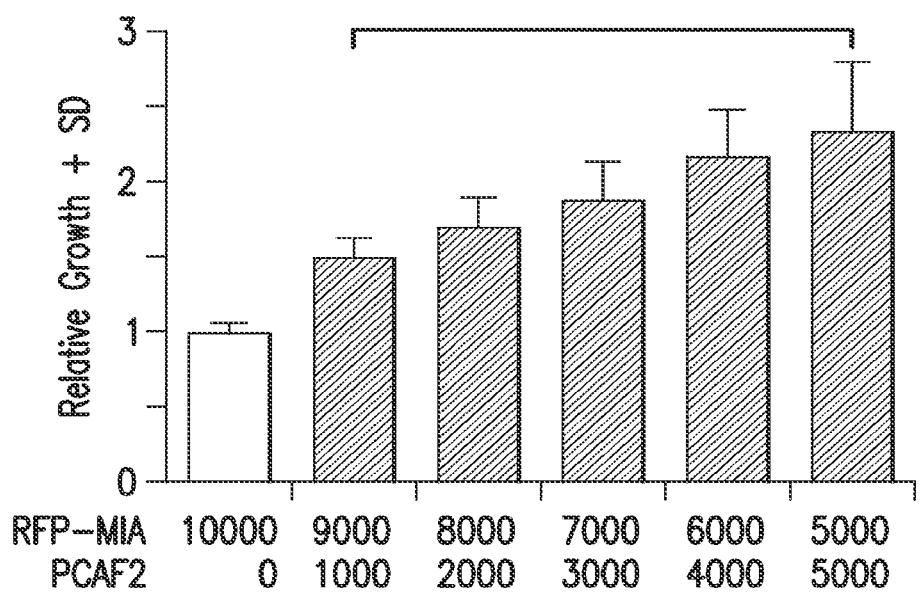
Figure 3:
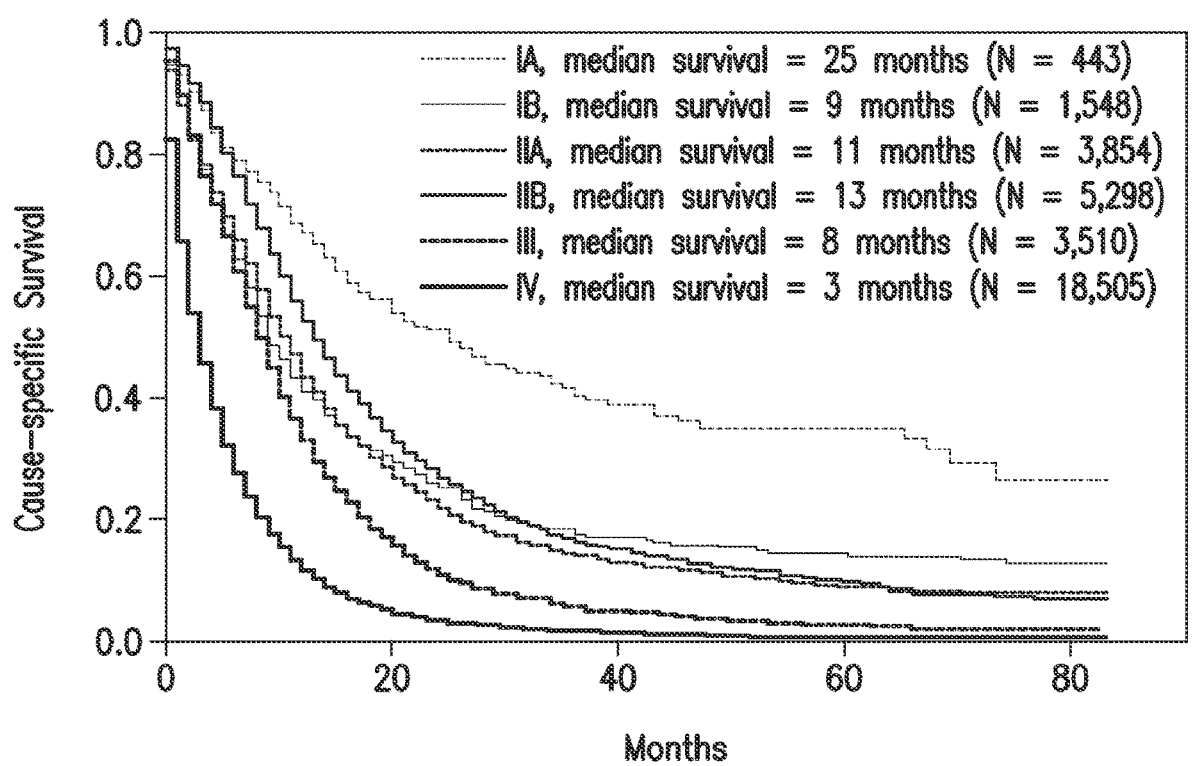
FIG. 3 shows stage-specific survival for PDAC. Data was abstracted from the SEER Research Database (2004-2010). The majority of cases are late stage, with highest survival seen for those cases in which the tumor is confined to the pancreas and less than 2 cm in its greatest dimension (Stage IA).
Figure 4:
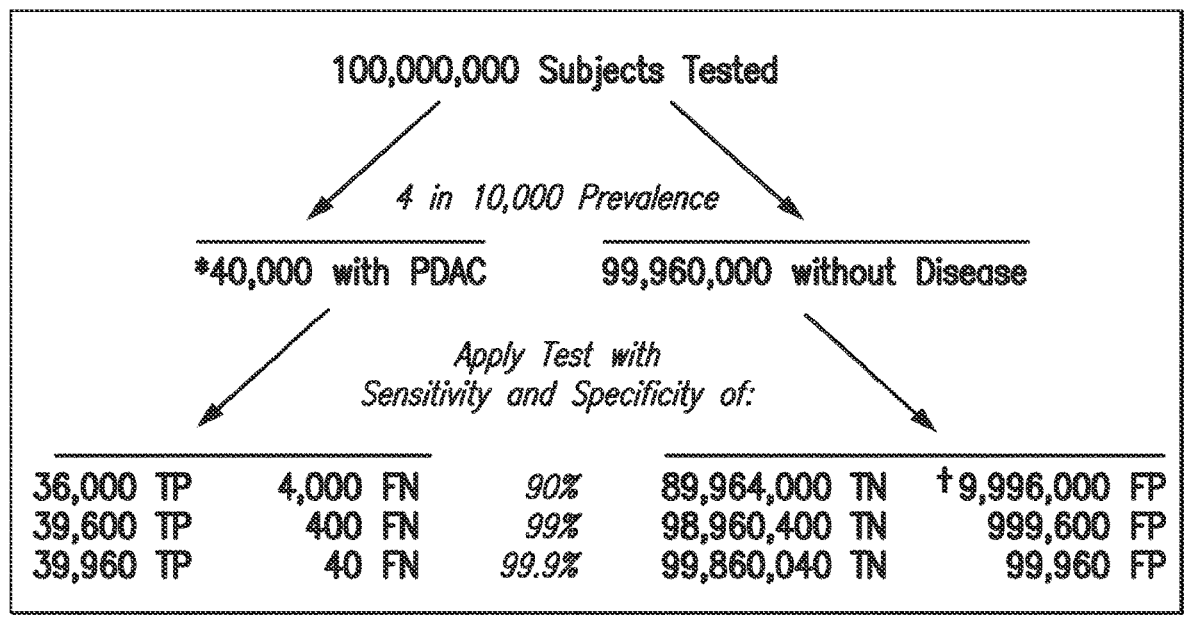
FIG. 4 shows interpretation of test results at various levels of test accuracy for diagnosis of PDAC. Outcomes are shown for a population of 100 million individuals (the current approximate number of individuals over the age of 50 in the United States) and assuming an annual disease prevalence of 4 in 10,000. FN=False-negative test results; FP=false-positive test results; TN=true-negative test results; TP=true-positive test results. Positive predictive value=probability of PDAC in a patient with a positive test result=TP/(TP+FP). Negative predictive value=probability of no PDAC in a patient with a negative test result=TN/(TN+FN). *$2.6 billion annual cost to treat. †$5.5 billion annual cost for a single contrast-enhanced computed tomography (CT) follow-up screen for each false positive determination (based on 2011 Medicare technical and professional reimbursement rate of $554/CT).

PDAC cell line co-culture with PCAFs: The human pancreatic cancer cell lines AsPC-1, MIA PaCa-2, and PANC-1, stably transfected to express red fluorescent protein (RFP), have been created and maintained in our laboratory and are available for this study. Briefly, the effect of co-culture with pancreas cancer-associated fibroblasts (PCAF2) on RFP-MIA PaCa-2 growth was monitored by RFP fluorescence. Numbers below the data bars represent initial plating densities for each cell type. RFP fluorescence intensity was measured 3 hours after initial plating to allow for adherence (Day 0) and then daily for three days. Relative growth is presented as the Day 3/Day 0 RFP fluorescence ratio relative to the Day 3/Day 0 RFP fluorescence ratio of RFP-MIA PaCa-2 cells alone (open bar). Relative growth was monitored for a constant number if initially plated RFP-MIA PaCa-2 cells co-cultured with an increasing number of either PCAF2 (FIG. 2A). The effect of co-culture with PCAF2 on RFP-MIA PaCa-2 cell growth was also monitored while keeping the initial total cell plating density constant (FIG. 2B). Data represents the combined results of 3-4 independent experiments. For each experiment, 4-6 replicate wells for each condition were performed in parallel. Bracket indicates conditions significantly elevated relative to RFP-MIA PaCa-2 cells alone by ANOVA and Fisher's PLSD post-hoc test (P<0.01). Currently, 40 human primary pancreatic cancer-associated fibroblasts have been isolated and characterized. To date, all of the isolated PCAFs demonstrate the ability to increase PDAC cell line proliferation 2-3 fold in co-culture (FIG. 2). These data illustrate the system that will be used in Example 4 to assess the effect of fibroblasts on BSG, MMP-2, and MMP-9 in co-culture supernatants.

Example 2. Plasma BSG, MMP-2, and MMP-9 Levels as Circulating PDAC Diagnostic and Prognostic Biomarkers Differential levels of BSG in healthy control, chronic pancreatitis, early stage PDAC and late stage PDAC cases will be confirmed. MMP-2 and MMP-9, whose expression is controlled by BSG will be evaluated as PDAC diagnostic and prognostic biomarkers. All three analytes will be compared to CA 19-9 levels, the current gold standard PDAC biomarker.

Experimental Approach: Plasma protein levels will be determined by ELISA (DEMPOO Human EMMPRIN/CD147 Quantikine ELISA Kit, MMP200 Total MMP-2 Quantikine ELISA Kit, DMP900 Human MMP9 Quantikine ELISA Kit; R&D Systems, Minneapolis, Minn.). CA 19-9 levels will also be measured for each sample (#6909 Gastrointestinal Cancer Antigen CA 19-9 Enzyme immunoassay; Diagnostic Automation; Calabasas, Calif.). The plasma samples will be diluted and analytes measured following the manufacturer's recommended protocol. Protein/antigen levels will be calculated by comparing absorbance readings against a calibration curve generated from standards of known concentration. For those samples whose initial measurements do not initially fall within the linear detection range, sample dilutions will be modified accordingly and the measurements repeated.

Levels of BSG, MMP-2, MMP-9, and CA 19-9 will be determined in plasma samples from 100 patients with histologically/cytologically confirmed PDAC, 100 healthy control subjects (gender-matched and age-approximated to PDAC cases), and 80 patients with chronic pancreatitis. PDAC samples will be selected to have equal representation of early stage and late stage cases. Sufficient samples for this study have been previously collected and banked in our institution. Sequential cases will be chosen for each group, where possible. Plasma samples from normal control subjects were obtained from healthy adults accompanying index patients. All blood samples were collected prior to treatment (except for stent placement in jaundiced PDAC cases), separated into the plasma component, and frozen for later analysis. For PDAC cases, bilirubin levels at the time of sample collection will be abstracted from patient charts.

Data Analysis and Interpretation: Linear models will be used to relate BSG, MMP-2, MMP-9, and CA 19-9 levels to gender, age, and stage. Additional comparisons for protein/antigen levels in PDAC cases will be made for bilirubin and treatment (patients receiving surgical or chemoradiation treatments expected to affect survival). Univariate Cox models will be employed for survival analyses with multivariate models developed using significant univariate parameters. Correlation analyses will be performed to compare the relationships between BSG, MMP-2, and MMP9 levels. Receiver operating characteristic curves will be determined and the area under the curve calculated as a comparative measure of diagnostic accuracy. Sensitivity and specificity will be determined at optimal (maximizing accuracy) and assigned threshold levels (yielding 95% specificity). Statistical analyses will be performed using "R" statistical computing software, version 3.0.2 or later (38). P values <0.05 will be considered significant.

Although the proposed experiments are designed to characterize BSG, MMP-2, and MMP-9 as potential diagnostic and prognostic biomarkers, the major objective of the aim is to validate the preliminary findings that BSG is elevated in early stage PDAC compared to the other groups. Two specific comparisons are of particular interest:

BSG levels in stage I-II PDAC vs. stage III-IV PDAC—We will test the hypothesis that BSG levels will be elevated in plasma samples from early stage PDAC cases relative to samples from late stage cases. By design, the sample set can be split for analysis either as test and validation sets or as a combined set (with cross-validation). Based on the pilot data ($\sigma=2.2$, $\delta=1$), a sample size of 50 has 88% power to detect a difference at $\alpha=0.05$ using the student's t-test. The combined data set (N=100) will have greater than 99% power to detect a similar effect size.

BSG levels in stage I-II PDAC vs. ChPT—We will also test the hypothesis that BSG levels will be elevated in plasma samples from early stage PDAC cases relative to samples from chronic pancreatitis cases. Based on the pilot data ($\sigma=2.4$, $\delta=0.8$), a sample size of 50 (recapitulating the pilot experiment) has 65% power to detect the difference at $\sigma=0.05$, although there was greater power in the multi-group analysis. The combined data set (N=130) will have greater than 97% power to detect a similar effect size.

The preliminary data is compelling for the differential BSG levels between early and late stage cases lending high confidence that the difference will be recapitulated. Such a result will justify continued investigation for BSG as a diagnostic marker, including evaluation in a larger sample set from different institutions, examination of BSG levels in other pancreatic diseases (ampullary adenocarcinoma, neuroendocrine tumors, benign and pre-neoplastic cystic lesions), and testing samples from high-risk subjects and pre-diagnostic samples from patients who subsequently developed PDAC. The preliminary evidence is less compelling for the comparison of early stage PDAC and ChPT, due to the higher variance in the ChPT group. Chronic pancreatitis is a persistent diagnostic problem for patients presenting with periampullary disease and biomarkers that can distinguish PDAC from the benign inflammatory condition are desirable. However, the lack of discrimination by aggregate BSG levels would not preclude its use in diagnostic panels since other biomarkers could compensate. The potential for BSG levels to indicate early stage disease is the principal benefit.

Example 3. Assessment of Tumor BSG Levels in Resected Cases by Immunohistochemistry and Determination of the Relationship of BSG Expression to Extent of ECM Deposition in Cancer-Associated Stroma The experiments are expected to enlighten the apparent biphasic distribution of plasma BSG levels observed in preliminary data with 12 early stage PDAC patients exhibiting high levels, while 17 showed levels comparable to controls. One possibility is that plasma BSG levels correspond to the extent of desmoplasia in the primary tumor. Addressing this possibility will provide mechanistic insight and suggest further investigations, particularly in regards to stratification of patients for MMP or BSG inhibitor treatment. The experiment will also evaluate tissue BSG expression as a prognostic indicator.

Experimental Approach: Paraffin tissue blocks will be selected from clinical pathology specimens that have both cancer and associated stroma represented for a minimum of 10 cases from the high plasma BSG group and 10 cases from the low plasma BSG group. Sequential sections from each case will be stained with hematoxylin and eosin (H&E), Masson's tri-chrome, and BSG via immunofluorescence. Antibodies for BSG staining will be optimized for dilution and antibody specificity evaluated by comparing sections stained using secondary antibody only and sections stained in the presence of excess antigen. Slides will be evaluated by investigators blinded to the sample identity using a four point scale representing quartiles (0-100% or lowest-highest). H&E slides will be scored for inflammatory cell infiltration and used to evaluate tumor structure. BSG slides will be evaluated for immunofluorescent intensity and the percent of staining (coverage) in both cancer cells and associated stroma. Scanned images of tri-chrome stained sections will be used to determine the extent of collagen deposition relative to the number of cancer cells.

Data Analysis and Interpretation: We will test the hypotheses that BSG expression in tumors is directly (inversely) related to the extent of desmoplasia by comparing the distribution of standardized collagen deposition to BSG intensity and coverage scores. Models will be developed that evaluate the relationship of desmoplasia and BSG expression to inflammatory cell infiltration as well as BSG released into circulation. It is unclear if, at the time of resection, desmoplasia will have been depleted by the activity of remodeling factors such as BSG and MMPs or if extensive desmoplasia results in higher BSG expression. Establishing causality will require techniques such as those proposed in Example 4. Prognostic models for BSG tumor expression will also be developed similarly to those described in Example 2.

Example 4. Determination of BSG, MMP-2, and MMP-9 in Cell Culture Supernatants in Response to PCAFs in Co-Culture with PDAC Cell Lines This example describes development of an in vitro system that will allow investigations into the mechanisms of BSG activity in response to the presence of stromal cells. Tissue culture allows modulation of specific factors. Gain-of-function experiments using expression plasmids and loss-of-function experiments using RNAi/stable hairpin expression or blocking antibodies are effective tools for dissecting mechanisms. The results of these experiments will be hypothesis generating and the system will allow subsequent investigation into temporal expression and spatial targeting information as well as mechanistic probing.

PCAF cells will be seeded in 96-well plates at a density of 5,000 cells/well as outlined in preliminary data. After 24 hours, RFP-tagged PDAC cells will be added (5,000 cells/well) and incubated at 37° C. for an additional 3 hours. RFP measurements will then be made (Day 0 reading). After 3 days in culture, the Day 3 RFP measurement will be taken and supernatants collected and cleared of cells and debris by centrifugation. Supernatants from four replicate wells will be combined and BSG, MMP-2, and MMP-9 levels will be determined by ELISA as described in Aim 1. Initially, RFP-AsPC-1 cell lines will be used with four PCAF lines, with additional PDAC cell lines and PCAFs used as directed by experimental results. Each experiment will be independently repeated four times.

Raw data will consist of BSG, MMP-2, and MMP-9 measurements from four independent experiments. Since PDAC cells grow more rapidly in co-culture, the contribution of BSG, MMP-2, and MMP-9 from these cells should be higher than PDAC cells grown alone. Therefore, ELISA measurements will be standardized to mean RFP readings for each group, which will also minimize plate effects. Since PCAFs grow much more slowly than PDAC cells, their differential contribution should be minimal. We will test the hypothesis that levels of one or more of the proteins will increase in co-culture supernatants relative to (additive) levels in supernatants from culture of the individual cells. Given its regulatory role, it is expected that if BSG levels increase, then MMP-2 and MMP-9 levels will also increase. If BSG levels remain unchanged in supernatants, expression studies (PCR, immunohistochemistry) will be performed. Possible explanations for this outcome would include the lack of effectors required for BSG release or that system (PCAFs and PDAC cells) has been pre-programmed for specific BSG expression in the tumor. Decreased BSG levels, although not expected, can indicate the presence or induction of inhibitors.

Example 5. Development of an Accurate Diagnostic Biomarker Panel for Low Prevalence Cancers This Example demonstrates that a highly accurate blood-based diagnostic panel can be developed from a reasonable number of individual serum biomarkers that are relatively weak classifiers when used singly. A panel constructed as described in this Example is advantageous in that a high level of specificity can be forced, accomplishing a prerequisite for screening asymptomatic populations for low-prevalence cancers.

Existing biomarkers, biomarker panels, and diagnostic algorithms fall well short of the accuracy levels required to bring the number of false-positive determinations in asymptomatic populations into an acceptable range. Brand et al., Clin Cancer Res 2011, 17:805-816; Firpo et al., World J Surg 2009, 33:716-722; Lee and Saif, J O P 2009, 10:104-108; Wingren et al., Cancer Res 2012, 72:2481-2490; Winter et al., J Surg Oncol 2013, 107(1):15-22. Since PDAC develops from multiple different combinations of genetic and possibly epigenetic lesions (Jones et al., Science 2008, 321:1801-1806; Ryan et al., Science 2012, 336:1513-1514), it seems logical that individual cancer cases may express a subset of markers while other cases express a different subset. Thus, attempts to identify a single test for discrimination of all PDAC cases may be frustrated because of disease heterogeneity. We developed mathematical models based on experimental data from nine serum biomarkers, all of which were significantly elevated in pancreatic cancer cases relative to controls. We asked if an accurate panel classifying tool could be developed from a group of these weak individual biomarkers and hypothesized that increased accuracy could be realized by allowing for multiple combinations of biomarkers, accommodating disease heterogeneity.

All studies were carried out with the approval of the University of Utah Institutional Review Board and written informed consent was obtained for each participant enrolled in the study protocols.

Serum levels of AXL, CA 19-9, haptoglobin, hyaluronic acid, MMP-7, MMP-11, osteopontin, serum amyloid A, and TIMP-1 were measured in sera from 117 healthy control subjects and 58 chronic pancreatitis patients, and 159 PA patients collected prior to treatment. Control serum samples were obtained from both healthy adults accompanying index patients to clinic visits. Diagnoses of PDAC cases were confirmed by histological evaluation and consisted of a range of stages (10 stage IA or IB, 20 stage IIA, 47 stage IIB, 30 stage III, and 52 stage IV). Diagnostic and prognostic characteristics for CA 19-9 (Poruk et al., Curr Mol Med. 2013, 13(3):340-5), haptoglobin (Firpo et al., World J Surg 2009, 33:716-722), osteopontin (Poruk et al., Pancreas. 2013, 42(2):193-7), serum amyloid A (Firpo et al., World J Surg 2009, 33:716-722), and TIMP-1 (Poruk et al., Pancreas. 2013, 42(2):193-7)) in our cohort have been previously published, as have prognostic characteristics for MMP-7 (Fukuda et al., Cancer Cell 2011, 19:441-455). Biomarker characterization for AXL, hyaluronic acid, and MMP-11 will be published elsewhere. The median number of biomarkers queried per sample was 6 and missing data points were imputed.

We modeled the behavior of a biomarker panel consisting of a sum of indicator variables, then chose a cutoff for the sum to force specificity to be high, and calculated the resulting sensitivity. To generate correlated biomarkers, we simulated independent normal random variables for each biomarker, and then added a common simulated random variable to each of them to introduce correlation. By varying the standard deviation of the common component, the correlation between the simulated biomarkers could be adjusted. We then made a 95th percentile cutoff for each simulated biomarker and assessed the performance as above. R statistical computing software version 2.8.0 (The R Foundation for Statistical Computing, Vienna Austria) was used for the simulations.

Characteristics of Individual PDAC Biomarkers

Figure 5:
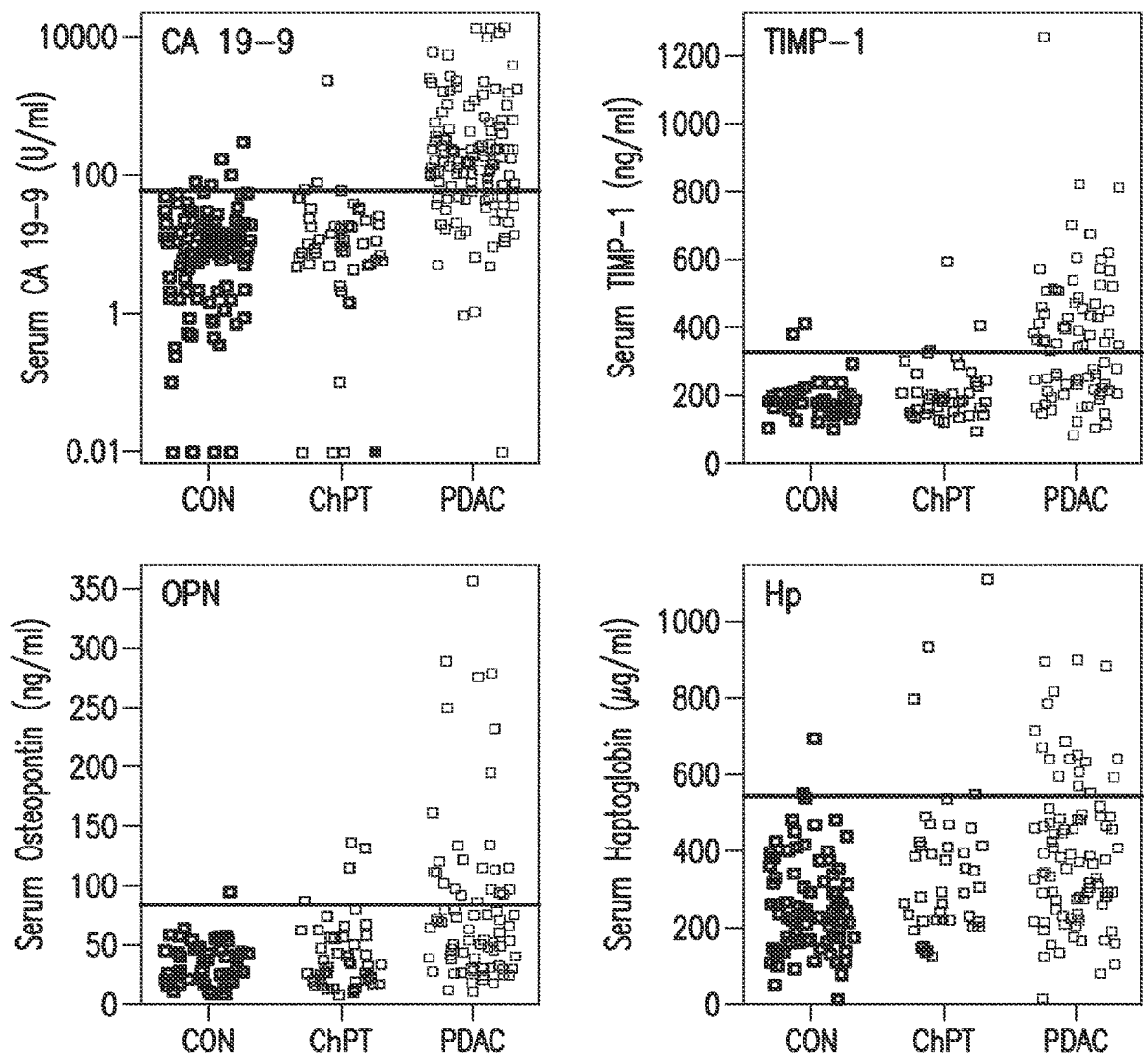
FIG. 5 shows relative distributions for PDAC diagnostic biomarkers. Levels of CA 19-9, haptoglobin (Hp), MMP-7, osteopontin (OPN), and TIMP-1 demonstrate considerable overlap in serum from healthy control subjects (CON), chronic pancreatitis patients (ChPT) and pancreatic ductal adenocarcinoma (PDAC) patients. Each data point represents the biomarker level for an individual sample. Note that serum CA 19-9 levels are presented using a logarithmic scale. Green horizontal lines indicate the 95% specificity threshold for the individual biomarkers.

To address the possibility of devising a test with 99% sensitivity and specificity, we sought to develop mathematical models based on experimental serum biomarker data. From previous experiments in which we determined levels of various biomarkers in serum from PDAC patients, chronic pancreatitis patients, and healthy subjects, we identified nine biomarkers whose mean levels were significantly elevated in PDAC cases relative to controls. These biomarkers were soluble AXL, CA 19-9, haptoglobin, soluble hyaluronic acid, matrix metallopeptidase 7 (MMP-7), matrix metallopeptidase 11 (MMP-11), osteopontin, serum amyloid A, and TIMP metallopeptidase inhibitor 1 (TIMP-1). Although the mean values of each of these biomarkers were significantly elevated in PDAC cases, accurate classification of individual results is problematic because of the large overlap of values within case and control groups. The individual biomarkers are thus weak diagnostic classifiers. The overlapping distributions for CA 19-9, haptoglobin, osteopontin, and TIMP-1 are shown in FIG. 5. This observed overlap is consistent with disease heterogeneity in that individual cancer cases may develop to express a subset of markers while other cases express a different sub set.

For the nine biomarkers, a sample set from 117 healthy control subjects, 58 chronic pancreatitis patients, and 159 PA patients was identified for which at least 3 of the 9 biomarkers were measured in individual samples. The median number of biomarkers queried per sample was 6 and missing data points were imputed. This final data set was used to identify biomarker characteristics for model development. To prioritize high specificity, we first assigned a diagnostic threshold (the indicator variable) at the 95th percentile of control values on the individual biomarkers and then calculated the resulting sensitivity. Between 17% and 75% of the PDAC cases had values above the 95% specificity threshold with an average sensitivity for all biomarkers of 32%.

Since direct correlation between biomarkers provides less diagnostic information than independent predictors, we also assessed the degree of correlation between the nine biomarkers within each group (PDAC, healthy controls, chronic pancreatitis). The correlation between the indicator variables was near zero in controls and slightly positive in PDAC cases. None of the biomarkers were highly correlated. The correlation in the PDAC samples had mean of 0.15 and median 0.13, but was highly variable (range −0.12-+0.44). The mean and median correlation in the controls was 0.12 and 0.088, respectively. Since the square of the correlation is the percentage of shared variation, markers shared about 2% of the variation in cases and 1-2% of variation in controls. This could be an overestimate, as missing data was imputed.

Modeling PDAC Biomarker Panels

We modeled the behavior of a biomarker panel consisting of a sum of indicator variables, then chose a cutoff for the sum to force specificity to be high, and calculated the resulting sensitivity. To generate correlated biomarkers, we simulated correlated continuous biomarker data, made a 95th percentile cutoff for each biomarker and then assessed performance as above. The average correlation assumption was conservative in that we ignored inverse correlation in our modeling, which would tend to increase overall accuracy of the panel. Therefore, we also modeled the less conservative correlation assumption of 0.05.

Figure 6A:
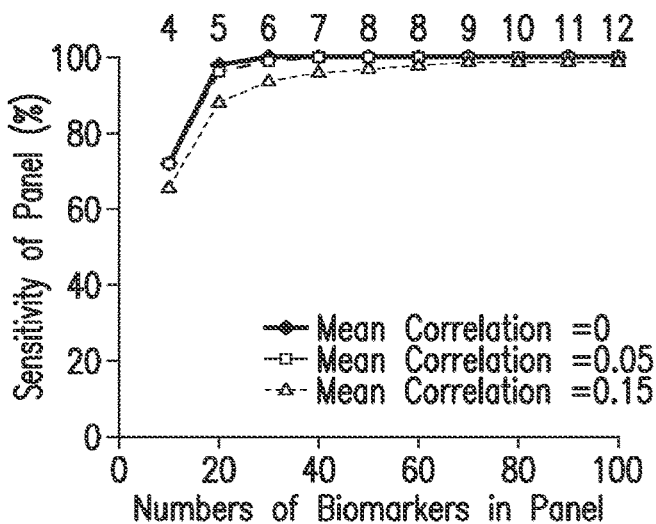
FIGS. 6A-C shows the characteristics of biomarker panels with 99% specificity. The modeled sensitivity of biomarker panels is given for panels consisting of between 10 and 100 individual biomarkers.
Figure 6B:
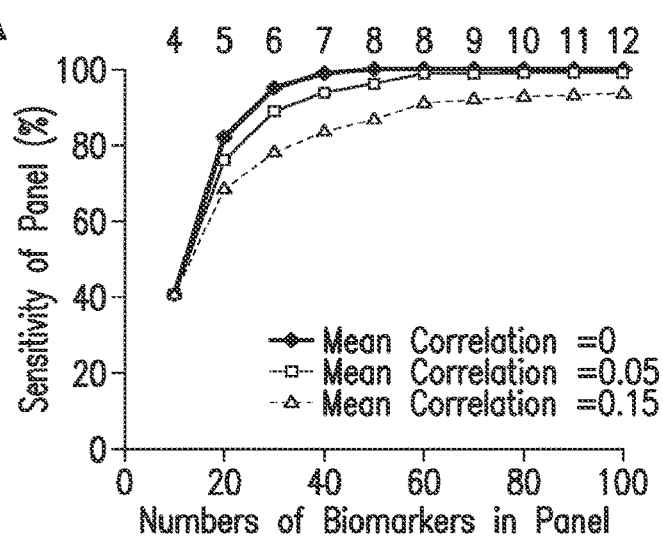
Figure 6C:
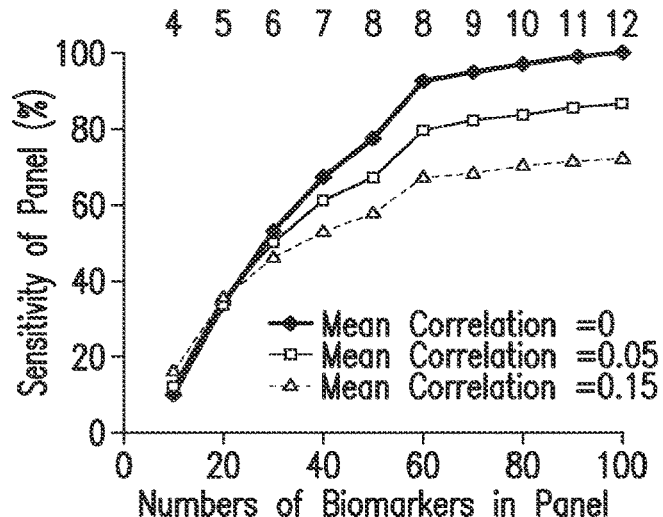

Modeling results for three panels that required 99% panel specificity, but were derived using different sensitivity assumptions about the individual biomarkers are shown in FIG. 6. The model demonstrated, for example, that a panel consisting of 40 biomarkers characterized individually by 32% sensitivity at 95% specificity would require any 7 biomarkers to be above the threshold and would result in a panel sensitivity of at least 99% (FIG. 6 B). The addition of correlation assumptions reduced sensitivity for the 40-biomarker panel to 94% at an average correlation of 0.05 and 84% at an average correlation of 0.15. Increasing the mean sensitivity of the individual biomarkers from 19% to 42% in the panel not only reduced the number of biomarkers required for high accuracy, but also reduced the contribution of correlation between the individual biomarkers.

The idea was conceived to generate a "strong classifier" panel from a group of "weak classifiers", with the stipulation that the algorithm allow for heterogeneity of the disease. The goal of accommodating disease heterogeneity by allowing different biomarker subsets would increase the overall number of biomarkers necessary in the panel. Models developed using the characteristics of nine biomarkers measured in human samples revealed that panels with 99% specificity and sensitivity could be achieved using a reasonable number of biomarkers. The approach is advantageous in that a high level of specificity can be forced and demonstrates that accommodating heterogeneity in the system has the potential to improve accuracy of cancer diagnostic biomarker panels, particularly for low-prevalence cancers.

Although the main goal was to evaluate if increased accuracy could be realized by allowing for disease heterogeneity, one limitation of the experimental design is that the dataset used biomarker levels from all PDAC stages. To be effective at improving outcomes, any diagnostic screening test should be able to identify early stage, treatable cases. Whether or not these biomarkers exist for PDAC will require further confirmation. The likelihood of finding 30-50 biomarkers with at least the average levels of accuracy seen in the nine biomarkers used here seems reasonable given that 162 secreted proteins are routinely over expressed in PDAC tumors (Harsha et al., PLoS Med 2009, 6:e1000046) and other biomarkers, such as degraded cell-surface proteins, miRNAs, genetic mutations, and metabolic products could be incorporated to extend the panel. Since highly correlated biomarkers provide the same information, the most suitable biomarkers for inclusion in a panel will likely be those that identify different features of the disease. Finally, although increasing the accuracy of tests for low prevalence cancers would reduce the cost and distress associated with falsely positive determinations in screening of asymptomatic populations, an acceptable level for false-positive determinations is an open question that need be addressed by clinical discourse.

This Example demonstrates that mathematical modeling of existing serum biomarker data, by allowing for diverse responses between cases, allows for a biomarker panel to be devised that has greater than 99% accuracy for diagnosis of a low prevalence cancer, pancreatic ductal adenocarcinoma. The results suggest that limiting analysis to those biomarkers with only the highest accuracy may be counterproductive and provide a framework for identifying useful biomarker characteristics and minimizing biomarker correlation.

Example 6. Development of an Accurate, Blood-Based Assay to Screen Asymptomatic Patients for Pancreatic Ductal Adenocarcinoma (PDAC) Risk With the intent of developing an accurate, blood-based assay that could be used to screen asymptomatic patients for pancreatic ductal adenocarcinoma (PDAC) risk, levels of 30 analytes (Table 4) were measured in each of 180 serum samples (Table 6) from healthy control subjects, chronic pancreatitis cases, and an unique cohort of early stage pancreatic cancer cases. Multiple analytical methodologies were applied to the resulting data set and diagnostic algorithms were identified with accuracies approaching 100%. With the most rigorous predictive cross-validated analyses available, greater than 83% accuracy is expected for classification of additional samples. The analytic framework allows the addition of other molecular signals. It is expected that increased accuracy can be realized by incorporating additional analytes into the resulting algorithms.

Figure 9:
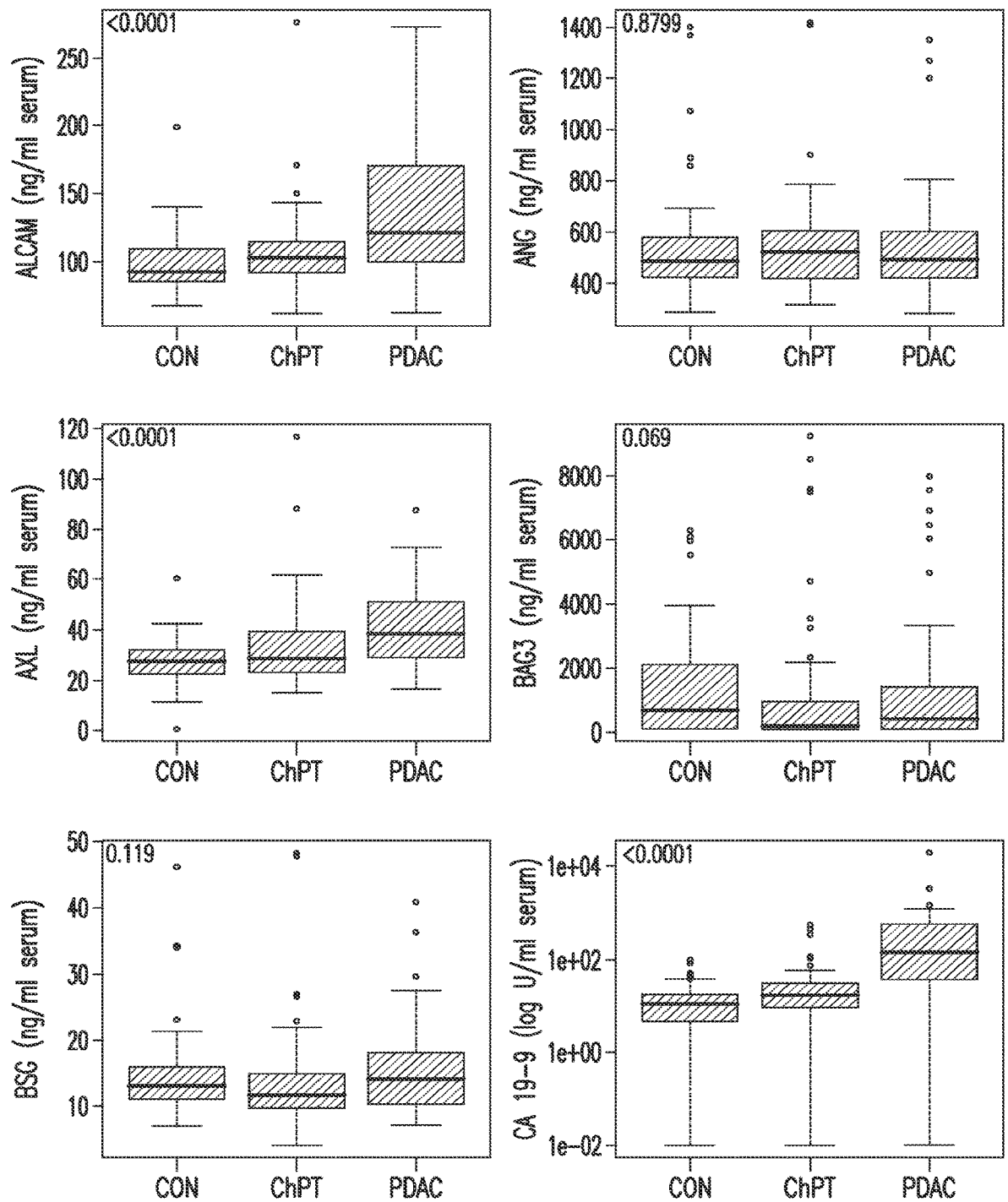
FIG. 9 shows boxplots indicating the comparison of serum analyte levels between healthy control subjects (CON, N=60), chronic pancreatitis cases (ChPT, N=60) and early stage pancreatic cancer cases (PDAC, N=60). Analytes are listed alphabetically and the P-value for the group comparison is indicated in bold in each plot (Kruskal-Wallis one-way analysis of variance by ranks).
Figure 9:
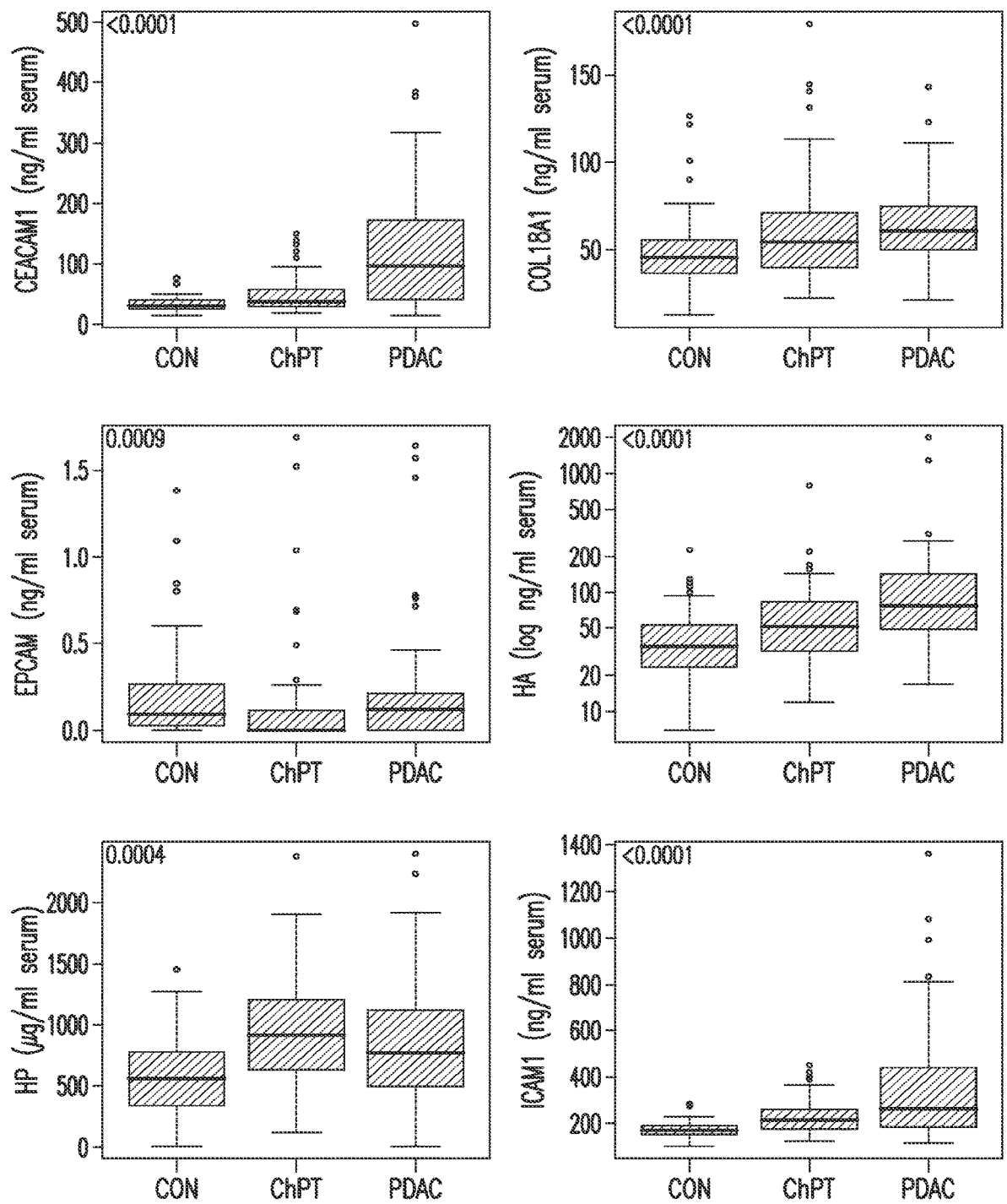
Figure 9:
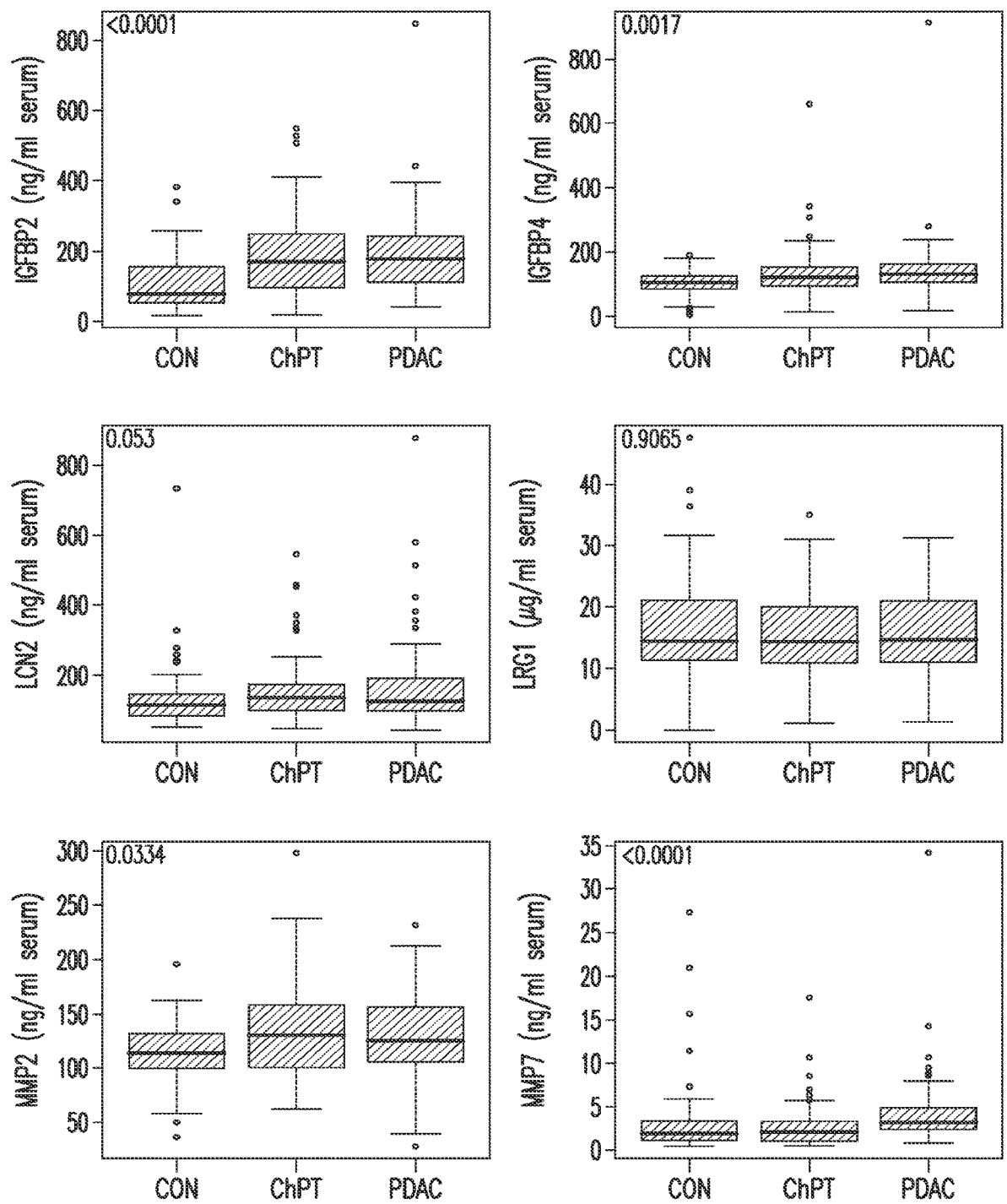
Figure 9:
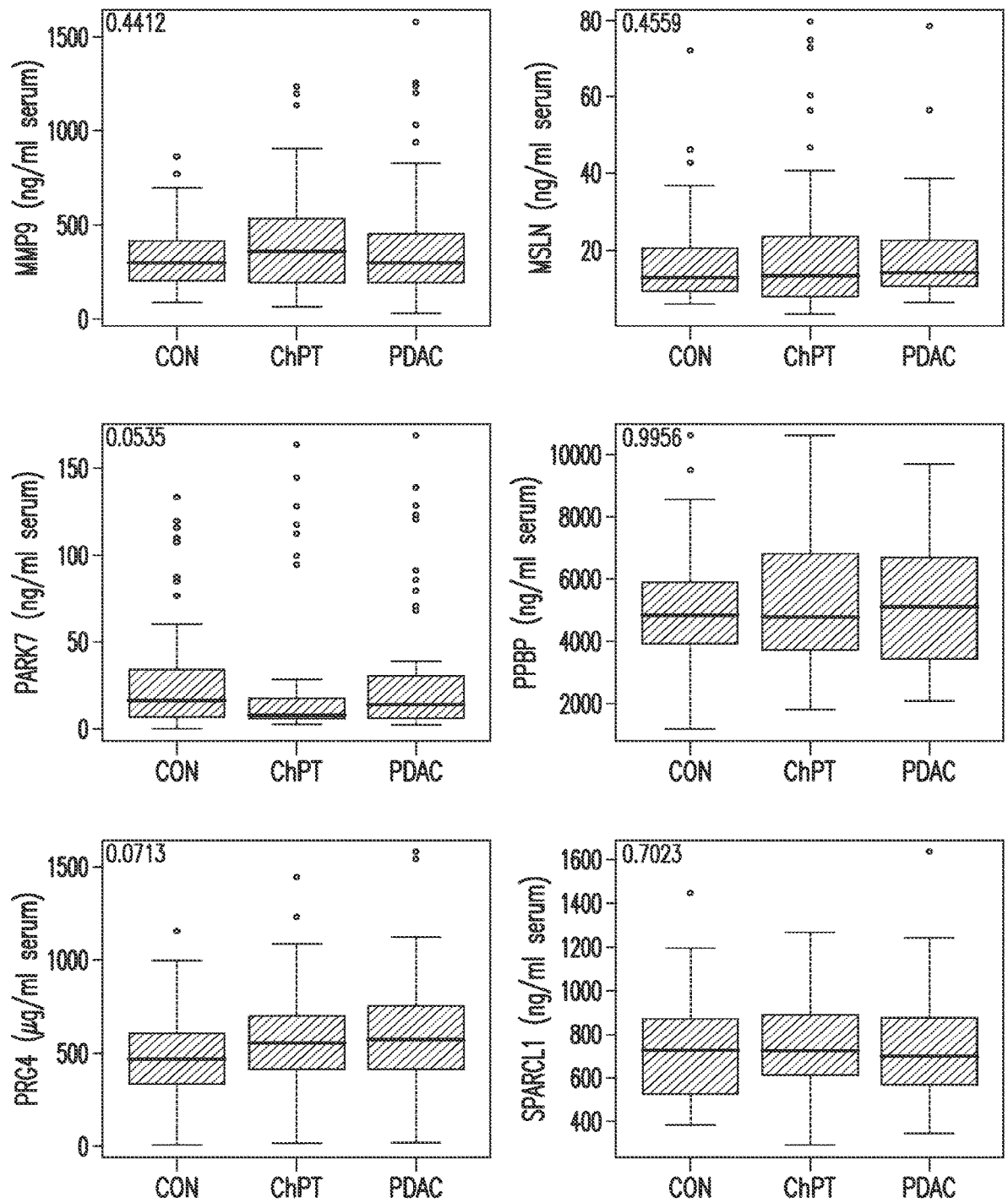
Figure 9:
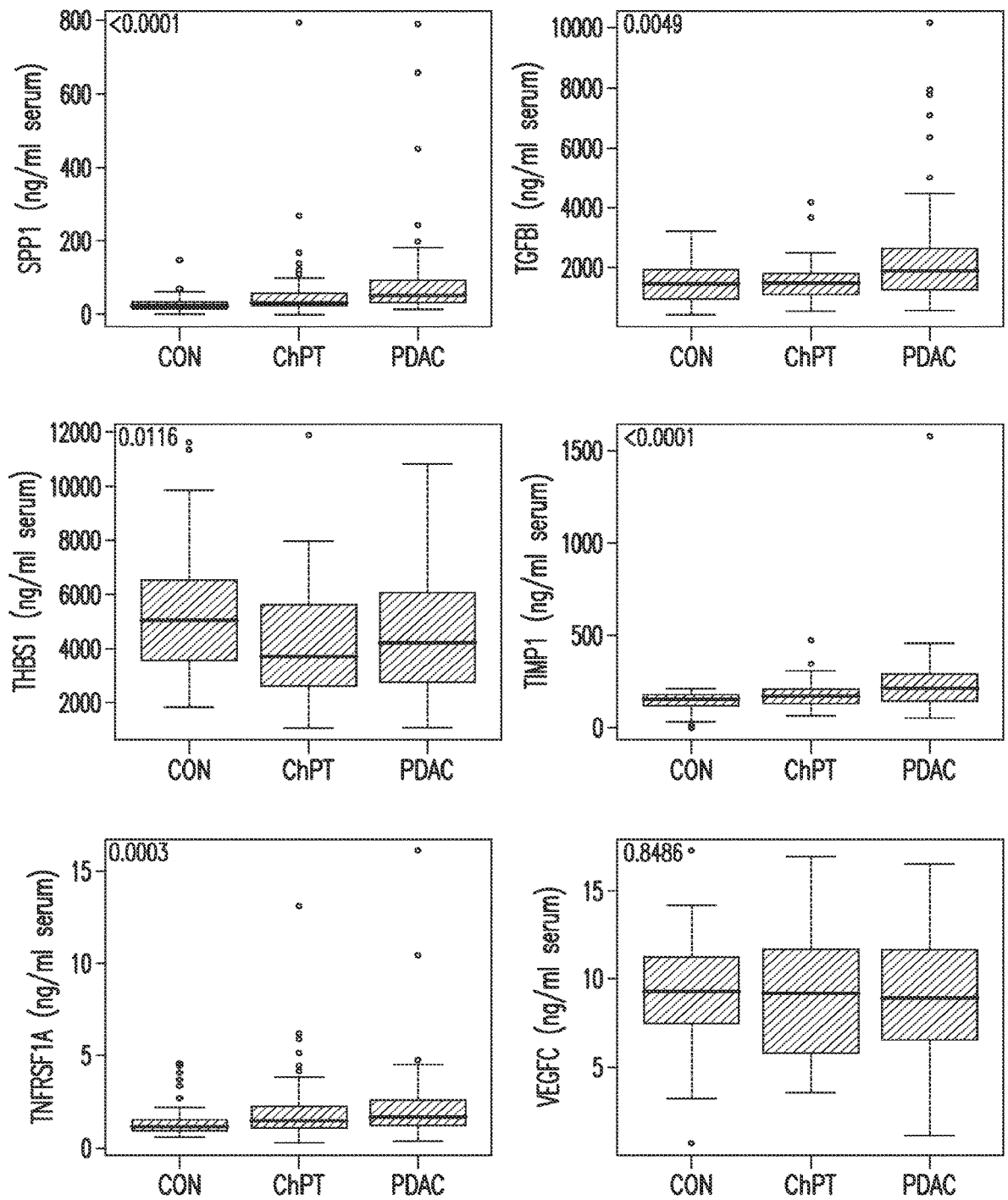

Individual Analyte Performance for Discrimination between Subject Classes. The distributions of serum analyte levels were compared by Kruskal-Wallis one-way analysis of variance by ranks (FIG. 9). Nineteen analytes (ALCAM, AXL, CA 19-9, CEACAM1, COL18A1, EPCAM, HA, HP, ICAM1, IGFBP2, IGFBP4, MMP2, MMP7, SPP1, PRG4, TGFBI, THBS1, TIMP1, TNFRSF1A) had significant differences between healthy controls (CON), chronic pancreatitis (ChPT), and early stage pancreatic cancer (PDAC) classes, while an additional four analytes (BAG3, BSG, LCN2, PARK7) trended towards significance.

Since age was a significant predictor of diagnosis (P=0.0006 by Kruskal-Wallis), and since gender was unequally distributed within the classes (Table 6), subsequent analyses were performed using adjusted data. Analyte data was log 10 transformed and adjusted for age and gender using the control data. A natural spline with 2 degrees of freedom was used to adjust for age. Receiver operating characteristic (ROC) curves were generated for each analyte and areas under the ROC curve calculated (Table 5). ALCAM, AXL, CA 19-9, CEACAM1, COL18A1, HA, HP, ICAM1, IGFBP2, MMP2, PRG4, SPP1, TGFBI, TIMP1, and TNFRSF1A (15 analytes) showed capacity for discriminating healthy controls from early stage PDAC cases, ALCAM, AXL, BSG, CA 19-9, CEACAM1, EPCAM, HA, ICAM1, PARK7, and TGFBI (10 analytes) showed capacity for discriminating chronic pancreatitis cases from early stage PDAC cases, ALCAM, BAG3, CA 19-9, CEACAM1, COL18A1, EPCAM, HA, HP, ICAM1, IGFBP2, IGFBP4, LCN2, MMP2, PARK7, SPP1, THBS1, TIMP1, and TNFRSF1A (18 analytes) showed capacity for discriminating healthy controls from chronic pancreatitis cases, and ALCAM, AXL, CA 19-9, CEACAM1, COL18A1, HA, ICAM1, IGFBP2, PARK7, SPP1, TGFBI, and TIMP1 (12 analytes) showed capacity for discriminating both healthy controls and chronic pancreatitis cases from early stage PDAC cases.

The best performing analytes, yielding areas under the ROC curve greater than 0.70, were ALCAM, AXL, CA 19-9, CEACAM1, HA, ICAM1, IGFBP2, and SPP1 (8 analytes) for discriminating healthy controls from early stage PDAC cases, CA 19-9 and CEACAM1 (2 analytes) for discriminating chronic pancreatitis cases from early stage PDAC cases, EPCAM, ICAM1, IGFBP2, and SPP1 (4 analytes) for discriminating healthy controls from chronic pancreatitis cases, and ALCAM, CA 19-9, CEACAM1, and ICAM1 (4 analytes) for discriminating both healthy controls and chronic pancreatitis cases from early stage PDAC cases.

Performance of Analyte Panels for Discrimination between Subject Classes.

Figure 10A:
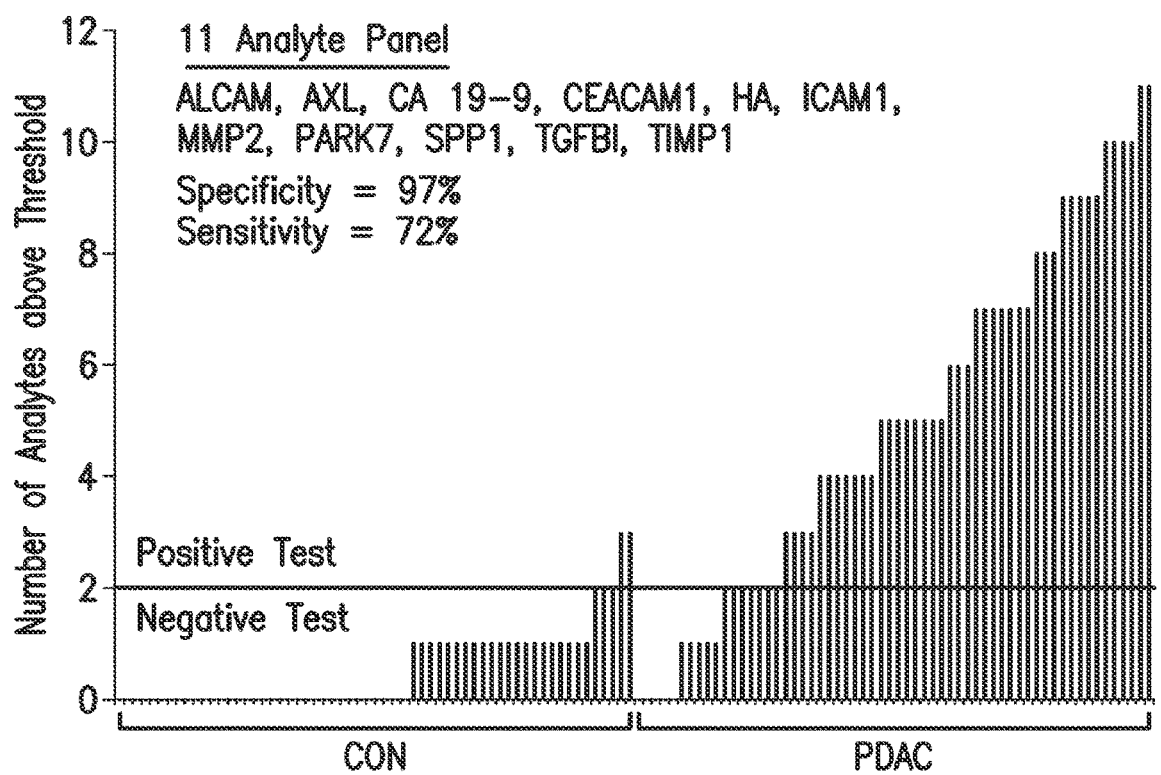
FIG. 10A-B show representative cascade plots for the threshold voting method used to identify diagnostic analyte panels. Each data point (tick mark) on the x-axis represents a unique sample. Individual analytes were assigned thresholds at the 95% percentile (95% specificity) for healthy controls (FIG. 10A) or the 95% percentile for healthy controls together with chronic pancreatitis cases (FIG. 10B). The numbers of analytes above the individual thresholds were then tabulated for all cases, including early stage PDAC cases. The number of votes (analytes above threshold) required to indicate the presence of disease (positive test) were chosen to yield high-specificity panels and the resulting sensitivity calculated. CON=healthy control subjects (N=60); ChPT=chronic pancreatitis subjects (N=60); PDAC=early stage pancreatic adenocarcinoma subjects (N=60).
Figure 10B:
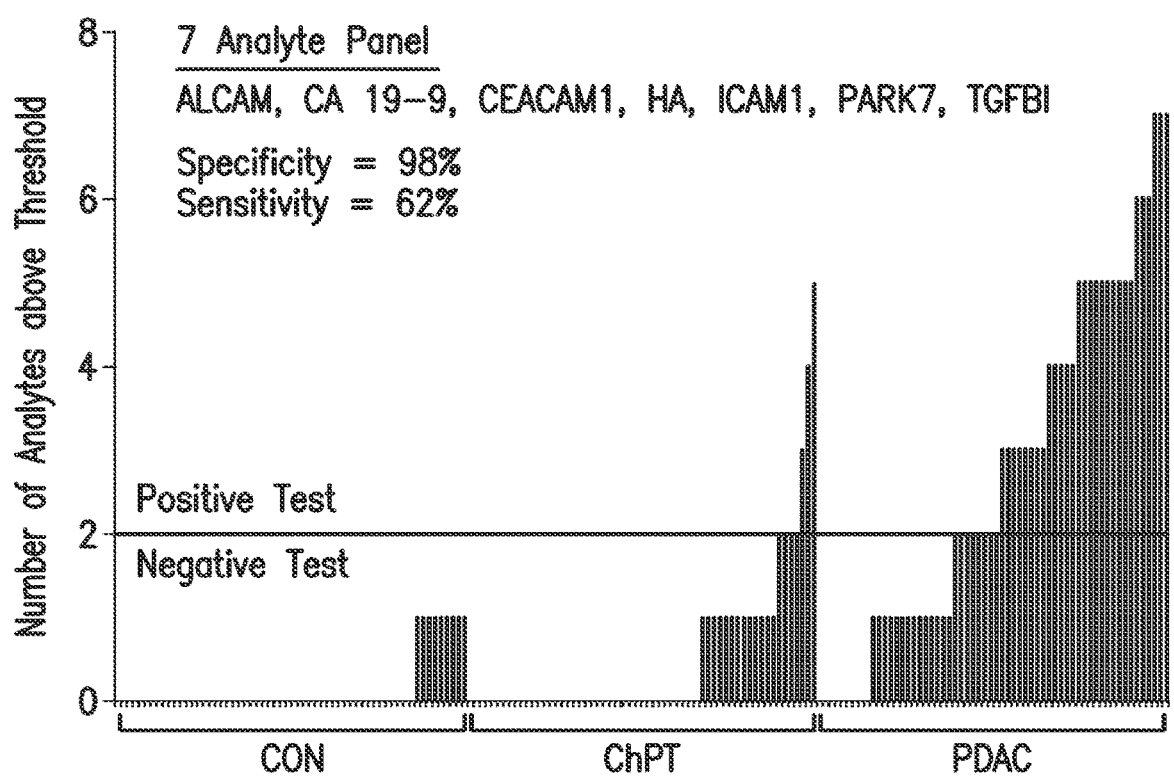

A threshold voting scheme, illustrated in FIG. 10 and described in Firpo et al., 2014, Theor Biol Med Model, 11(1):34, was applied to the comprehensive ELISA data set. Using age/gender adjusted, log 10 data, the 11 analyte panel consisting of ALCAM, AXL, CA 19-9, CEACAM1, HA, ICAM1, MMP2, PARK7, SPP1, TGFBI, and TIMP1, with any 3 analytes above the individual threshold (vote) yielded a specificity of 97% and a sensitivity of 72% for discriminating between healthy control subjects and early stage PDAC cases (FIG. 10, panel A). A 7 analyte panel consisting of ALCAM, CA 19-9, CEACAM1, HA, ICAM1, PARK7, and TGFBI with any 3 analytes above the individual threshold yielded a specificity of 98% and a sensitivity of 62% for discriminating both healthy controls and chronic pancreatitis cases from early stage PDAC cases (FIG. 10, panel B). In order to reduce the impact of selection bias and overfitting, the threshold voting scheme was applied to the CON and PDAC data using a cross-validation approach. Here, the sample sets were divided into 10 non-overlapping groups of roughly equal size, 9 of which were used as a training set and the remaining group as a test set to generate less biased estimates of error rates. This procedure was repeated 10 times to stabilize estimates. The selection of the analytes as well as the cutoff thresholds was part of the cross-validation (as is appropriate). Requiring specificity of 95% or higher and sensitivity of 25% or higher for each selected analyte, a 10 analyte panel consisting of ALCAM, AXL, CA 19-9, CEACAM1, HA, ICAM1, MMP2, SPP1, TGFBI, and TIMP1 yielded uncorrected sensitivity and specificity of 70% and 98.3% respectively. The cross-validated sensitivity and specificity of 69.8% and 95.3% respectively illustrate the expected accuracy of the 10-analyte panel when applied to new samples for diagnostic purposes.

Performance of Predictive Algorithms for Discrimination between Subject Classes.

The comprehensive data set was analyzed using various ensemble prediction methods (Table 4) for each of four class comparisons (CON vs. PDAC, ChPT vs. PDAC, CON vs. ChPT, and CON+ChPT vs. PDAC). To minimize bias in method selection, the ensemble algorithms themselves were also subjected to cross-validation using the SuperLearner prediction method, which seeks to find the optimal combination of a collection of prediction algorithms by minimizing the cross-validated risk. For each class comparison, the Random Forest method identified an algorithm that could categorize each sample to the correct class with 100% accuracy. For each class comparison, the SuperLearner identified an algorithm with the lowest mean squared error and cross-validated probability of correct classification of between 72% and 83.3%.

Brief Description of Algorithms.

Random forest—ensemble learning method for classification and regression that operates by constructing a multitude of decision trees (training) and outputting the class that is either the mode of the classes (classification) or mean prediction (regression) of the individual trees. The random forest technique is less prone to overfitting the training set than the decision tree technique. Recursive partitioning—decision tree analysis that strives to correctly classify members of a population based on dichotomous independent variables. The resulting classification scheme is generally intuitively obvious, does not require a mathematical formula, and can be tuned to emphasize specificity or sensitivity, but is prone to overfitting. Generalized linear model—a generalization of ordinary linear regression that allows for response variables that have arbitrary distributions (rather than normal distributions), and for an arbitrary function of the response variable (the link function) to vary linearly with the predicted values (rather than assuming that the response itself must vary linearly). K nearest neighbors—a non-parametric method used for classification and regression with the input consists of the k closest training examples in the feature space. An object is classified by a majority vote of its neighbors, with the object being assigned to the class most common among its k nearest neighbors, or a value assigned that is the average of the values of its k nearest neighbors. Neural network learning algorithm used to estimate or approximate functions that can depend on a large number of inputs and are generally unknown, consisting of sets of adaptive weights (i.e. numerical parameters that are tuned by a learning algorithm) and are capable of approximating non-linear functions of their inputs.

Support vector machine—supervised learning models with associated learning algorithms used for classification and regression analysis. Given a set of training examples, the training algorithm builds a model that assigns new examples into one category or the other, making it a non-probabilistic binary linear classifier. An SVM model is a representation of the examples as points in space, mapped so that the examples of the separate categories are divided by a clear gap that is as wide as possible. New examples are then mapped into that same space and predicted to belong to a category based on which side of the gap they fall on. SVMs can also perform a non-linear classification mapping their inputs into high-dimensional feature spaces.

SuperLearner—a prediction method designed to find the optimal combination of a collection of prediction algorithms by assessing the combination of algorithms minimizing the cross-validated risk. The SuperLearner was originally described in van der Laan et al., (2007) Stat Appl Genet Mol Biol, 6: Article 25 PMID: 17910531. Each of the aforementioned algorithms are known to those skilled in the art.

In general, the predictive algorithms, including the SuperLearner, require the full analyte data set as input in the context of screening new samples. The specific analytes contributing to prediction are not readily accessible. However, for each class comparison, specific analytes were identified by the random forest prescreen applied to the generalized linear model. They were ALCAM, CA 19-9, CEACAM1, HA, ICAM1, IGFBP2, LCN2, SPP1, TGFBI, and THBS1 for discriminating healthy controls from early stage PDAC cases, ALCAM, CA 19-9, CEACAM1, EPCAM, ICAM1, MSLN, PARK7, SPARCL1, TGFBI, and TIMP1 for discriminating chronic pancreatitis cases from early stage PDAC cases, CEACAM1, EPCAM, HA, HP, ICAM1, IGFBP2, LCN2, MMP2, SPP1, and THBS1 for discriminating healthy controls from chronic pancreatitis cases, and ALCAM, AXL, CA 19-9, CEACAM1, COL18A1, HA, ICAM1, LCN2, MMP2, TGFB1 discriminating both healthy controls and chronic pancreatitis cases from early stage PDAC cases.

The resulting algorithms can be applied to new samples for diagnostic screening. The expected accuracy of such tests is listed in Table 7 (Cross validated probability of correct classification). Furthermore, the algorithms can be modified to accommodate adaptive learning, as confirmatory diagnoses become available for new samples. Increased accuracy of the algorithms can be achieved by incorporating additional analytes (measured in each of the input samples), such as miRNA signals, tumor DNA signals, autoantibody signals, as well as additional peptide and polysaccharide signals.

TABLE 7

Algorithms applied to new samples for diagnostic screening

| Algorithm | Uncorrected probability of correct classification | Cross-validated Risk, mean squared error (SE) | Cross validated probability of correct classification | Fractional contribution in SuperLearner |
|---|---|---|---|---|
| Evaluation of algorithms for CON vs. PDAC | | | | |
| glmnet | 0.875 | 0.137 (0.017) | 0.825 | 0 |
| randomForest | 1.00 | 0.121 (0.016) | 0.858 | 0.415 |
| rpart | 0.883 | 0.181 (0.029) | 0.783 | 0 |
| glm + pre-screen | 0.858 | 0.157 (0.024) | 0.767 | 0.066 |
| knn | 0.850 | 0.137 (0.019) | 0.833 | 0.491 |
| nnet | 0.917 | 0.147 (0.029) | 0.842 | 0.028 |
| svm | 0.958 | 0.142 (0.019) | 0.808 | 0 |
| mean | 0.500 | 0.254 (0.001) | 0.400 | 0 |
| SuperLearner | | 0.115 (0.017) | 0.833 | — |
| CA 19-9 | 0.833 | | 0.824 | |
| Evaluation of algorithms for ChPT vs. PDAC | | | | |
| glmnet | 0.767 | 0.201 (0.017) | 0.692 | 0 |
| randomForest | 1.00 | 0.162 (0.015) | 0.775 | 0.039 |
| rpart | 0.883 | 0.200 (0.029) | 0.742 | 0.185 |
| glm + pre-screen | 0.775 | 0.193 (0.024) | 0.742 | 0.016 |
| knn | 0.800 | 0.169 (0.017) | 0.725 | 0.613 |
| nnet | 0.900 | 0.223 (0.034) | 0.733 | 0 |
| svm | 0.983 | 0.178 (0.019) | 0.750 | 0.147 |
| mean | 0.500 | 0.253 (0.001) | 0.417 | 0 |
| SuperLearner | | 0.171 (0.017) | 0.742 | — |
| CA 19-9 | 0.708 | | 0.713 | |
| Evaluation of algorithms for CON vs. CHPT | | | | |
| glmnet | 0.808 | 0.198 (0.019) | 0.708 | 0 |
| randomForest | 1.00 | 0.175 (0.015) | 0.708 | 0.559 |
| rpart | 0.842 | 0.193 (0.026) | 0.700 | 0 |
| glm + pre-screen | 0.750 | 0.214 (0.027) | 0.692 | 0.262 |
| knn | 0.733 | 0.207 (0.019) | 0.675 | 0.173 |
| nnet | 0.933 | 0.275 (0.033) | 0.633 | 0.006 |
| svm | 0.967 | 0.197 (0.019) | 0.733 | 0 |
| mean | 0.500 | 0.256 (0.002) | 0.383 | 0 |
| SuperLearner | | 0.193 (0.019) | 0.717 | — |
| CA 19-9 | 0.600 | | 0.590 | |
| Evaluation of algorithms for CON + ChPT vs. PDAC | | | | |
| glmnet | 0.828 | 0.147 (0.018) | 0.794 | 0.133 |
| randomForest | 1.00 | 0.128 (0.015) | 0.867 | 0 |
| rpart | 0.883 | 0.141 (0.021) | 0.833 | 0.171 |
| glm + pre-screen | 0.861 | 0.147 (0.018) | 0.822 | 0 |
| knn | 0.872 | 0.130 (0.017) | 0.828 | 0.373 |
| nnet | 0.917 | 0.210 (0.016) | 0.778 | 0.177 |
| svm | 0.922 | 0.134 (0.016) | 0.828 | 0.145 |

TABLE 7-continued

Algorithms applied to new samples for diagnostic screening

| Algorithm | Uncorrected probability of correct classification | Cross-validated Risk, mean squared error (SE) | Cross validated probability of correct classification | Fractional contribution in SuperLearner |
|---|---|---|---|---|
| mean | 0.667 | 0.224 (0.011) | 0.667 | 0 |
| SuperLearner | | 0.127 (0.016) | 0.833 | — |
| CA 19-9 | 0.767 | | 0.762 | | a) glmnet—a version of Lasso regression;
b) randomForest—random forest;
c) rpart—recursive partitioning;
d) glm + prescreen—the generalized linear model. The random forest prescreen was used to avoid overfitting which caused non-convergence for some of the cross-validation model;
e) knn—k nearest neighbors;
f) nnet—neural network;
g) svm—support vector machine;
h) mean—the predicted probability is the overall mean for every case (=0.5 for the full data);
i) SuperLearner—the NNLS algorithm was used to fit the SuperLearner, with the binomial family. 10-fold cross validation was used both within the SuperLearner to evaluate each algorithm and to evaluate the SuperLearner.

Example 7. Performance of the Diagnostic SuperLearner Algorithm Compared to CA 19-9 Alone This example demonstrates that the SuperLearner has improved performance over CA 19-9 alone when applied to additional samples.

Figure 7:
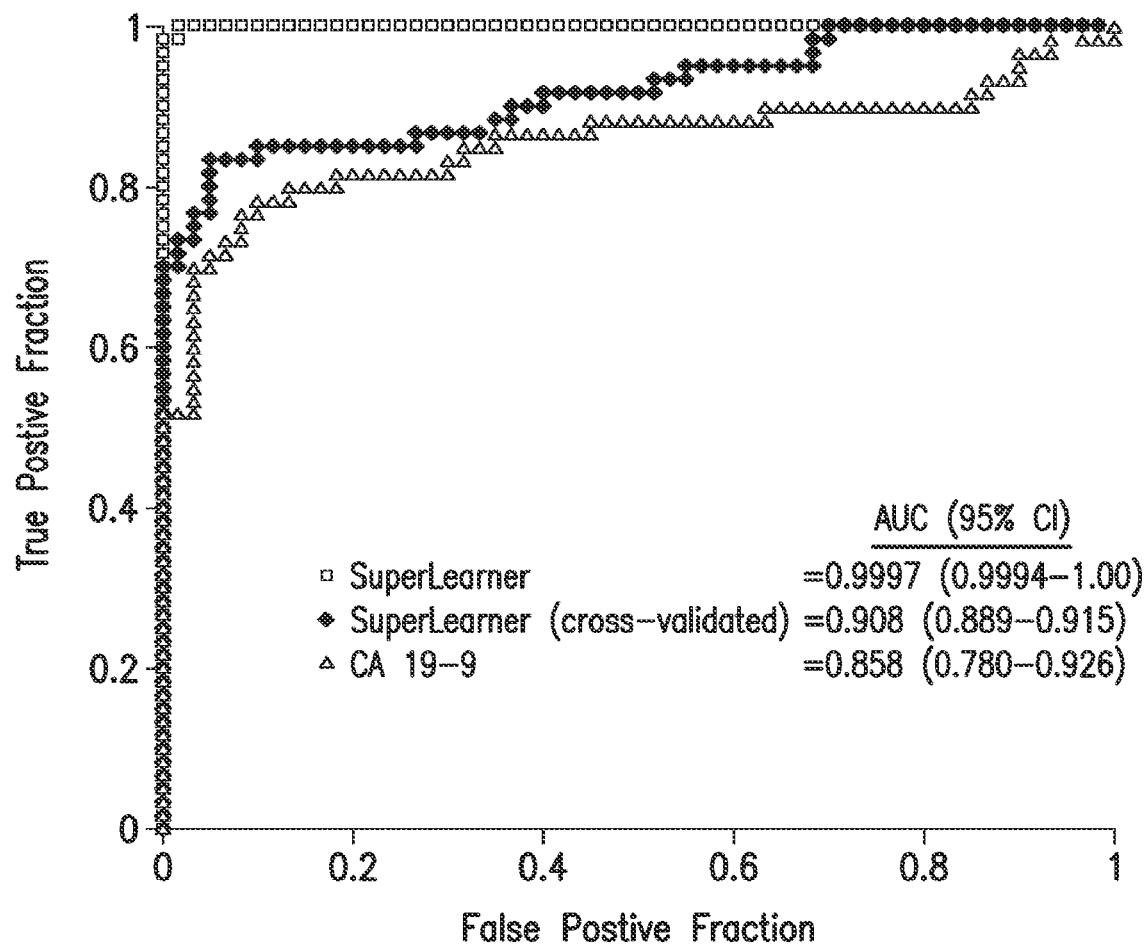
FIG. 7 shows the diagnostic performance of the SuperLearner compared to CA 19-9 alone for distinguishing healthy control subjects from early stage PDAC cases. Receiver operating characteristic curves are shown for the CON vs. PDAC SuperLearner applied to the actual data (red squares), the cross-validated SuperLearner data (blue diamonds), and bootstrap data for CA 19-9 alone (green triangles). These data indicate that the SuperLearner will have improved performance over CA 19-9 alone when applied to additional samples

To evaluate the SuperLearner over all threshold cutoffs, receiver operating characteristic analyses were performed. The SuperLearner provides predicted probabilities for each observation and these predicted probabilities can be used to generate an ROC curve in the same way that an ROC curve can be generated from any other continuous variable (such as the values from a single analyte). For each possible predicted probability value there is a true positive fraction and a false positive fraction, and one can plot them against each other. To generate unbiased estimates, the predicted probabilities were generated by cross-validation in which the SuperLearner was trained on 90% of the data from the 30 analytes listed in Table 1, and predictions are made on the other 10%. This was repeated 10 times, with a different 10% of the data in the validation set each time. Similarly, for the individual analytes (Table 3 and FIG. 7), the ROC AUCs reported were generated by bootstrap resampling (2000×) and represent estimated error rates from samples in the test sets. The cross-validated and bootstrap AUCs thus reflect the expected accuracy in new sample sets. The CA 19-9 ROC curve and AUC is comparable to the cross-validated SuperLearner ROC curve and AUC (FIG. 7). The relative improvement of the cross-validated SuperLearner over CA 19-9 alone was 35%, [(0.908-0.858)/(1-0.858)]×100.

Figure 8A:
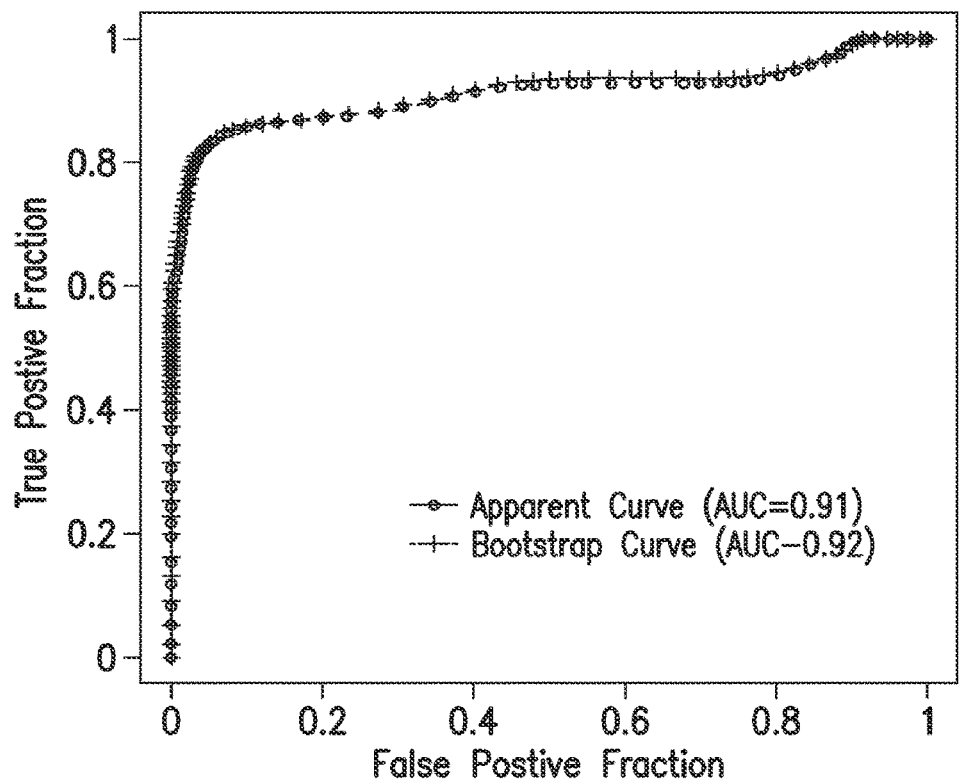
FIGS. 8A-B show receiver operating characteristic curves for panels derived by feature selection lasso procedure for discriminating healthy controls and early stage PDAC cases FIG. 8A) and for discriminating both healthy controls and chronic pancreatitis cases from early stage PDAC cases (FIG. 8B).
Figure 8B:
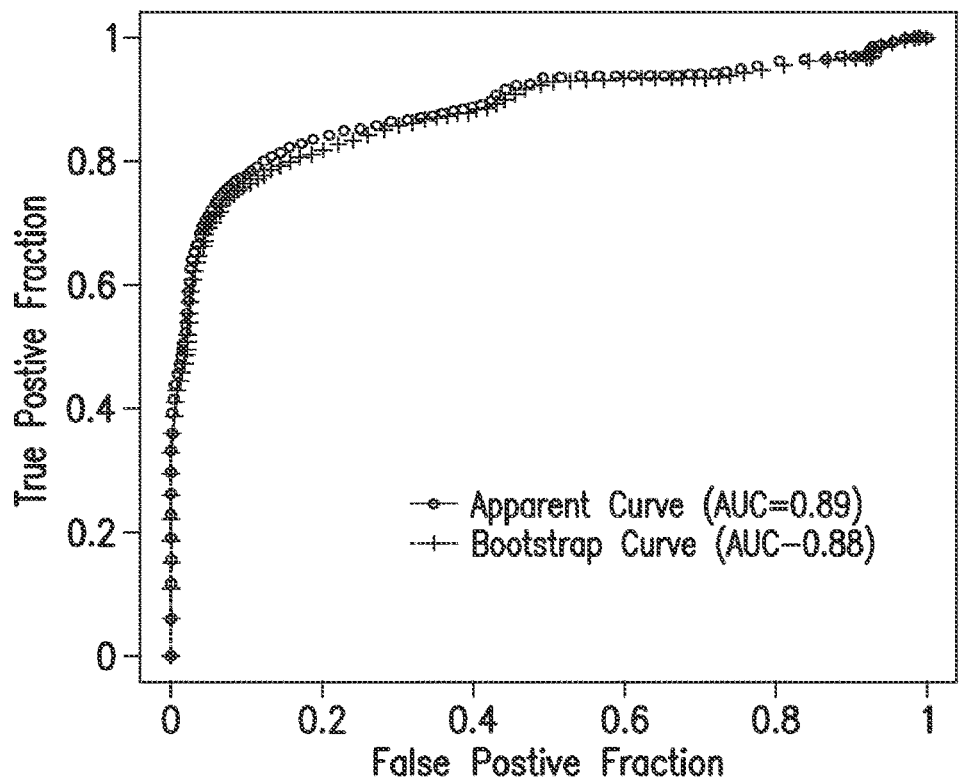

Example 8. Feature Selection Maximizing Area Under the Receiver Operating Characteristics Curve The ensemble techniques illustrated in Table 7 function by minimizing the mean squared error associated with the diagnostic test. We also evaluated the 30-analyte panel using a technique that maximizes area under the receiver operating characteristic curve and identifies analytes that most contribute to class discrimination using the lasso (least absolute shrinkage and selection operator) procedure. As devised, the lasso procedure seeks to reduce over-fitting of the data, which is evident in the overlap between the fitted data (FIG. 8, Apparent Curve) and the resampled data (FIG. 8, Bootstrap Curve). For the comparison of healthy controls from early stage PDAC (FIG. 8A), the optimal panel included analytes BAG3, CA 19-9, CEACAM1, HA, IGFBP2, PARK7, and SPP1. For the comparison of healthy controls+ chronic pancreatitis from early stage PDAC (FIG. 8B), the optimal panel included analytes BAG3, CA 19-9, CEACAM1, EPCAM, LCN2, MSLN, PARK7, PRG4, SPP1, and TNFRSF1A. These data suggest that comparably accurate algorithms can be devised using subsets of the 30 analyte panel.

Example 9. Identification of Novel Biomarkers for Early Stage PDAC

This example describes identification of novel biomarkers for diagnosis of early stage PDAC.

The analytes listed in Tables 4 and 5 feature 8 novel analytes (ALCAM, BAG3, BSG, HA, PARK7, PRG4, SPARCL1, and TGFBI) that have not been previously systematically evaluated for their ability to contribute to early stage PDAC diagnosis. All 8 analytes likely contribute at least orthogonal information to the ensemble algorithms, including the SuperLearners. Additionally, 7 of these 8, ALCAM, BAG3, HA, PARK7, PRG4, SPARCL1, and TGFBI, were specifically identified as contributing to diagnostic algorithms, either in the threshold-voting scheme, the Random Forest prescreen to the generalized linear model, or by feature selection via maximizing the area under the receiver operating characteristic curve. Several of these analytes were identified in multiple algorithms. The eighth novel analyte, BSG, was shown to be specifically elevated in plasma samples from early stage PDAC cases (FIG. 1), providing support for the contribution of BSG to orthogonal information in the ensemble algorithms.

From the foregoing description, it will be apparent that variations and modifications can be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. An array comprising at least two antibodies or antibody fragments attached to a solid support that specifically bind to at least basigin and soluble hyaluronic acid, respectively.

2. A method of diagnosing and treating early stage pancreatic ductal adenoncarcinoma (PDAC) in an individual, the method comprising:
   obtaining a serum or plasma sample from an individual;
   detecting an elevated protein level of basigin and soluble hyaluronic acid (HA) in the serum or plasma sample when compared to a reference sample, thereby diagnosing the individual with early stage PDAC, wherein the detecting of the elevated protein levels of basigin and HA is performed using a capture agent or an immunoassay, wherein said capture agent is selected from the group consisting of and antibody, antibody fragment, nucleic acid-based protein binding reagent, small molecule or variant thereof, wherein said immunoassay is an enzyme immunoassay (EIA), an enzyme-linked immunosorbent assay (ELISA), or a radioimmunoassay (RIA); and administering a therapy selected from the group consisting of prophylactic anticoagulants, resection, neoadjuvant chemotherapy, and chemoradiation to the individual with early stage PDAC.

3. The method of claim 2, further comprising detecting an elevated protein level of one or more of the biomarkers listed in Tables 1 through 4.

4. The method of claim 3, further comprising calculating the probability for early stage PDAC in said individual based on the elevated protein level of one or more of the biomarkers listed in Tables 1 through 4.

5. The array of claim 1, further comprising one or more isolated antibodies or antibody fragments attached to the solid support that specifically bind to ALCAM, ANG, AXL, BAG3, CA 19-9, CEA, CEACAM1, COL18A1, EPCAM, HP, ICAM1, IGFBP2, IGFBP4, LCN2, LRG1, MMP2, MMP7, MMP9, MSLN, PARK7, PPBP, PRG4, SPARCL1, SPP1, TGFBI, THBS1, TIMP1, TNFRSF1A, or VEGFC.

6. The method of claim 2, further comprising detecting an elevated protein level of one or more of ALCAM, ANG, AXL, BAG3, CA 19-9, CEA, CEACAM1, COL18A1, EPCAM, HP, ICAM1, IGFBP2, IGFBP4, LCN2, LRG1, MMP2, MMP7, MMP9, MSLN, PARK7, PPBP, PRG4, SPARCL1, SPP1, TGFBI, THBS1, TIMP1, TNFRSF1A, and VEGFC.

7. The array of claim 1, wherein the at least two isolated antibodies or antibody fragments are labeled.

8. The array of claim 5, wherein one or more of the isolated antibodies or antibody fragments attached to the solid support are labeled.

* * * * *